(12) United States Patent
Neustadt et al.

(10) Patent No.: US 7,709,492 B2
(45) Date of Patent: May 4, 2010

(54) PYRAZOLO-[4,3-E]-1,2,4-TRIAZOLO-[1,5-C]-PYRIMIDINE ADENOSINE $A_{2a}$ RECEPTOR ANTAGONISTS

(75) Inventors: Bernard R. Neustadt, West Orange, NJ (US); Jinsong Hao, Belle Mead, NJ (US); Hong Liu, Hackensack, NJ (US); Craig D. Boyle, Branchburg, NJ (US); Samuel Chackalamannil, Califon, NJ (US); Unmesh G. Shah, Scotch Plains, NJ (US); Andrew Stamford, Chatham Township, NJ (US); Joel M. Harris, Watchung, NJ (US)

(73) Assignee: Schering Corporation, Kenilworth, NJ (US)

( * ) Notice: Subject to any disclaimer, the term of this patent is extended or adjusted under 35 U.S.C. 154(b) by 682 days.

(21) Appl. No.: 11/108,916

(22) Filed: Apr. 19, 2005

(65) Prior Publication Data

US 2005/0239795 A1   Oct. 27, 2005

Related U.S. Application Data

(60) Provisional application No. 60/563,913, filed on Apr. 21, 2004, provisional application No. 60/609,966, filed on Sep. 15, 2004.

(51) Int. Cl.
| | | |
|---|---|---|
| *A01N 43/54* | (2006.01) | |
| *A61K 31/505* | (2006.01) | |
| *C07D 239/00* | (2006.01) | |
| *C07D 487/08* | (2006.01) | |

(52) U.S. Cl. ..................... 514/267; 544/251
(58) Field of Classification Search ................ 544/251; 514/267

See application file for complete search history.

(56) References Cited

U.S. PATENT DOCUMENTS

| | | | |
|---|---|---|---|
| 5,565,460 A | 10/1996 | Suzuki et al. | |
| 6,630,475 B2 * | 10/2003 | Neustadt et al. | 514/257 |
| 6,897,216 B2 | 5/2005 | Neustadt et al. | |
| 6,897,217 B2 | 5/2005 | Neustadt et al. | |
| 2004/0138235 A1 | 7/2004 | Grezlak | |

FOREIGN PATENT DOCUMENTS

| | | |
|---|---|---|
| WO | WO 01/92264 | 12/1991 |
| WO | WO 95/01356 | 1/1995 |
| WO | WO 97/05138 | 2/1997 |
| WO | WO 98/52568 | 11/1998 |
| WO | WO 01/92264 * | 6/2001 |
| WO | WO 01/92264 | 12/2001 |
| WO | WO 02/055083 | 7/2002 |
| WO | WO 03/032996 | 4/2003 |

OTHER PUBLICATIONS

Yaar, R., et al., Animal Models for the Study of Adenosine Receptor Function, Am. J. of Cellular Physiology, 202:9-20 (2005).*
Baraldi, et al., Pyrazolo[4,3-e]-1,2,4-triazolo . . . , J. Med Chem., 39 (1996) p. 1164-1171.
Orito, et al., Synthesis of 5-Iodobenzofurans . . . , Synthesis, (1997) p. 23-25.
Aiba, et al., Total Synthesis and Antifungal Activity . . . , Bioorganic & Medicinal Chemistry Letters, 11 (2001) p. 2783-2786.
Cornelius, et al., A Convenient Synthesis of Mono- and Polyhalogenated . . . , Synthetic Communications, 24, 19 (1994) p. 2777-2788.
Lee, et al., Facile Synthesis of Oxazoles . . . , Synthetic Communications, 33, 9 (2003) p. 1611-1614.
Ungerstedt, et al., Quantitative Recording of Rotational Behavior . . . , Brain Research, 24 (1970) p. 485-493.
Ungerstedt, 6-Hydroxy-Dopamine Induced Degeneration . . . , Opean Journal of Pharmacology, 5 (1968) p. 107-110.
International Search Report for application No. PCT/US2005/013454 dated Mar. 8, 2005.

* cited by examiner

*Primary Examiner*—James O Wilson
*Assistant Examiner*—Erich A Leeser
(74) *Attorney, Agent, or Firm*—Krishna G. Banerjee; William Y. Lee; Anita W. Magatti

(57) ABSTRACT

Compounds having the structural formula I or a pharmaceutically acceptable salt thereof, wherein
R is optionally substituted phenyl, furanyl, thienyl, pyridyl, pyridyl N-oxide, oxazolyl or pyrrolyl, or cycloalkenyl
$R^1$, $R^2$, $R^3$, $R^4$ and $R^5$ are H, alkyl or alkoxyalkyl; and
Z is optionally substituted aryl or heteroaryl are disclosed. Also disclosed is the use of compounds of formula I in the treatment of central nervous system diseases, in particular Parkinson's disease, alone or in combination with other agents for treating Parkinson's disease, and pharmaceutical compositions comprising them.

20 Claims, No Drawings

PYRAZOLO-[4,3-E]-1,2,4-TRIAZOLO-[1,5-C]-PYRIMIDINE ADENOSINE $A_{2a}$ RECEPTOR ANTAGONISTS

CROSS REFERENCE TO RELATED APPLICATIONS

This application claims the benefit of U.S. Provisional Application 60/563,913, filed Apr. 21, 2004, and U.S. Provisional Application 60/609,966, filed Sep. 15, 2004.

BACKGROUND

The present invention relates to substituted pyrazolo-[4,3-e]-1,2,4-triazolo[1,5-c]pyrimidine adenosine $A_{2a}$ receptor antagonists, the use of said compounds in the treatment of central nervous system diseases, in particular Parkinson's disease, and to pharmaceutical compositions comprising said compounds.

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ are high-affinity, inhibiting the activity of the enzyme adenylate cyclase, and $A_{2a}$ and $A_{2b}$ are low-affinity, stimulating the activity of the same enzyme. Analogs of adenosine able to interact as antagonists with the $A_1$, $A_{2a}$, $A_{2b}$ and $A_3$ receptors have also been identified.

Selective antagonists for the $A_{2a}$ receptor are of pharmacological interest because of their reduced level of side effects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses.

Some xanthine-related compounds have been found to be $A_1$ receptor selective antagonists, and xanthine and non-xanthine compounds have been found to have high $A_{2a}$ affinity with varying degrees of $A_{2a}$ vs. $A_1$ selectivity. Triazolo-pyrimidine adenosine $A_{2a}$ receptor antagonists have been disclosed previously, for example in WO 95/01356; U.S. Pat. No. 5,565,460; WO 97/05138; WO 98/52568, WO 01/92264, and WO 03/032996.

Adenosine $A_{2a}$ receptor antagonists have been disclosed as being useful in the treatment or prevention of Extra Pyramidal Syndrome, dystonia, restless leg syndrome (RLS) or periodic limb movement in sleep (PLMS) in PCT/US03/40456, filed Dec. 17, 2003, and have been disclosed as being useful in the treatment of attention deficit hyperactivity disorder (ADHD) in WO 02/055083.

SUMMARY OF THE INVENTION

The present invention relates to compounds having the structural formula I or a pharmaceutically acceptable salt thereof, wherein R is $R^6$-phenyl, $R^6$-furanyl, $R^6$-thienyl, $R^6$-pyridyl, $R^6$-pyridyl N-oxide, $R^6$-oxazolyl, $R^6$-pyrrolyl or cycloalkenyl;

$R^1$, $R^2$, $R^3$, $R^4$ and $R^5$ are independently selected from the group consisting of H, alkyl and alkoxyalkyl;

$R^6$ is 1 to 3 substituents independently selected from the group consisting of H, alkyl, —$CF_3$, halogen, —$NO_2$, —CN, —$NR^7R^8$, alkoxy, alkylthio, alkylsulfinyl and alkylsulfonyl;

$R^7$ is H or alkyl;

$R^8$ is H, alkyl, alkylC(O)— or alkyl-$SO_2$—;

Z is $R^9,R^{10}$-aryl or $R^9,R^{10}$-heteroaryl;

$R^9$ is alkenyl, hydroxyalkyl, alkoxyalkyl, alkoxy-alkoxyalkyl-, (di-alkoxy)-alkyl, (hydroxy)-alkoxyalkyl, $R^{15}$-cycloalkyl, $R^{15}$-cycloalkylalkyl, cycloalkyl-oxy, cycloalkyl-O-alkoxy, cyanoalkyl, —C(O)$R^{13}$, —N($R^{11}$)($R^{12}$), N($R^{11}$)($R^{12}$)-alkyl-, —C(O)N($R^{13}$)($R^{16}$), -alkylene-C(O)—N($R^{11}$)$_2$, —C(O)—($R^{15}$-heterocycloalkyl), $R^{15}$-heterocycloalkyl-alkyl, $R^{15}$-heterocycloalkyl-alkoxy, $R^{19}$-heteroaryl, $CF_3$-alkylene-O-alkyl, $CF_3$-hydroxyalkyl, ($CF_3$)(hydroxy)alkoxy, cyano-alkoxy, -alkylene-C(O)—O-alkyl, —$SO_2$—N(alkyl)$_2$, (cycloalkyl)hydroxyalkyl, (hydroxyalkyl)alkoxy, (dihydroxy)alkyl, (dihydroxy)alkoxy or —C(=NOR$^{17}$)—CF$_3$;

$R^{10}$ is 1 to 3 substituents independently selected from the group consisting of hydrogen, alkyl, alkenyl, hydroxy, alkoxy, hydroxyalkyl, hydroxy-alkoxy, alkoxyalkyl, alkoxyalkoxy, alkoxy-alkoxy-alkyl-, (di-alkoxy)-alkyl, (hydroxy)-alkoxyalkyl, $R^{15}$-cycloalkyl, $R^{15}$-cycloalkylalkyl, cycloalkyl-oxy, cycloalkyl-O-alkoxy, alkyl-$SO_2$—, alkyl-SO—, halo, —CN, cyanoalkyl, —$CHF_2$, —$CF_3$, —$OCHF_2$, —$OCF_3$, —C(O)$R^{13}$, —O-alkylene-C(O)O$R^{13}$, —C(O)O-alkyl, —N($R^{11}$)($R^{12}$), N($R^{11}$)($R^{12}$)-alkyl, N($R^{11}$)($R^{12}$)-alkoxy, —C(O)N($R^{13}$)($R^{16}$), $R^{19}$-heteroaryl, $R^{15}$-heterocycloalkyl, $R^{15}$-heterocycloalkyl-alkyl, $R^{15}$-heterocycloalkyl-alkoxy, $R^{15}$-heterocycloalkyl-oxy, $CF_3$-alkylene-O-alkyl, $CF_3$-hydroxyalkyl, ($CF_3$)(hydroxy)alkoxy, cyano-alkoxy, -alkylene-C(O)—O-alkyl, —$SO_2$—N(alkyl)$_2$, (cycloalkyl)hydroxyalkyl, (hydroxyalkyl)alkoxy, (dihydroxy)alkyl, (dihydroxy)alkoxy, —C(=NOR$^{17}$)-alkyl and —C(=NOR$^{17}$)—CF$_3$;

or an $R^9$ group and an $R^{10}$ group on adjacent carbon ring atoms together form —O—(CH$_2$)$_2$—O—, —CH$_2$—O—(CH$_2$)$_2$—O—, —O—(CH$_2$)$_2$—, —(CH$_2$)$_3$—O—, —O—(CH$_2$)$_3$—O—, —(CH$_2$)$_3$— or —CH$_2$—CH=CH—, wherein the ring formed by the $R^9$ and $R^{10}$ substituents and the ring carbon atoms to which they are attached is substituted by $R^{16}$;

or an $R^9$ group and an $R^{10}$ group on adjacent carbon ring atoms together form —$N(R^{11})$—$C(O)$—$O$—, —$N(R^{11})$—$C(O)$—$S$— or —$N(R^{12})$—$(CH_2)_2$—;

or an $R^9$ group and an $R^{10}$ group on adjacent carbon ring atoms together form —$(CH_2)_2CH(OR^{18})$—, —$CH_2CH(OR^{18})CH_2$—, —$(CH_2)_3CH(OR^{18})$—, —$(CH_2)_2CH(OR^{18})CH_2$—, —$(CH_2)_2C(O)$—, —$CH_2C(O)CH_2$—, —$(CH_2)_3C(O)$—, —$(CH_2)_2C(O)CH_2$—, —$O(CH_2)_2CH(OR^{18})$— or —$OCH_2CH(OR^{18})CH_2$—, wherein the ring formed by the $R^9$ and $R^{10}$ substituents and the ring carbon atoms to which they are attached is optionally substituted on a carbon atom by hydroxyalkyl or alkoxyalkyl;

each $R^{11}$ is independently selected from the group consisting of H and alkyl;

each $R^{12}$ is independently selected from the group consisting of H, alkyl, cycloalkyl, hydroxyalkyl, alkoxyalkyl, —C(O)-alkyl, —C(O)O-alkyl, (alkoxy)hydroxyalkyl, alkoxyalkyl-C(O)—, —SO$_2$alkyl, -alkylene-C(O)alkyl and -alkylene-C(O)O-alkyl;

$R^{13}$ is H, alkyl or —$CF_3$;

$R^{15}$ is 1 to 3 substituents independently selected from the group consisting of H, alkyl, —OH, alkoxy, alkoxyalkyl and hydroxyalkyl; or two $R^{15}$ substituents, taken together with the carbon to which they are both attached, form a —C(=O)— group;

$R^{16}$ is H, alkyl, alkoxyalkyl, OH or hydroxyalkyl;

$R^{17}$ is H or alkyl;

$R^{18}$ is H or alkyl; and $R^{19}$ is 1 or 2 substituents independently selected from the group consisting of H, alkyl, hydroxyalkyl, alkoxyalkyl, —C(O)N($R^{11}$)($R^{12}$) and —N($R^{11}$)$_2$.

Another aspect of the invention is a pharmaceutical composition comprising a therapeutically effective amount of at least one compound of formula I in a pharmaceutically acceptable carrier.

Yet another aspect of the invention is a method of treating central nervous system diseases such as depression, cognitive diseases and neurodegenerative diseases such as Parkinson's disease, senile dementia or psychoses, and stroke, comprising administering at least one compound of formula I to a mammal in need of such treatment.

The invention also relates to the treatment of attention related disorders such as attention deficit disorder (ADD) and attention deficit hyperactivity disorder (ADHD). The invention also relates to the treatment or prevention of Extra-Pyramidal Syndrome (e.g., dystonia, akathisia, pseudoparkinsonism and tardive dyskinesia), the treatment of primary (idiopathic) dystonia, and the treatment or prevention of dystonia in patients who exhibit dystonia as a result of treatment with a tricyclic antidepressant, lithium or an anticonvulsant, or who have used cocaine, comprising administering at least one compound of formula I to a mammal in need of such treatment. The invention further relates to treatment of abnormal movement disorders such as restless leg syndrome (RLS) or periodic limb movement in sleep (PLMS), comprising administering to a patient in need thereof a therapeutically effective amount of at least one compound of formula I.

In particular, the invention is drawn to the method of treating Parkinson's disease comprising administering at least one compound of formula I to a mammal in need of such treatment.

Still another aspect of the invention is a method of treating Parkinson's disease with a combination of at least one compound of formula I and one or more agents useful in the treatment of Parkinson's disease, for example dopamine; a dopaminergic agonist; an inhibitor of monoamine oxidase, type B (MAO-B); a DOPA decarboxylase inhibitor (DCI); or a catechol-O-methyltransferase (COMT) inhibitor. Also claimed is a pharmaceutical composition comprising at least one compound of formula I and one or more agents known to be useful in the treatment of Parkinson's disease in a pharmaceutically acceptable carrier.

The invention also comprises a method of treating RLS or PLMS comprising administering a combination of at least one compound of formula I with another agent useful in treating RLS or PLMS, such as levodopa/carbidopa, levodopa/benserazide, a dopamine agonist, a benzodiazepine, an opioid, an anticonvulsant or iron, to a patient in need thereof.

DETAILED DESCRIPTION

Preferred compounds of formula I are those wherein R is $R^6$-phenyl, $R^6$-furanyl, $R^6$-thienyl, $R^6$-pyridyl or $R^6$-oxazolyl, more preferably $R^6$-furanyl or $R^6$-pyridyl. $R^6$ is preferably H, halogen or alkyl, especially H, F or methyl.

$R^1$, $R^2$, $R^3$, $R^4$ and $R^5$ are each preferably H.

A preferred definition for Z is $R^9,R^{10}$-aryl, more preferably $R^9,R^{10}$-phenyl. When Z is $R^9,R^{10}$-phenyl, $R^9$ is preferably hydroxyalkyl, alkoxyalkyl, (hydroxy)-alkoxyalkyl, (hydroxyalkyl)alkoxy, $R^{15}$-cycloalkyl, cyanoalkyl, $R^{19}$-heteroaryl, or (cycloalkyl)hydroxyalkyl, and $R^{10}$ is preferably 1 or 2 substituents independently selected from the group consisting of H, halo, —C(O)$R^{13}$, alkoxy, hydroxyalkyl, hydroxyalkoxy, alkoxyalkoxy, alkoxyalkyl, and cyanoalkyl. More preferably, $R^9$ is hydroxyalkyl (e.g., hydroxyethyl), (hydroxyalkyl)alkoxy (e.g., —CH(OCH$_3$)(CH$_2$OH)), $R^{15}$-cycloalkyl, cyanoalkyl (e.g., cyanomethyl), $R^{19}$-heteroaryl, or (cycloalkyl)-hydroxyalkyl, and $R^{10}$ is preferably 1 or 2 substituents independently selected from the group consisting of H, halo and alkoxy. Especially preferred are compounds wherein there is one $R^{10}$ substituent, in particular wherein the $R^{10}$ substituent is fluoro, more particularly o-fluoro. When $R^9$ is $R^{15}$-cycloalkyl, cycloalkyl is preferably cyclopropyl and $R^{15}$ is preferably OH (e.g., 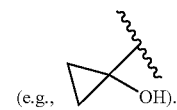).

When $R^9$ is $R^{19}$-heteroaryl, heteroaryl is preferably oxazolyl or oxadiazolyl and $R^{19}$ is preferably alkyl, hydroxyalkyl or alkoxyalkyl, for example methyl, —C(CH$_3$)$_2$OH or methoxymethyl.

When Z is $R^9,R^{10}$-heteroaryl, the heteroaryl moiety is preferably pyridyl. $R^9$ is preferably hydroxyalkyl, alkoxyalkyl, (hydroxy)-alkoxyalkyl, (hydroxyalkyl)alkoxy or cyanoalkyl, and $R^{10}$ is preferably 1 or 2 substituents independently selected from H, halo and alkyl.

A preferred embodiment is a compound of formula I wherein R is $R^6$-furanyl or $R^6$-pyridyl; $R^2$, $R^3$, $R^4$ and $R^5$ are each H; and Z is $R^9$, $R^{10}$-phenyl, wherein $R^9$ is hydroxyalkyl, cyanoalkyl, (hydroxyalkyl)alkoxy, $R^{15}$-cycloalkyl, $R^{19}$-heteroaryl, or (cycloalkyl)hydroxyalkyl, and $R^{10}$ is o-fluoro.

In the above definitions, "$R^9,R^{10}$-aryl" and "$R^9,R^{10}$-heteroaryl" refer to aryl and heteroaryl groups having both an $R^9$ and an $R^{10}$ substituent.

As used herein, the term alkyl includes straight or branched aliphatic hydrocarbon chains of 1 to 6 carbon atoms, e.g., methyl, ethyl, isopropyl and t-butyl.

"Aryl" means an aromatic monocyclic or multicyclic ring system comprising 6 to about 14 carbon atoms, preferably 6 to about 10 carbon atoms. Non-limiting examples of suitable aryl groups include phenyl and naphthyl.

Heteroaryl means a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1,5 or 1,7), imidazopyridyl, pyridopyrimidinyl and 7-azaindolyl. Examples of benzofused heteroaryl groups are indolyl, quinolyl, isoquinolyl, phthalazinyl, benzothienyl (i.e., thianaphthenyl), benzimidazolyl, benzofuranyl, benzoxazolyl, benzisoxazolyl, benzothiazolyl and benzofurazanyl. All positional isomers are contemplated, e.g., 2-pyridyl, 3-pyridyl and 4-pyridyl. The terms $(R^9, R^{10})$—, $R^{11}$ and $R^{19}$-substituted heteroaryl refer to such groups wherein substitutable ring carbon atoms have a substituent as defined above. When the heteroaryl group is a benzofused ring, the substituents can be attached to either or both the phenyl ring portion and the heteroaromatic ring portion, and the heteroaryl group can be attached to the rest of the molecule either through the phenyl ring portion or the heteroaromatic ring portion.

Heterocycloalkyl means a saturated ring of 4 to 7 atoms, preferably 5 or 6 ring atoms, wherein 1 or 2 ring members are selected from the group consisting of O, S and $NR^{13}$ and the remaining atoms are carbon. There are no adjacent oxygen and/or sulfur atoms in the rings. Non-limiting examples of heterocycloalkyl rings are piperidyl, pyrrolidinyl, piperazinyl, morpholinyl, thiomorpholinyl, thiazolidinyl, 1,3-dioxolanyl, 1,4-dioxanyl, oxazolinyl, tetrahydrofuranyl, tetrahydrothiophenyl and tetrahydrothiopyranyl.

"Hydroxyalkyl" means a HO-alkyl- group in which alkyl is as previously defined. Non-limiting examples of suitable hydroxyalkyl groups include hydroxymethyl and 2-hydroxyethyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkylthio" means an alkyl-S— group in which the alkyl group is as previously described. Non-limiting examples of suitable alkylthio groups include methylthio, ethylthio and isopropylthio. The bond to the parent moiety is through the sulfur.

"Cycloalkyl" means a non-aromatic monocyclic ring system comprising 3 to about 6 carbon atoms. Non-limiting examples of suitable monocyclic cycloalkyls include cyclopropyl, cyclopentyl and cyclohexyl. "Cycloalkyloxy" therefore means a cycloalkyl-O— group.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. Non-limiting examples of suitable monocyclic cycloalkenyls include cyclopentenyl, cyclohexenyl, cycloheptenyl, and the like.

Non-limiting example of a suitable multicyclic cycloalkenyl is norbornylenyl.

Halo is fluoro, chloro, bromo or iodo.

The term "(di-alkoxy)-alkyl" means an alkyl chain substituted by two alkoxy groups. Similarly, "(hydroxy)-alkoxyalkyl" means an alkyl chain substituted by a hydroxy group and an alkoxy group; $(CF_3)$(hydroxy)alkoxy means an alkoxy group substituted by a $CF_3$ group and a hydroxy group; (cycloalkyl)hydroxyalkyl means a hydroxyalkyl group substituted by a cycloalkyl group; (dihydroxy)alkyl means an alkyl chain substituted by two hydroxy groups; and (dihydroxy)alkoxy means an alkoxy group substituted by two hydroxy groups. In each of these substituents, the alkyl chains can be branched.

Examples of moieties formed when adjacent $R^9$ and $R^{10}$ groups form a ring with the carbons on the phenyl or heteroaryl ring to which they are attached are:

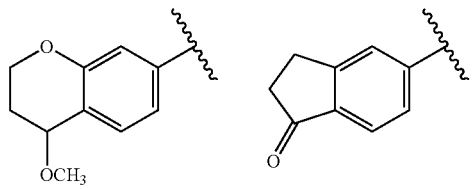

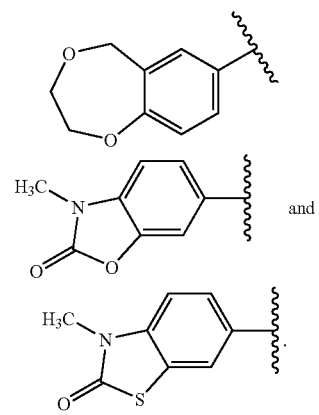

and

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

As used herein, the term "composition" is intended to encompass a product comprising the specified ingredients in the specified amounts, as well as any product which results, directly or indirectly, from combination of the specified ingredients in the specified amounts.

Lines drawn into the ring systems, such as, for example:

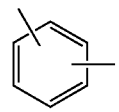

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

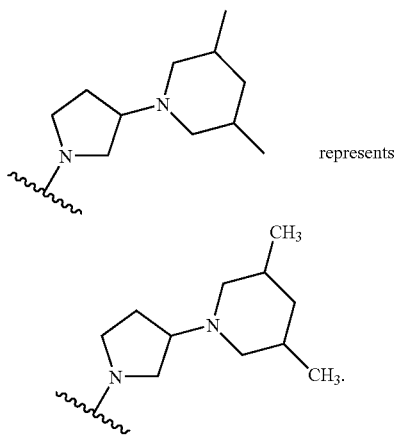

It should also be noted that any carbon or heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Polymorphic forms of the compounds of formula I, and of the salts, solvates and prodrugs of the compounds of formula I, are intended to be included in the present invention.

"Effective amount" or "therapeutically effective amount" is meant to describe an amount of compound or a composition of the present invention effective as an adenosine $A_{2a}$ receptor antagonist and thus producing the desired therapeutic effect in a suitable patient.

"Patient" includes both human and animals.

"Mammal" means humans and other mammalian animals.

The compounds of formula I form salts that are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds are known.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974

Compounds of formula I can be prepared by known methods from starting materials either known in the art or prepared by methods known in the art; see, for example, WO 95/01356, *J. Med. Chem.*, 39 (1996) 1164-1171, and WO 01/92264.

Compounds of the present invention can be prepared by several methods. A non-limiting example of a suitable method is illustrated in Scheme 1.

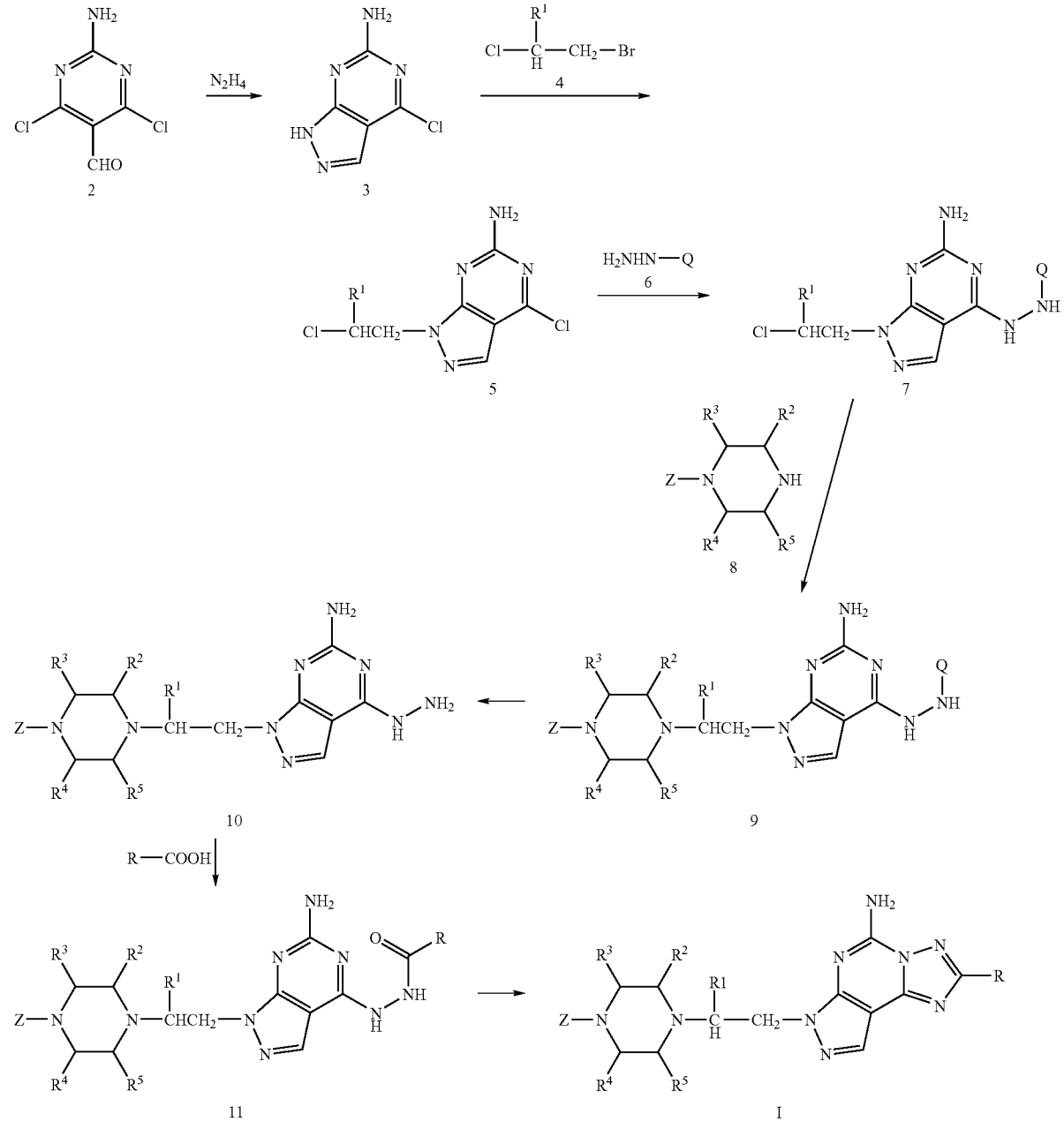

Recommendations. The use of the terms "salt", "solvate," "prodrug" and the like, is intended to equally apply to the salt, solvate and prodrug of enantiomers, stereoisomers, rotamers, tautomers, racemates or prodrugs of the inventive compounds.

Aldehyde 2 is reacted with hydrazine to furnish 3, preferably in DMF at room Temperature. Reaction of 3 with an alkylating reagent, such as bromide 4, yields Chloride 5. This conversion is carried out in the presence of a base such as NaH, in a solvent such as DMF at room temperature. Reaction of 5 with 6, a protected form of hydrazine, furnishes 7. The reaction is best carried out in DMF at elevated temperature of 80-100° C. The protective group Q is preferably t-butoxycarbonyl (Boc). Compound 7 is converted to 9 by reaction with a piperazine 8. The reaction is preferably carried out in DMF at elevated temperatures of 80-100° C. with catalytic KI. When the protective group Q in 9 is Boc, treatment with HCl/dioxane furnishes hydrazine 10. Acylation of 10 with a carboxylic acid is effected, for example, with the acid and a carbodiimide, or with a preformed mixed anhydride, such as that with isopropyl chloroformate. Hydrazide 11 is cyclized to I. This cyclization can be accomplished with N,O-bis(trimethylsilyl)acetamide at 120° C., or other known cyclization methods can be used.

In certain cases, the initial R group may contain a protective group, such as trimethylsilyl for an acetylene or t-butyldimethylsilyl for an alcohol. The protective group may be removed following the conversion to a compound of formula I by employing well known methods.

An alternative route is illustrated in Scheme 2.

Scheme 2

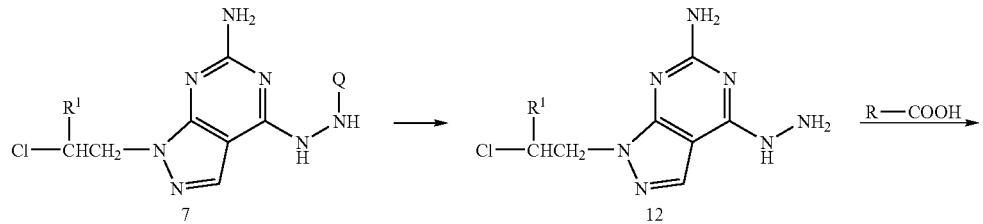

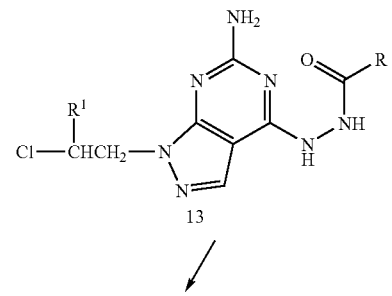

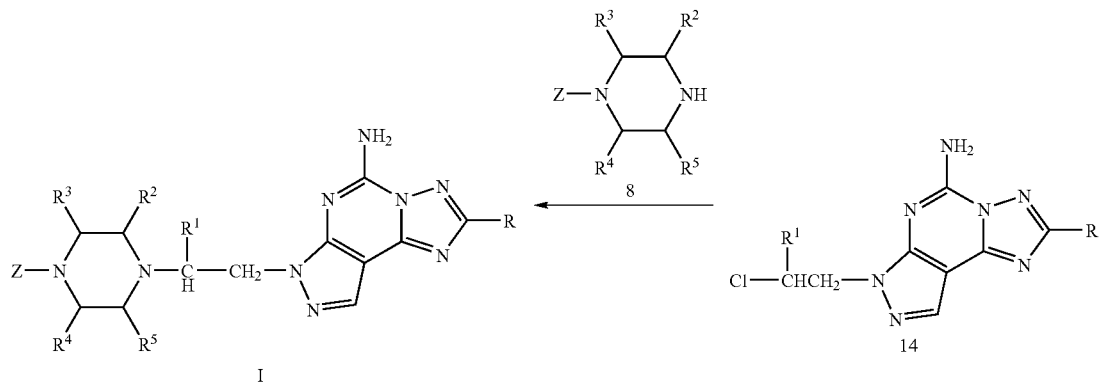

Compound 7 is deprotected as for 9, and 12 is acylated as for 10. Hydrazide 13 is cyclized as for 11. Amination of 14 to yield I takes place at temperatures of 100-160° C., preferably in DMF and in the presence of KI. Heating may also be effected by microwave irradiation in a sealed vessel yielding temperatures of 190-210° C.

Another method is illustrated in Scheme 3.

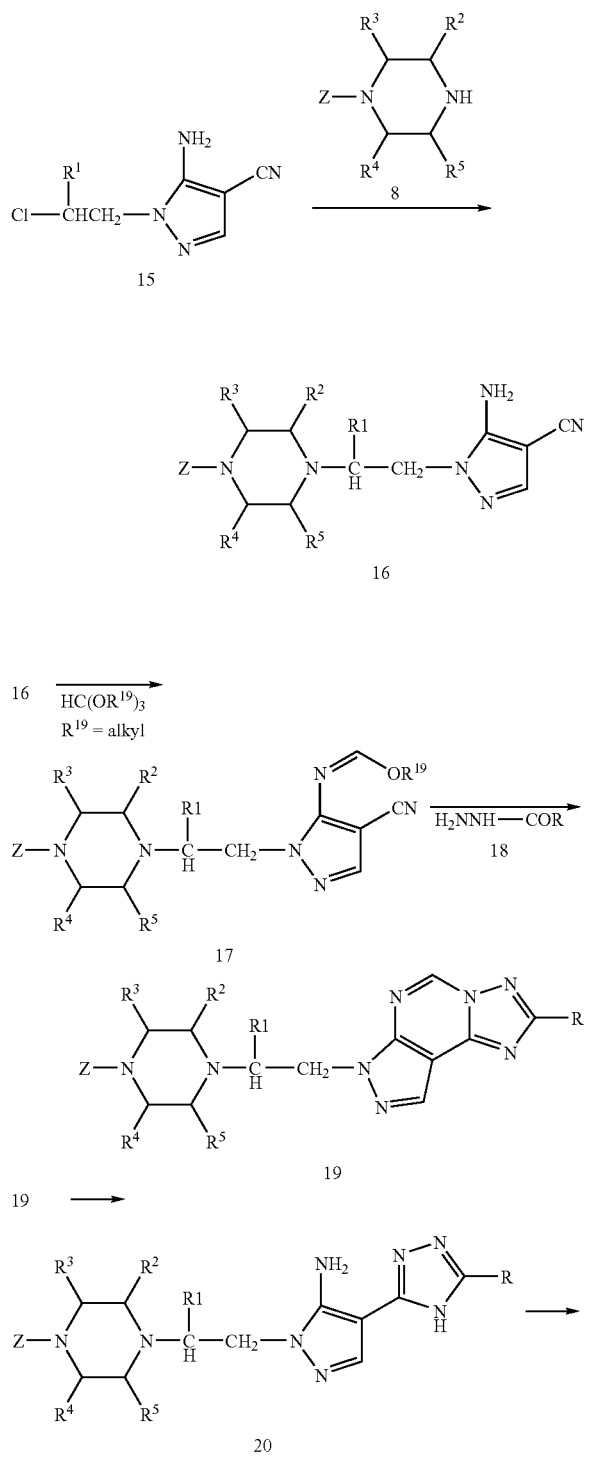

-continued

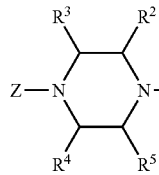

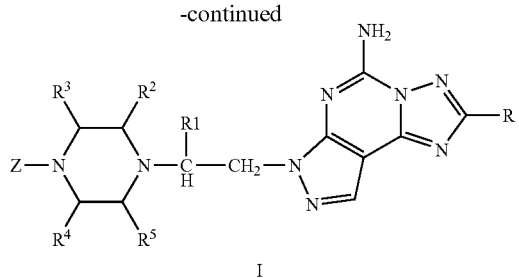

A hydroxyalkylpyrazole 15, prepared by methods well-known in the art, is aminated with 8. The amination involves activation of the alcohol with a reagent such as methanesulfonyl chloride or thionyl chloride and a base, typically an amine. Reaction of the activated alcohol with 8 provides piperazine 16. Reaction of 16 with a trialkyl orthoformate in the presence of an acid such as methanesulfonic acid provides 17. Heating 17 with hydrazide 18 in a solvent such as anisole in the presence of an acid such as isobutyric acid furnishes tricyclic 19. Treatment of 19 with aqueous acid, typically hydrochloric acid, provides amine 20. Cyclization of 20 with cyanogen bromide, preferably in the presence of a catalyst such as 4-dimethylaminopyridine and a solvent such as aqueous acetonitrile, yields I.

Another method is shown in Scheme 4:

Amination of 21 to yield I takes place at temperatures of 100-160° C., preferably in DMF and in the presence of KI. Heating may also be effected by microwave irradiation in a sealed vessel yielding temperatures of 190-210° C.

In the above schemes, one compound of formula I can be converted to a different compound of formula I by well-known methods, such as reduction of a ketone to an alcohol with NaBH$_4$.

Other synthetic routes applicable to the preparation of these materials are described in WO 01/92264, which is equivalent to U.S. Ser. No. 09/865,071, publication number 2002/0099061, incorporated herein by reference.

Abbreviations used in the specification are as follows: Me (methyl); Bu (butyl); Et (ethyl); Ac (acetyl); Boc (t-butoxycarbonyl); DMF (dimethylformamide); THF (tetrahydrofuran); DIPEA (diisopropylethylamine); RT (room temperature); BSA (N,O-bis(trimethylsilyl)-acetamide); BINAP (2,2'-bis(diphenylphosphino)-1,1'-binaphthyl); PLC (preparative layer chromatography); TFA (trifluoroacetic acid); HOBt (hydroxybenzotriazole); DAST (diethylaminosulfur trifluoride); EDCl (1-(3-dimethylaminopropyl)-3-ethyl-carbodiimide hydrochloride); Ms (methanesulfonate); TBAF (tetrabutylammonuim fluoride); and TBS (t-butyidimethylsilyl).

Preparation 1 tallize the residue from $CH_3CN$ to give the desired compound VIII. Mass spectrum: MH+=282.

Step 3: Add hydrazine hydrate (75 mg, 1.5 mmol) to a hot $CH_3CN$ solution of the product of Step 2 (0.14 g, 0.5 mmol). Reflux 1 h. Cool to RT and collect the yellow product IX. Mass spectrum: MH+=260.

Step 4: Heat the product of Step 3 (5.4 g, 0.021 mol) in a mixture of hexamethyl-disilazine (100 ml) and N,O-bis(trimethylsilyl) acetamide (35 ml) at 120° C. overnight. Remove volatiles under vacuum and slurry the residue in hot water to

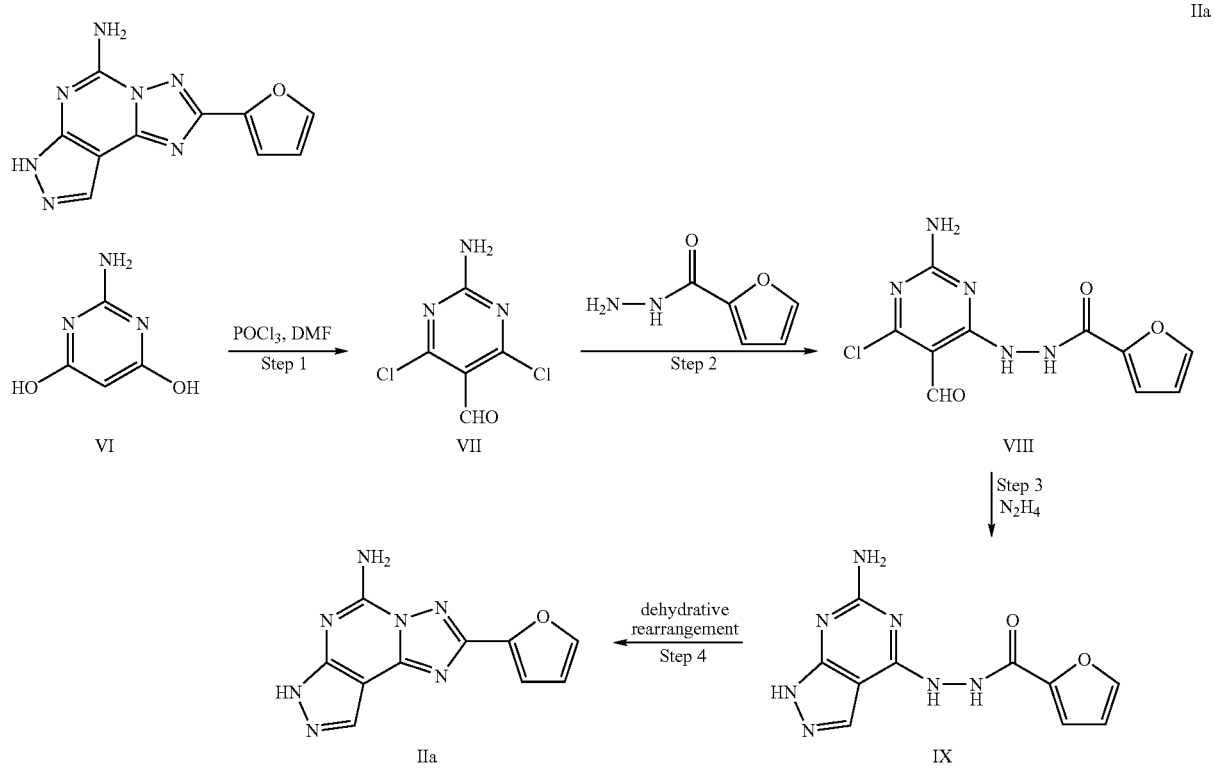

Step 1: Stir $POCl_3$ (84 ml, 0.9 mol) and chill to 5-10° C. while adding DMF (17.8 ml, 0.23 mol) drop-wise. Allow the mixture to warm to room temperature (RT) and add 2-amino-4,6-dihydroxypyrimidine VI (14 g, 0.11 mol) portion-wise. Heat at 100° C. for 5 h. Strip off excess $POCl_3$ under vacuum, pour the residue into ice water, and stir overnight. Collect solids by filtration and recrystallize the dried material from a filtered ethyl acetate (EtOAc) solution to give the aldehyde, VII, m.p. 230° (dec). Mass spectrum: M+=192. PMR (DMSO): δ 8.6 (δ, 2H); δ 10.1 (s, 1H).

Step 2: Stir a mixture of the product of Step 1 (0.38 g, 2 mmol) and 2-furoic hydrazide (0.31 g, 2.5 mmol) in $CH_3CN$ (50 ml) containing N,N-diisopropylethylamine (0.44 ml, 2.5 mmol) overnight at RT. Solvent strip the reaction mixture, and partition the residue between EtOAc and water. Dry the organic layer over $MgSO_4$, remove the solvent, and recrysgive a solid precipitate. Recrystallize from 80% aqueous acetic acid to give the title compound. M.P.>300° C. Mass spectrum: MH+=242.

Preparation 2

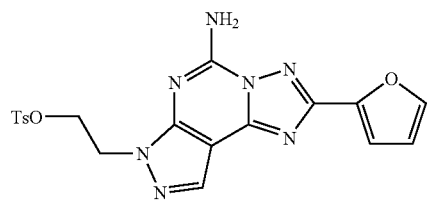

-continued

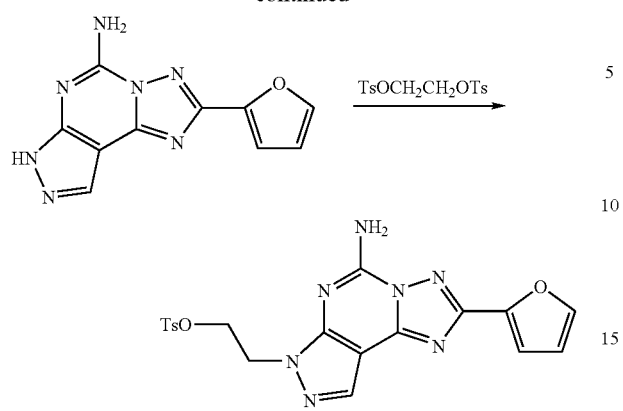

Combine the product of Preparation 1 (6.0 g, 25 mmol), ethylene glycol ditosylate (11.1 g, 30 mmol), and NaH (60% in oil, 1.19 g, 30 mmol) in dry DMF (30 ml). Stir under $N_2$ for 24 h and filter to obtain the title compound as a cream solid (PMR in DMSO: δ4.47+4.51 triplets, 8.03 s). Isolate additional material by chromatography of the filtrate.

Preparation 3

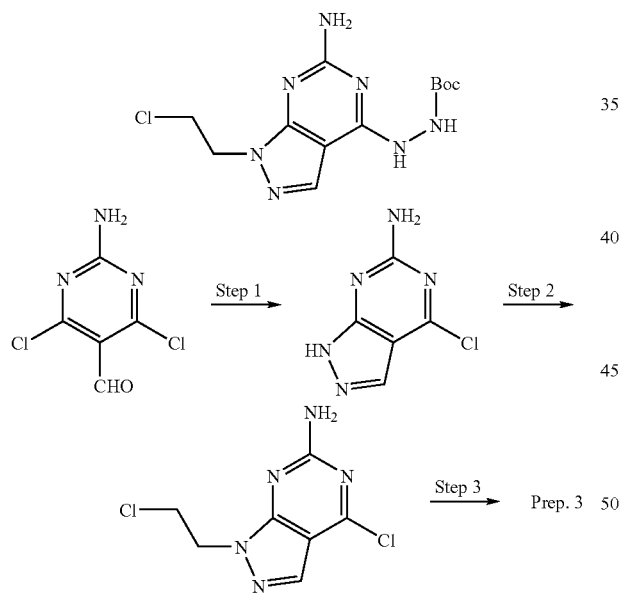

Step 1: To 2-amino-4,6-dichloropyrimidine-5-carboxaldehyde (25.0 g, 130 mmol) in DMF (100 ml) add DIPEA (28.4 ml, 163 mmol) and then hydrazine hydrate (6.32 ml, 130 mmol). After the initial exotherm, stir 24 h and concentrate in vacuo to ~50 g. Add water (50 ml), filter, wash with water, and dry to give the monochloride as a brown solid.

Step 2: To the product of Step 1 (15.0 g, 88 mmol) in DMF (150 ml) add 60% NaH in mineral oil (4.25 g, 106 mmol). Add slowly 1-bromo-2-chloroethane (22.1 ml, 265 mmol). Stir at RT 2 h, concentrate, and chromatograph on silica to obtain the dichloride as an off-white solid.

Step 3: Combine the product of Step 2 (12.2 g, 52.5 mmol) and t-butyl carbazate (8.33 g, 63 mmol) in DMF (70 ml). Heat at 80° C. 24 h, allow to cool, concentrate, and chromatograph on silica to obtain the title carbazate as a white solid.

Preparation 4

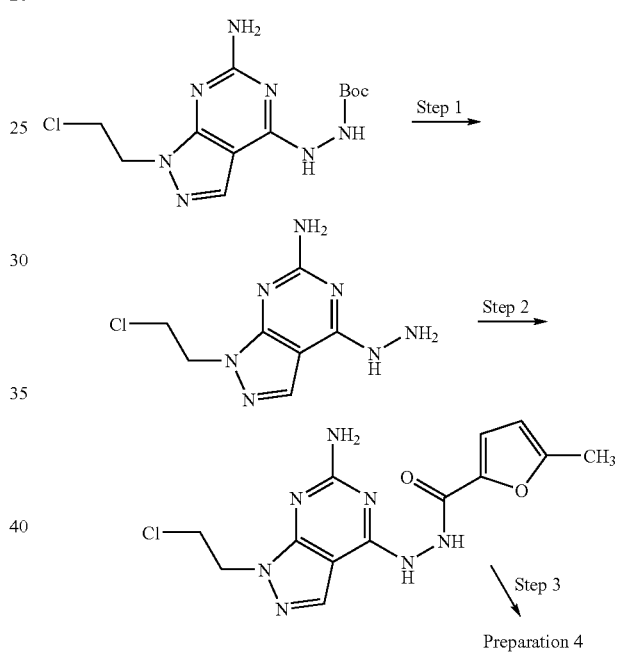

Step 1: Dissolve the product of Preparation 3 (5.0 g, 15 mmol) in 1:1 $CH_3OH$—$CH_2Cl_2$ (80 ml). Add 4.0M HCl/dioxane (20 ml, 80 mmol) and allow to stand 18 h. Basify with aq. $NH_3$ to pH 11, concentrate, treat with water (50 ml), filter, wash with water, and dry to obtain the hydrazine as a yellow solid.

Step 2: Combine the product of Step 2 (0.30 g, 1.32 mmol), 5-methylfuran-2-carboxylic acid (0.20 g, 1.6 mmol), EDCl (0.30 g, 1.6 mmol), HOBt.$H_2O$ (0.21 g, 1.6 mmol) and N-methylmorpholine (0.17 g, 1.6 mmol) in DMF (6 ml). Stir 1.5 h, concentrate, and purify by PLC to obtain the hydrazide as a yellow oil.

Step 3: Combine the product of Step 3 (0.68 g, 2.0 mmol) with BSA (6 ml). Heat at 120° C. 24 h and allow to cool. Concentrate and treat the residue with $CH_3OH$. Purify by PLC to obtain the title compound as a white solid.

In a similar fashion, employ the appropriate carboxylic acids to obtain Preparations 4-2 to 4-20:

Prep. 4-2
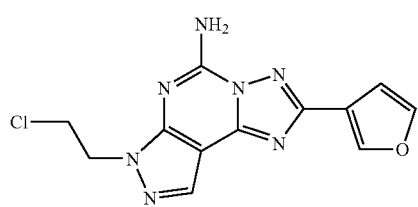
Prep. 4-3
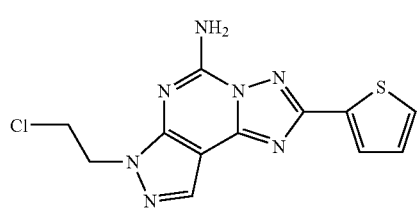
Prep. 4-4
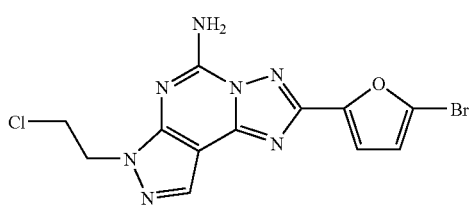
Prep. 4-5
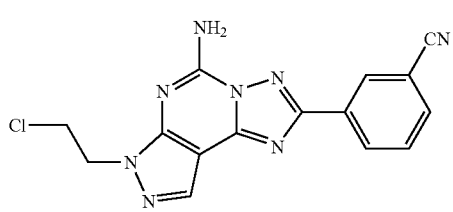
Prep. 4-6
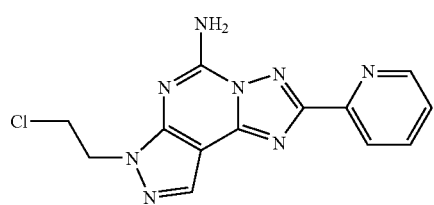
Prep. 4-7
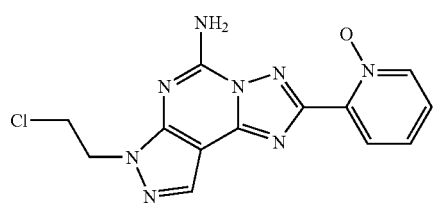
Prep. 4-8
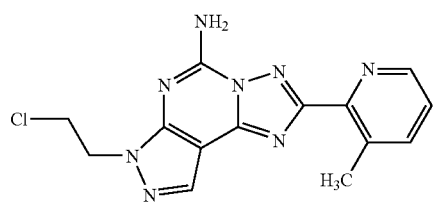
-continued
Prep. 4-9
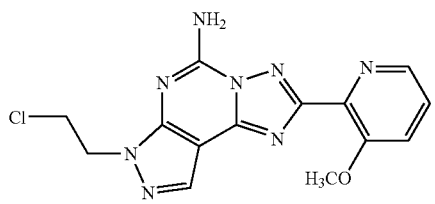
Prep. 4-10
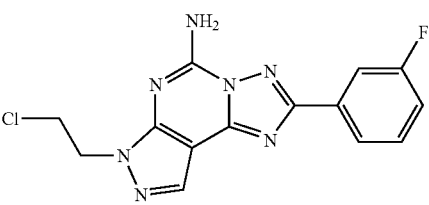
Prep. 4-11
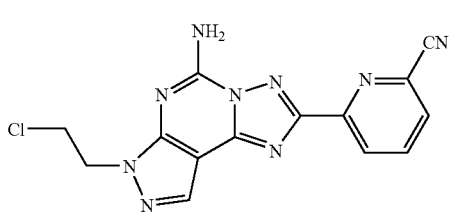
Prep. 4-12
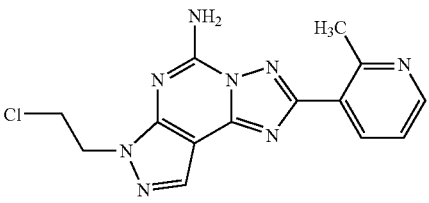
Prep. 4-13
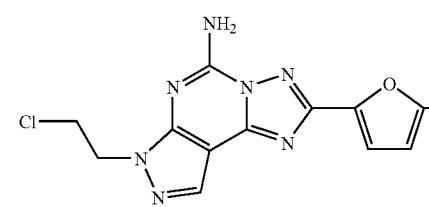
Prep. 4-14
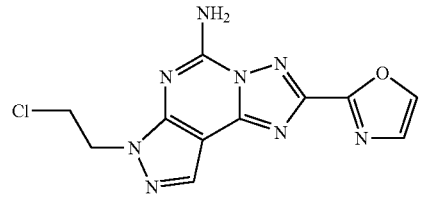
Prep. 4-15
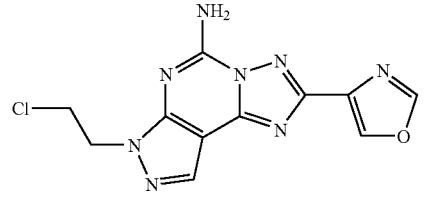

-continued

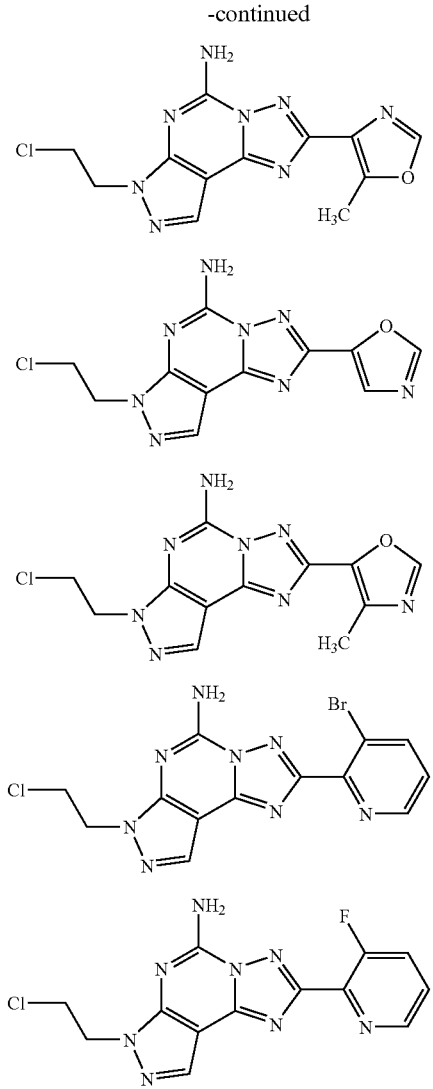

Preparation 5

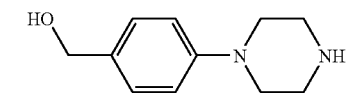

Combine 4-bromobenzyl alcohol (2.00 g, 10.7 mmol), piperazine (5.52 g, 64 mmol), NaO-tBu (1.44 g, 15.0 mmol), ±-BINAP (0.40 g, 0.64 mmol), and Pd$_2$(dba)$_3$ (0.12 g, 0.21 mmol) in toluene (15 ml). Heat at 100° C. 18 h, stirring under nitrogen. Allow to cool and extract with 2N HCl. Basify the aqueous with NaOH to pH=14 and extract with CH$_2$Cl$_2$. Dry over MgSO$_4$, concentrate, and chromatograph over silica to obtain the piperazine as a yellow solid.

In similar fashion, obtain Preparations 5-2, 5-3, 5-4, and 5-5. For Preparation 5-6, employ Cs$_2$CO$_3$ in place of NaO-tBu and dioxane as solvent. For Preparation 5-7, employ the chloropyridine, with Cs$_2$CO$_3$ in place of NaO-tBu and DMSO as solvent. From the bromo-pyridine with K$_2$CO$_3$ in DMSO obtain Preparation 5-8. Produce Preparation 5-9, a light green solid, and Preparation 5-10, a yellow oil, as for Preparation 5.

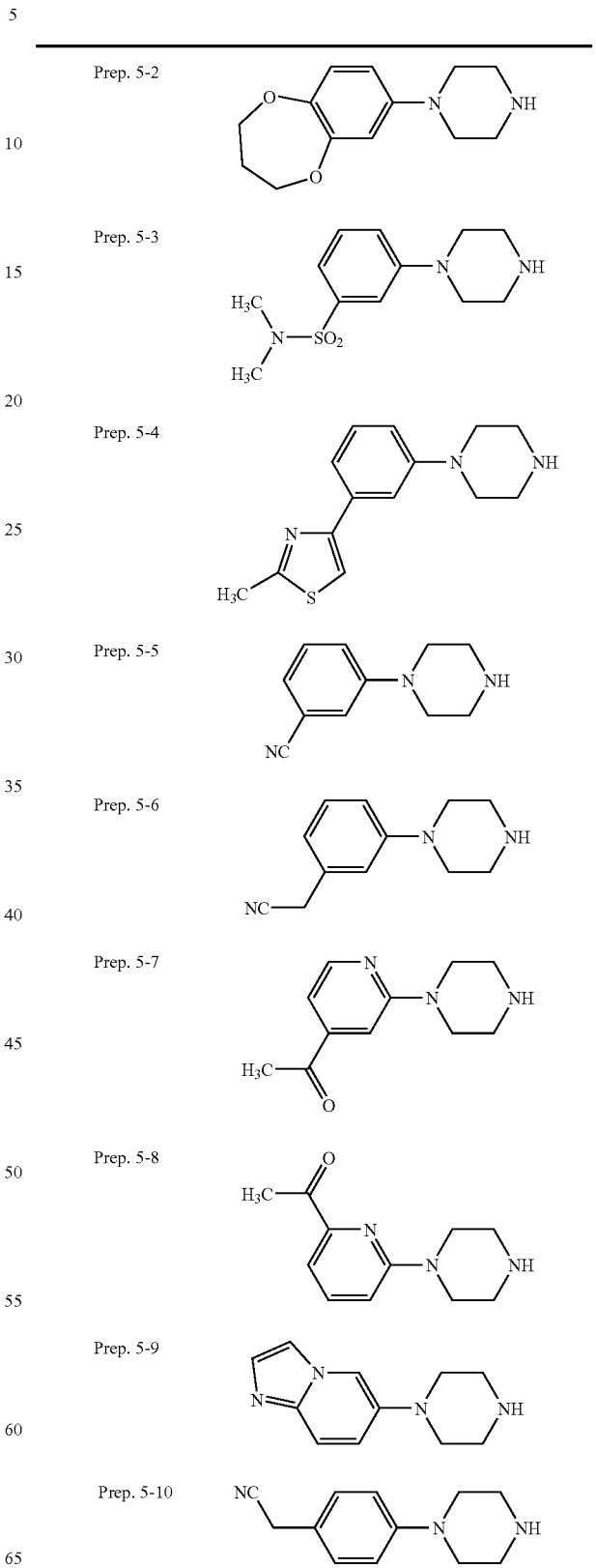

Preparation 6

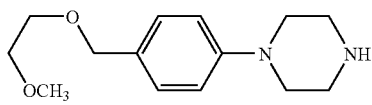

React 2-methoxyethyl-(4-bromophenylmethyl)ether (prepared by reaction of 4-bromobenzyl bromide and 2-methoxyethanol with sodium hydride in DMF) with piperazine according to Preparation 5. Chromatograph the crude product over silica to obtain the title piperazine as a yellow oil.

In similar fashion produce Preparation 6-2.

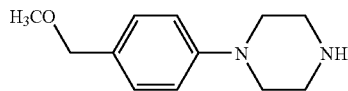

Preparation 7

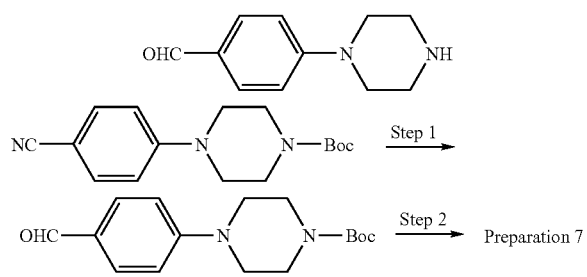

Step 1: To t-butyl 4-(4-cyanophenyl)piperazine-1-carboxylate (2.30 g, 8.0 mmol, prepared by reaction of the arylpiperazine with Boc-anhydride) in toluene (20 ml) add DIBAH (diisobutylaluminum hydride) (1.0M in toluene, 12.8 ml, 12.8 mmol). Heat at 50° C. 1.5 h, allow to cool, add MeOH (10 ml) and water (10 ml). Filter and concentrate. Chromatograph the residue over silica to obtain the Boc-piperazine as a yellow solid.

Step 2: To the product of Step 1 0.50 g, 1.7 mmol) in CH$_2$Cl$_2$ (5 ml) add TFA (5.0 ml). Stir 0.75 h and concentrate to obtain the TFA salt of Preparation 7 as a red oil.

Preparation 8

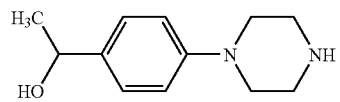

To 1-(4-acetylphenyl)piperazine (1.00 g, 4.9 mmol) in EtOH (15 ml) add NaBH$_4$ (0.93 g, 25 mmol). Heat at reflux 4 h, allow to cool, and add 0.5N NaOH (20 ml). Extract with CH$_2$Cl$_2$, dry over MgSO$_4$, concentrate, and chromatograph over silica to obtain the title alcohol as a white solid.

Preparation 9

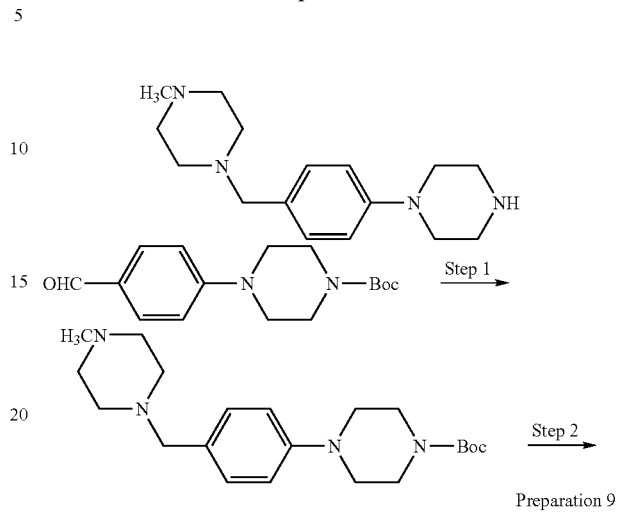

Step 1: To the product of Preparation 7, Step 1 (0.43 g, 1.5 mmol) in CH$_2$Cl$_2$ (10 ml) add 1-methylpiperazine (0.81 ml, 7.4 mmol) and HOAc (0.5 ml). Add NaCNBH$_3$ (0.46 g, 7.4 mmol) and heat 40° C. 3 h. Allow to cool, and add 0.5N NaOH (20 ml). Extract with CH$_2$Cl$_2$, dry over MgSO$_4$, concentrate, and chromatograph over silica to obtain the amine as a white solid.

Step 2: Deprotect the product of Step 1 according to Preparation 7, Step 2. Treat the TFA salt with 1.0N NaOH and extract with CH$_2$Cl$_2$. Dry over MgSO$_4$ and concentrate to obtain the title piperazine as a yellow oil.

Preparation 10

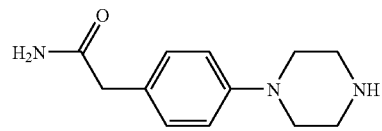

To the product of Preparation 5-10 (0.26 g, 1.3 mmol) in TFA (5 ml) add HCl (4M in dioxane, 5.0 ml, 20 mmol), then water (0.04 ml). Stir at 50° C. 2 h, add water (5 ml), stir 1 h, and concentrate. Basify with methanolic NH$_3$ and purify by PLC to obtain the title piperazine as a yellow solid.

Preparation 11

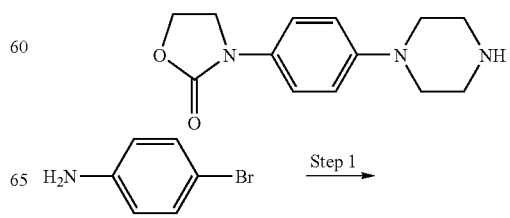

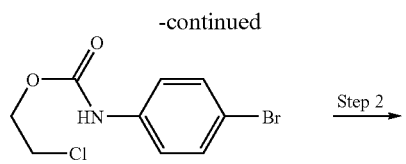

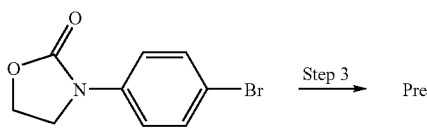

Step 1: To 4-bromoaniline (4.30 g, 25 mmol) in ether (15 ml) add Et₃N (2.70 g, 27 mmol). Add dropwise, with ice-bath cooling, 2-chloroethyl chloroformate (3.82 g, 27 mmol) in ether (10 ml). Stir 0.5 h and filter. Wash the ether with 1N HCl, then brine. Dry (MgSO₄) and concentrate to leave a solid. Heat in hexane, allow to cool, and collect the carbamate as a cream solid.

Step 2: Add the product of Step 1 (4.19 g, 15 mmol) to a solution of KOH (1.19 g, 85%, 18 mmol) EtOH (28 ml) and water (12 ml) cooled in an ice bath. Replace with a water bath, stir 1.5 h, concentrate, and dilute with water (10 ml). Filter to obtain the title compound as a cream solid.

Step 3: Convert the product of Step 2 to the title aryl-piperazine, a yellow solid, following the procedure of Preparation 5.

Preparation 12

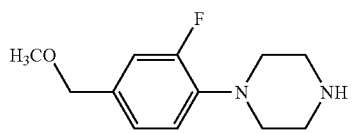

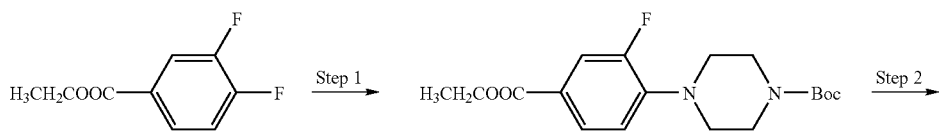

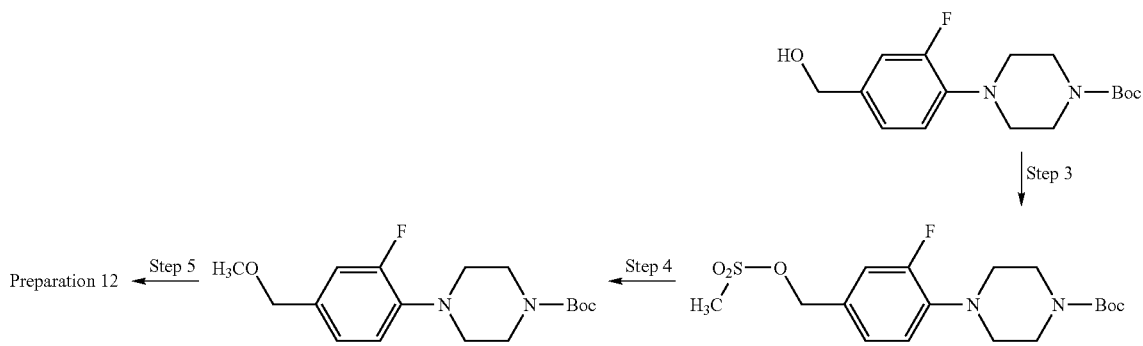

Step 1: Combine ethyl 3,4-difluorobenzoate (2.00 g, 10.7 mmol), t-butyl piperazine-1-carboxylate (2.20 g, 11.8 mmol), and K₂CO₃ (1.80 g, 13.1 mmol) in DMF (10 ml). Heat at 100° C. 72 h and allow to cool. Concentrate and chromatograph on silica to obtain the aryl-piperazine as a yellow oil.

Step 2: Cool to 0° C. a solution of the product of Step 1 (3.1 g, 8.8 mmol) in THF (20 ml). Add dropwise LiAlH₄ (1.0M in THF, 5.3 ml, 5.3 mmol). Stir at 0° C. 2 h. Add ice-water and citric acid (3.0 g). Extract with ether, dry (MgSO₄) and concentrate to obtain the alcohol as a yellow oil.

Step 3: To a solution of the product of Step 2 (1.47 g, 4.8 mmol) in CH₂Cl₂ (20 ml) at 0° C. add Et₃N (0.80 ml, 5.7 mmol) and then MsCl (0.65 g, 5.7 mmol). Stir at 0° C. 2 h, then RT 1 h. Concentrate to obtain the crude mesylate.

Step 4: Dissolve all of the of crude mesylate from Step 2 in MeOH (20 ml). Add NaOMe (0.77 g, 14.2 mmol). Heat at 60° C. 1.5 h, allow to cool, and dilute with water (30 ml). Extract with ether, dry (MgSO₄) and concentrate to obtain the methyl ether as a yellow oil.

Step 5: Dissolve the product of Step 4 (1.00 g, 3.1 mmol) in CH₂Cl₂ (4 ml), cool to 0° C., and add slowly TFA (20 ml). Stir at 0° C. 2.5 h, concentrate, and partition between CH₂Cl₂ and 1N NaOH. Dry (MgSO₄) and concentrate to obtain the title compound as a yellow oil.

Preparation 13

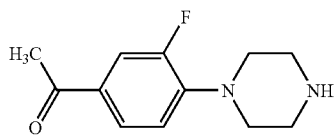

Combine 3,4-difluoroacetophenone (2.00 g, 12.8 mmol), piperazine (5.52 g, 64 mmol), and K₂CO₃ (2.12 g, 15.4 mmol) in toluene (20 ml). Heat at 110° C. 20 h and allow to cool. Basify with NaOH to pH 13. Extract with CH₂Cl₂, wash with water, dry (MgSO₄) and concentrate to obtain the title compound as a yellow solid.

In similar fashion, from 2',4'-difluoroacetophenone, produce Preparation 13-2, a yellow oil; from 5-fluoro-1-indanone, produce Preparation 13-3, a yellow solid; and from 2'-methoxy-4'-fluoroacetophenone, produce Preparation 13-4, a yellow solid. From 2-chlorobenzoxazole with Et₃N in CH₂Cl₂, produce Preparation 13-5, a white solid. From 2',4'-difluorobenzaldehyde, produce Preparation 13-6.

Prep. 13-2

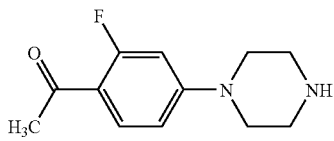

Prep. 13-3

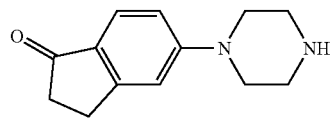

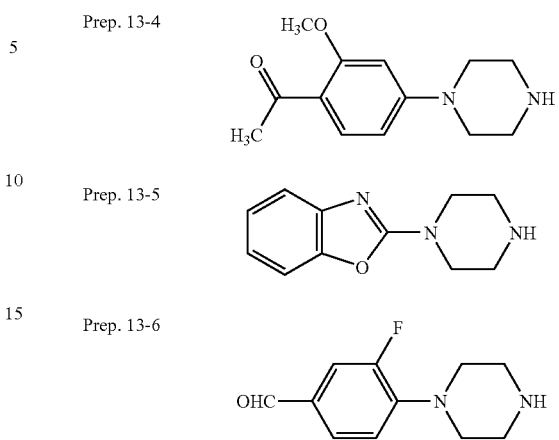

Preparation 14

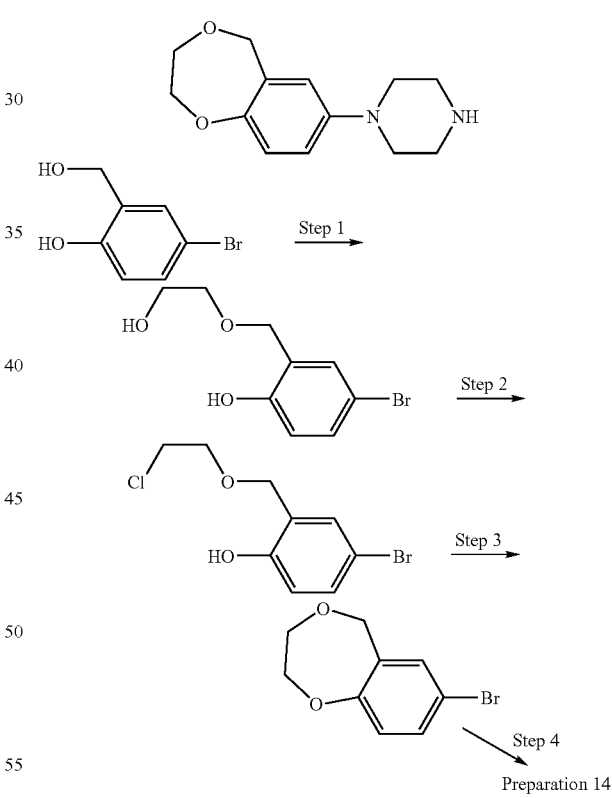

Step 1: Combine 5-bromo-2-hydroxybenzyl alcohol (3.00 g, 14.8 mmol) and TsOH.H₂O in ethylene glycol (15 ml). Heat at 80° C. 3 h, allow to cool, and partition between water and EtOAc. Wash with water, then brine, dry (MgSO₄) and concentrate to obtain the benzyl ether as a yellow oil.

Step 2: Cool to 0° C. a solution of the product of Step 1 (3.52 g, 14.3 mmol) in CH₂Cl₂ (25 ml). Add pyridine (1.73 ml, 21 mmol), followed by SOCl₂ (1.14 ml, 15.7 mmol).

Allow to warm to RT, stir 3 h, add pyridine (1.73 ml) and SOCl$_2$ (1.14 ml), and stir 20 h. Wash with water, dry (MgSO$_4$) and concentrate. Chromatograph on silica to obtain the chloride as a yellow oil.

Step 3: Combine the product of Step 2 (2.64 g, 9.9 mmol), K$_2$CO$_3$ (1.65 g, 11.9 mmol) and KI (0.83 g, 5.0 mmol) in DMF (25 ml). Stir 120 h and concentrate. Partition between CH$_2$Cl$_2$ and water, wash with water and then brine, and dry (MgSO$_4$). Concentrate to obtain the benzodioxepine as a yellow oil.

Step 4: Convert the product of Step 3 to the aryl-piperazine, a light brown oil, following the procedure of Preparation 5.

For Preparation 14-2, brominate and reduce ethyl 4-fluorosalicylate according to the procedures of Preparation 48, Steps 2 and 3. Continue analogously to Preparation 14 to obtain the aryl-piperazine as a yellow solid.

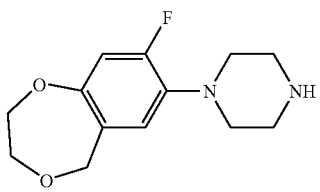

For Preparation 14-3, reduce 4-bromosalicylic acid according to Preparation 48, Step 3, and continue analogously to obtain the aryl-piperazine as a yellow oil.

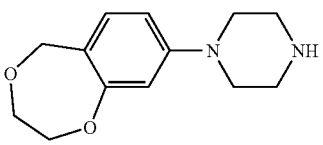

Preparation 15

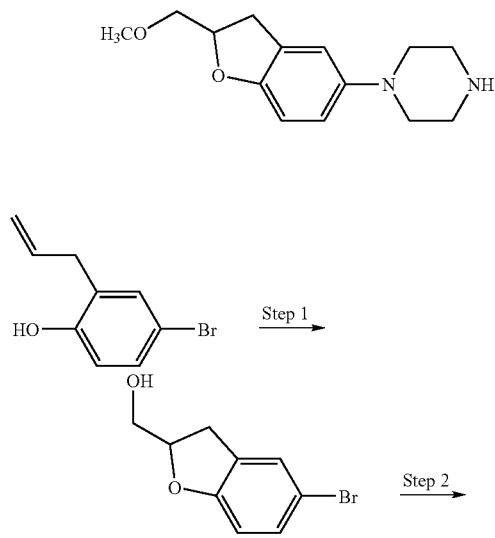

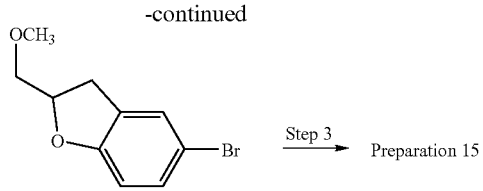

Step 1: To 2-allyl-4-bromophenol (3.13 g, 14.6 mmol) in 1,2-dichloroethane (250 ml) add m-chloroperbenzoic acid (70%, 3.59 g, 14.5 mmol). Heat to 70° C., stir 4 h, and add more peracid (2.50 g). Heat an additional 2 h, allow to cool, concentrate, and partition with ether and 1N NaOH. Dry (MgSO$_4$) and concentrate to obtain the alcohol as a yellow oil.

Step 2: To the product of Step 1 (2.40 g, 10.5 mmol) in DMF (20 ml) add NaH (60% in oil, 0.59 g, 14.8 mmol). Stir 15 min, cool to 0° C., and add CH$_3$I (1.78 g, 12.5 mmol). Stir 2 h, allow to warm, and partition with ether and 0.5N NaOH. Dry (MgSO$_4$) and concentrate to obtain the methyl ether as a yellow oil containing a small amount of mineral oil.

Step 3: Convert the product of Step 2 to the title compound, a yellow oil, following the procedure of Preparation 5.

Similarly, convert the product of Step 1 to the TBS ether according to Preparation 34, Step 1, and react with piperazine according to the procedure of Preparation 5 to obtain Preparation 15-2 as a yellow oil.

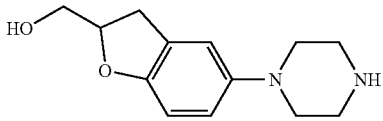

Preparation 16

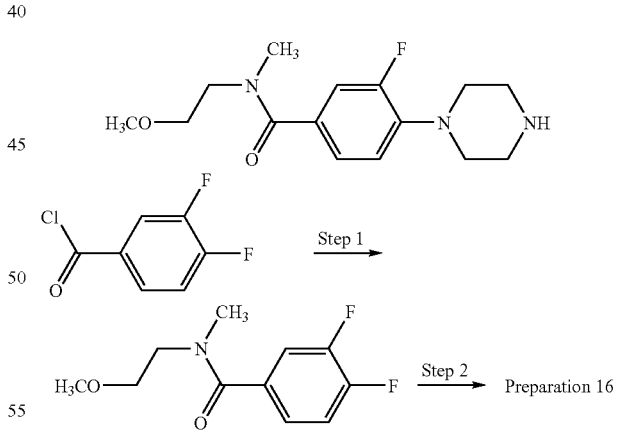

Step 1: Combine 3,4-difluorobenzoyl chloride (1.01 g, 5.7 mmol) and Et$_3$N (0.57 g, 5.6 mmol) in EtOAc (10 ml) and cool to 0° C. Add dropwise N-(2-methoxyethyl)-methylamine (0.62 g, 7.2 mmol), stir 0.5 h, allow to warm, and wash with 1N HCl, then 1N NaHCO$_3$. Dry (MgSO$_4$) and concentrate to obtain the amide as a yellow oil.

Step 2: Combine the product of Step 1 (1.20 g, 5.2 mmol), piperazine (2.24 g, 26 mmol) and K$_2$CO$_3$ in dry DMF (10 ml). Heat at 120° C. under N$_2$ 20 h and allow to cool. Dilute with EtOAc, filter, and concentrate. Partition with EtOAc and 1N HCl. Basify the aqueous layer with Na₂CO₃, add NaCl (5 g), and extract with EtOAc/EtOH (9:1). Dry (MgSO₄) and concentrate to obtain the title compound as a thick yellow oil.
In similar fashion, from the appropriate amines, produce Preparations 16-2 to 16-5.
Prep. 16-2
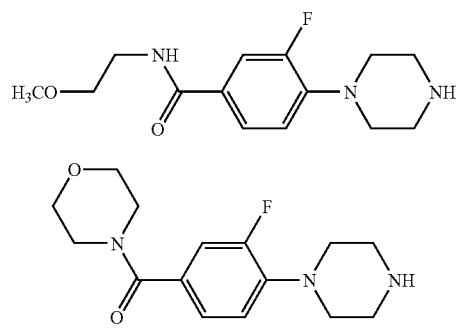
Prep. 16-3
Prep. 16-4
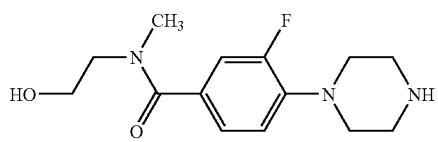
Prep. 16-5
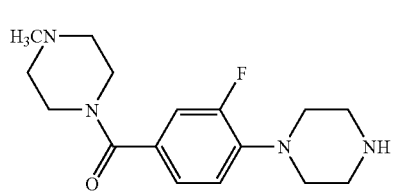
Preparation 17
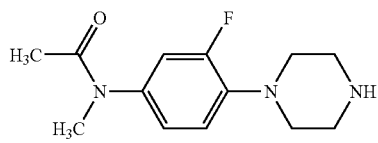
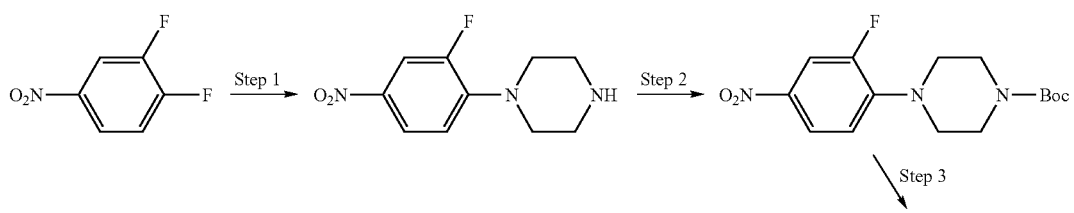
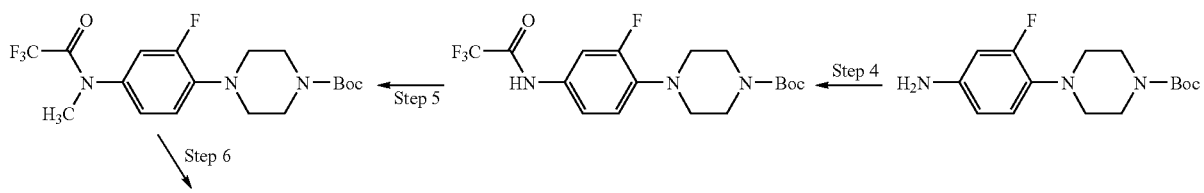
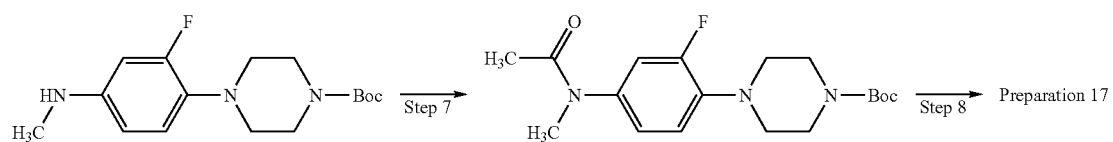

Step 1: Combine 3,4-difluoronitrobenzene (4.00 g, 25 mmol), piperazine (10.8 g, 125 mmol), and $K_2CO_3$ (4.17 g, 30 mmol) in toluene (30 ml). Heat at reflux 24 h, allow to cool, and extract with 1N HCl. Basify the aqueous with NaOH to pH 13 and extract with $CH_2Cl_2$. Wash with brine, dry ($MgSO_4$) and concentrate to obtain the aryl-piperazine as a yellow solid.

Step 2: To the product of Step 1 (1.51 g, 6.7 mmol) in $CH_2Cl_2$ (20 ml) add $Et_3N$ (1.12 ml, 8.1 mmol), followed by $Boc_2O$ (1.47 g, 6.7 mmol). Stir 1 h and wash with satd. $NaHCO_3$, then brine. Dry ($MgSO_4$) and concentrate to obtain the carbamate as a yellow solid.

Step 3: Dissolve the product of Step 2 (2.18 g, 6.7 mmol) in 1:1 $CH_3OH$/EtOAc (40 ml) and add 5% Pd/C (0.50 g). Hydrogenate at 55 psi 1.5 h, filter through Celite and concentrate to obtain the arylamine as a brown oil.

Step 8: Dissolve the product of Step 7 (0.90 g, 2.5 mmol) in $CH_2Cl_2$ (10 ml). Add TFA (6.0 ml). Stir 1 h, concentrate, and partition with $CH_2Cl_2$ and 1N NaOH. Wash with brine, dry ($MgSO_4$) and concentrate to obtain the title compound as a yellow oil.

In a similar fashion, but employing ethyl chloroformate in Step 7, prepare Preparation 17-2 as a yellow oil:

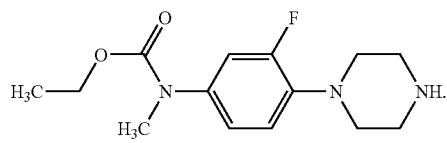

Preparation 18

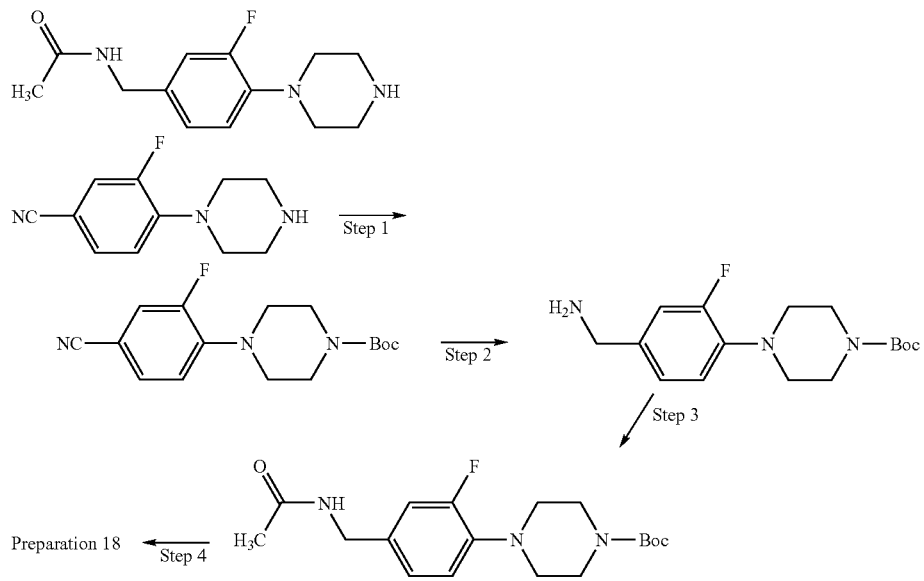

Step 4: To the product of Step 3 (1.00 g, 3.3 mmol) and DIPEA (0.88 ml, 5.1 mmol) in $CH_2Cl_2$ (15 ml) add trifluoroacetic anhydride (0.57 ml, 4.1 mmol). Stir 2 h and add a second portion each of DIPEA and anhydride. Stir 1 h and wash with satd. $NaHCO_3$, then water. Dry ($MgSO_4$) and concentrate to obtain the amide as a yellow solid.

Step 5: Combine the product of Step 4 (0.70 g, 1.8 mmol) and $K_2CO_3$ (0.37 g, 1.27 mmol) in dry DMF (8 ml). Add $CH_3I$ (0.12 ml, 2.0 mmol), stir 18 h, then heat at 60° C. 2 h. Concentrate and partition with ether and water. Wash with brine, dry ($MgSO_4$) and concentrate to obtain the methylamide as a yellow oil.

Step 6: Dissolve the product of Step 5 (1.01 g, 2.5 mmol) in $CH_3OH$ (5 ml). Add $K_2CO_3$ (0.34 g, 2.5 mmol) in water (3.5 ml). Stir 1 h, concentrate, and partition with $CH_2Cl_2$ and water. Wash with brine, dry ($MgSO_4$) and concentrate to obtain the amine as a yellow solid.

Step 7: To the product of Step 6 (0.77 g, 2.5 mmol) and DIPEA (0.65 ml, 3.7 mmol) in $CH_2Cl_2$ (10 ml) add AcCl (0.22 ml, 3.0 mmol). Stir 1 h, concentrate, and partition with $CH_2Cl_2$ and water. Wash with brine, dry ($MgSO_4$) and concentrate to obtain the amide as a yellow oil.

Step 1: Combine 1-(4-cyano-2-fluorophenyl)piperazine (1.57 g, 7.6 mmol) and $Et_3N$ (1.28 ml, 9.2 mmol) in $CH_2Cl_2$ (10 ml) and add $Boc_2O$ (1.67 g, 7.6 mmol). Stir 1 h wash with satd. $NaHCO_3$. Dry ($MgSO_4$) and concentrate to obtain the crude carbamate as a yellow solid.

Step 2: Dissolve the product of Step 1 (2.73 g, 8.9 mmol) in $CH_3OH$ (30 ml). Add HOAC (2.6 ml) and then $PtO_2$ (0.60 g). Hydrogenate at 60 psi for 18 h. Filter through Celite and add 1N NaOH (6 ml). Concentrate and partition with $CH_2Cl_2$ and water. Wash with brine, dry ($MgSO_4$) and concentrate to obtain the amine as a colorless oil.

Step 3: Combine the product of Step 2 (1.25 g, 4.0 mmol) and DIPEA (1.06 ml, 6.1 mmol) in $CH_2Cl_2$ (5 ml). Add AcCl (0.35 ml, 4.8 mmol). Stir 1 h, concentrate, and partition with $CH_2Cl_2$ and water. Wash with brine, dry ($MgSO_4$) and concentrate to obtain the amide as a yellow oil.

Step 4: Dissolve the product of Step 3 (1.38 g, 3.9 mmol) in $CH_2Cl_2$ (1 ml). Add TFA (8.0 ml). Stir 0.5 h, concentrate, and partition with $CH_2Cl_2$ and 1N NaOH, saturated with NaCl. Dry ($MgSO_4$) and concentrate. Purify by PLC to obtain the piperazine as a yellow oil.

In a similar manner, employ ethyl chloroformate in Step 3 to produce Preparation 18-2 as a yellow oil:

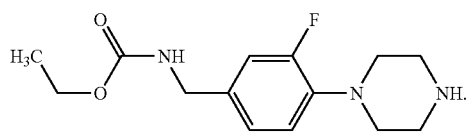

Preparation 19

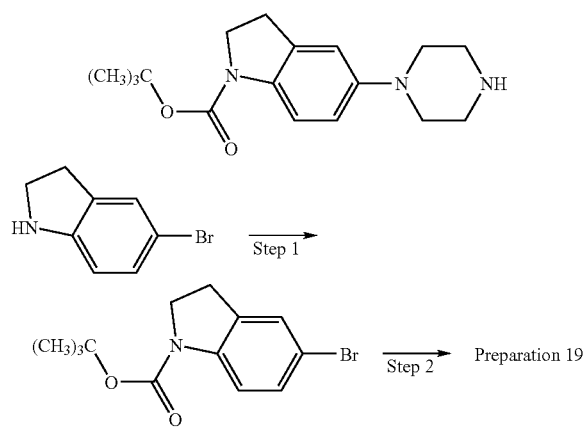

Step 1: Combine 5-bromoindoline (3.56 g, 18 mmol) and Et₃N (1.92 g, 19 mmol) in CH₂Cl₂ (40 ml). Cool in an ice bath and add Boc₂O (4.14 g, 19 mmol). Allow to warm, stir 2 h and add more Boc₂O (0.50 g). Stir 2 h and wash with 1N HCl, then with 1N NaHCO₃. Dry (MgSO₄) and concentrate. Heat the solid with hexane, allow to cool, and filter to obtain the carbamate as off-white crystals, m.p. 124-6° C.

Step 2: Convert the product of Step 1 to the title compound, a yellow oil, following the procedure of Preparation 5.

Preparation 20

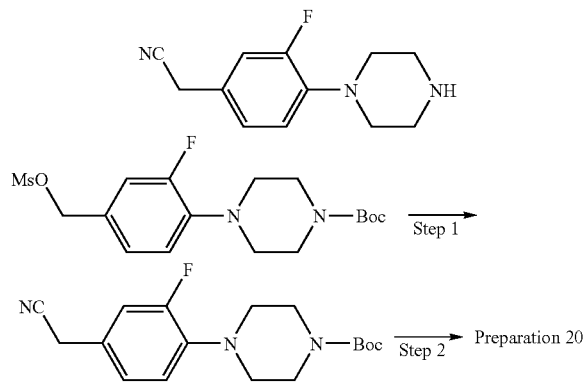

Step 1: To a solution of the product of Preparation 12, Step 3 (from 1.40 g, 45 mmol of starting alcohol) in CH₃OH, add KCN (1.03 g, 15.8 mmol). Heat at 60° C. 1 h, allow to cool, and partition with ether and 0.5N NaOH. Dry (MgSO₄), concentrate, and chromatograph on silica to obtain the nitrile as a yellow oil.

Step 2: Dissolve the product of Step 1 (0.63 g, 2.0 mmol) in CH₂Cl₂ (2 ml) and cool to 0° C. Add TFA (10 ml). Stir 2 h, concentrate, and basify with 7N methanolic NH₃. Concentrate and purify by PLC to obtain the title compound as a yellow solid.

Preparation 21

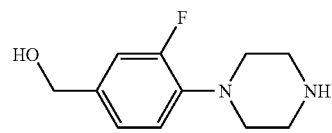

Remove the Boc group from the product of Preparation 12, Step 2 according to the procedure of Preparation 9, Step 2, to obtain the title compound as a yellow oil.

Preparation 22

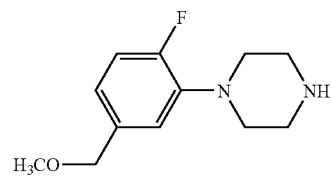

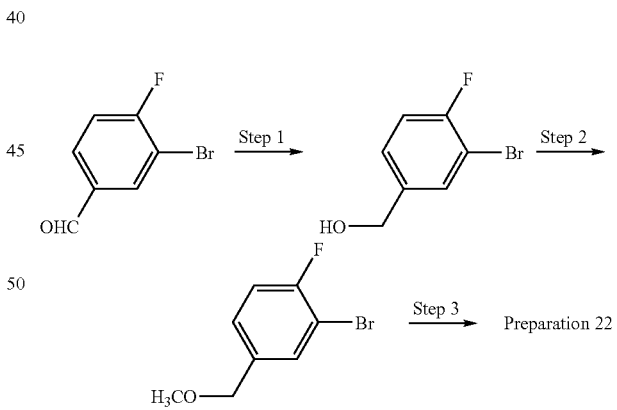

Step 1: To a solution of 3-bromo-4-fluorobenzaldehyde (1.20 g, 5.9 mmol) in EtOH (20 ml) add NaBH₄ (0.103 g, 2.7 mmol). Stir 2 h, concentrate, and partition between ether and water, with NH₄Cl (0.6 g) added. Dry (MgSO₄) and concentrate to obtain the alcohol as a colorless oil.

Step 2: Cool a solution of the product of Step 1 (1.20 g, 5.9 mmol) in THF (50 ml) in ice and add NaH (60% in oil, 0.33 g, 8.2 mmol), then CH₃I (1.00 ml, 7.1 mmol). Stir 3 h and partition between ether and water. Dry (MgSO₄) and concentrate to obtain the crude methyl ether as a yellow oil.

Step 3: Treat the product of Step 2 with piperazine according to Preparation 5 to obtain the aryl-piperazine as a yellow oil.

Preparation 23

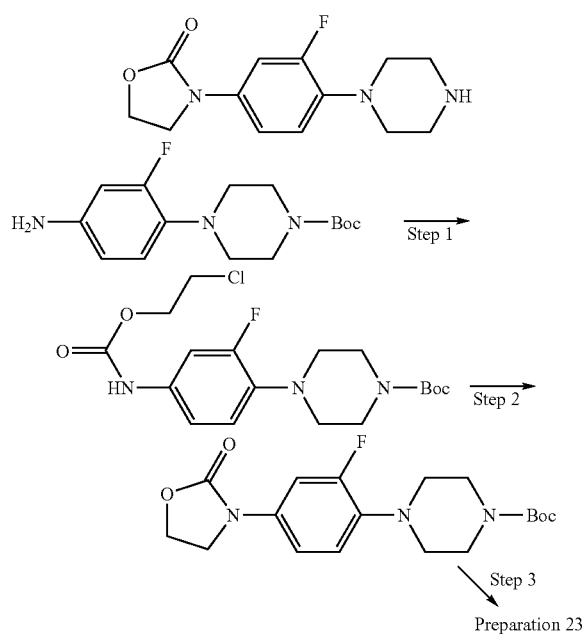

Preparation 23

Step 1: Cool in ice a solution of the product of Preparation 17, Step 3 (1.50 g, 5.1 mmol) in THF (40 ml). Add DIPEA (1.08 ml, 6.2 mmol), then 2-chloroethyl chloroformate (0.76 g, 5.3 mmol). Stir 3 h and partition with ether and satd. NaHCO₃. Dry (MgSO₄) and concentrate to obtain the carbamate as a brown solid.

Step 2: Dissolve the product of Step 1 (2.05 g, 5.1 mmol) in THF (150 ml). Add NaH (60% in oil, 0.25 g, 6.1 mmol). Heat at 60° C. 18 h, allow to cool, and partition with ether and water. Dry (MgSO₄) and concentrate to obtain the crude oxazolinone as a yellow solid.

Step 3: Remove the Boc group from the product of Step 2 according to the procedure of Preparation 9, Step 2, to obtain the crude title compound as a yellow solid.

Employing Steps 1 and 3 in similar fashion with acetyl chloride and methanesulfonyl chloride, produce Preparations 23-2 and 23-3.

Prep. 23-2

Prep. 23-3

Preparation 24

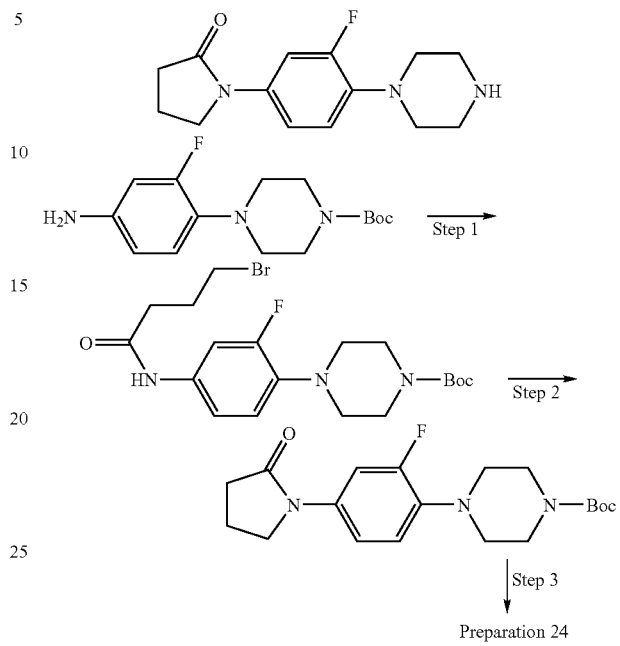

Preparation 24

Step 1: Cool in ice a solution of the product of Preparation 17, Step 3 (1.53 g, 5.2 mmol) and DIPEA (1.10 ml, 6.2 mmol) in THF (40 ml). Add dropwise 4-bromobutyryl chloride (1.01 g, 5.4 mmol). Stir 2 h and partition with ether and satd. NaHCO₃. Dry (MgSO₄) and concentrate to obtain the carbamate as a yellow solid.

Step 2: Dissolve the product of Step 1 (2.30 g, 5.2 mmol) in DMF (100 ml). Add NaH (60% in oil, 0.25 g, 6.1 mmol). Heat at 90° C. 18 h, allow to cool, concentrate, and partition with ether and water. Dry (MgSO₄) and concentrate to obtain the crude lactam as a yellow solid.

Step 3: Remove the Boc group from the product of Step 2 according to the procedure of Preparation 9, Step 2, to obtain the crude title compound as a yellow solid.

Preparation 25

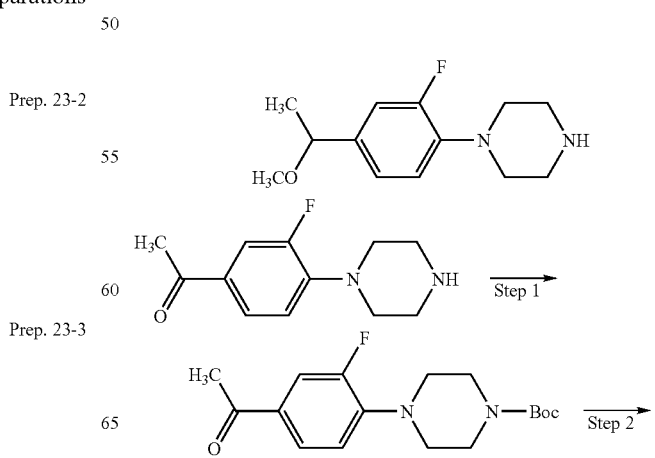

-continued

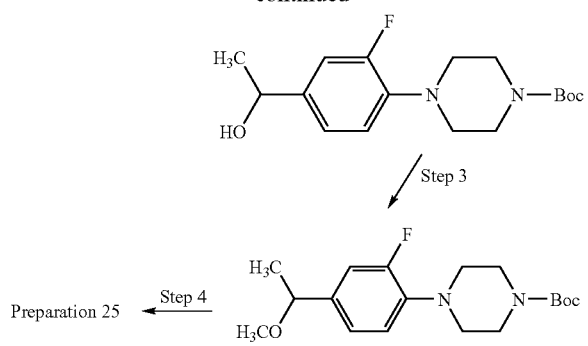

Step 1: Convert the product of Preparation 13 to the Boc-derivative, a yellow solid, according to the procedure of Preparation 17, Step 2.

Step 2: To the product of Step 1 (0.77 g, 2.4 mmol) in EtOH (15 ml) add $NaBH_4$ (0.046 g, 1.2 mmol). Stir 2 h, add $NaBH_4$ (0.023 g, 0.6 mmol), stir 1 h, and add the same amount. Stir 1 h, concentrate, and partition between $CH_2Cl_2$ and water. Wash with brine, dry ($MgSO_4$) and concentrate to obtain the alcohol as a light yellow solid.

Step 3: To the product Step 2 (0.61 g, 1.9 mmol) in THF (10 ml) add NaH (60% in oil, 0.12 g, 3.0 mmol). Stir 10 min and add $CH_3I$ (0.32 g, 2.3 mmol). Stir 72 h and add $CH_3I$ (0.16 g, 1.2 mmol). Stir 24 h and add NaH (60% in oil, 0.062 g, 1.5 mmol) and $CH_3I$ (0.16 g, 1.2 mmol). Stir 24 h and add NaH (60% in oil, 0.034 g, 0.8 mmol). Stir 24 h, pour onto ice-water, and extract with ether. Wash with brine, dry ($MgSO_4$) and concentrate to obtain the crude methyl ether as a yellow solid.

Step 4: Convert the product of Step 3 according to the procedure of Preparation 9, Step 2, to give the title compound as a yellow oil after PLC purification.

Preparation 26

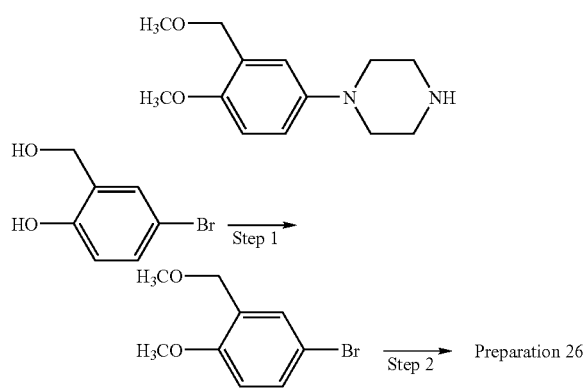

Step 1: To 5-bromo-2-hydroxybenzyl alcohol (1.97 g, 9.7 mmol) in DMF (10 ml) add NaH (60% in oil, 0.81 g, 20.4 mmol). Stir 10 min, add $CH_3I$ (1.39 ml, 22.3 mmol), and stir 1 h. Concentrate and partition between EtOAc and 5% citric acid. Wash with 1N NaOH, then brine. Dry ($MgSO_4$) and concentrate to obtain the crude di-ether as a yellow oil.

Step 2: Convert the product of Step 1 to the aryl-piperazine, a brown solid, following the procedure of Preparation 5.

Preparation 27

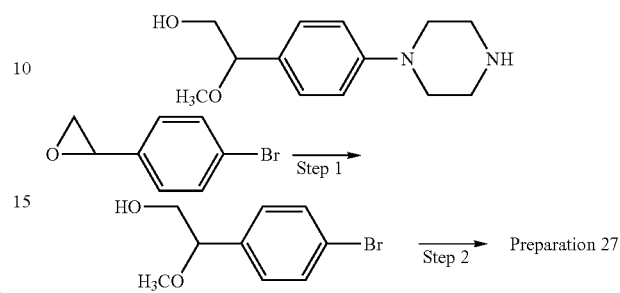

Step 1: Add conc. $H_2SO_4$ (0.10 ml) to $CH_3OH$ (10 ml) cooled in ice. Add dropwise (4-bromophenyl)oxirane (3.14 g, 15.8 mmol) in $CH_3OH$ (5 ml). Heat at 65° C. 18 h, add 4N HCl/dioxane (5 ml), and allow to cool. Partition between ether and water, dry ($MgSO_4$) and concentrate to obtain the crude product as a yellow oil containing the isomeric benzylic alcohol as a minor component.

Step 2: Convert the product of Step 1 to the aryl-piperazine, a yellow oil, following the procedure of Preparation 5.

Preparation 28

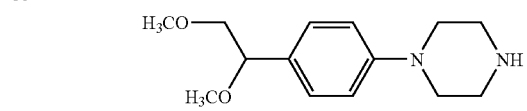

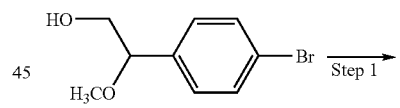

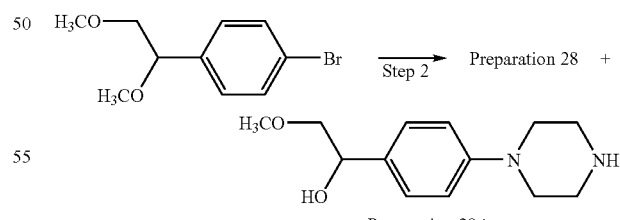

Step 1: Cool in ice a solution of the crude product of Preparation 27, Step 1 (1.70 g, 8.0 mmol) in THF (20 ml). Add NaH (60% in oil, 0.38 g, 9.6 mmol). Stir 10 min, add $CH_3I$ (1.36 g, 9.6 mmol), and stir 2 h. Partition between ether and brine, dry ($MgSO_4$) and concentrate to obtain the crude product as a yellow oil containing the benzylic alcohol as a minor component.

Step 2: Convert the product of Step 1 to the aryl-piperazine following the procedure of Preparation 5. Isolate by chromatography the title compound as a yellow oil, and a side-product, the benzylic alcohol mono-ether, 28A, a yellow solid.

Preparation 29

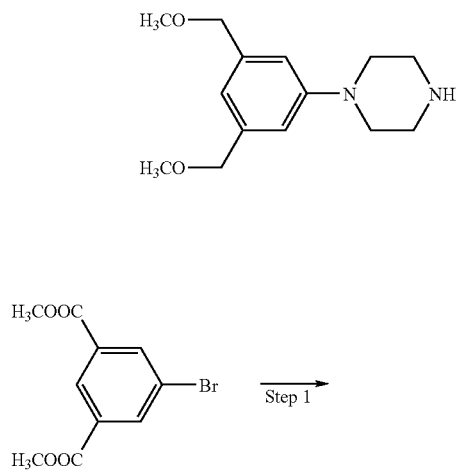

Step 1: Cool a solution of the diester (3.0 g, 1 mmol) in THF (20 ml) to 0° C. and add dropwise 1.0M LiAlH$_4$ in THF (13.2 ml, 13.2 mmol). Heat at 60° C. 2 h, allow to cool, and add water (0.50 ml), then 15% NaOH (0.50 ml), then water (0.50 ml). Filter and concentrate to obtain the diol as a white solid.

Step 2: Convert the diol to the diether, a colorless oil, similarly to Preparation 26, Step 1.

Step 3: Treat the product of Step 2 with piperazine according to the procedure of Preparation 5 to obtain the aryl-piperazine as a brown oil.

In a similar fashion from 4-bromophthalic anhydride obtain Preparation 29-2.

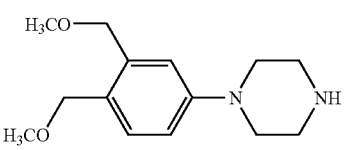

Preparation 29-2

Preparation 30

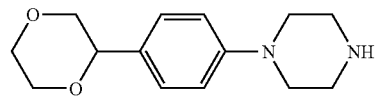

Step 1: Add conc. H$_2$SO$_4$ (0.08 ml) to ethylene glycol (1.40 g, 22.6 mmol) cooled in ice. Add (4-bromophenyl)oxirane (3.00 g, 15.1 mmol). Heat at 135° C. 2.5 h, and allow to cool. Partition between ether and water, wash with brine, dry (MgSO$_4$) and concentrate. Chromatograph on silica to obtain the dioxane as a yellow solid.

Step 2: Convert the product of Step 1 to the aryl-piperazine, a yellow solid, following the procedure of Preparation 5.

Preparation 31

Step 1: To the product of Preparation 22, Step 1 (1.50 g, 7.3 mmol) in DMF (20 ml) at 0° C. add NaH (60% in oil, 0.35 g, 0.21 g NaH, 8.8 mmol). Stir 10 min. and add 2-bromoethyl methyl ether (1.22 g, 8.8 mmol). Heat at 60° C. 18 h, add K$_2$CO$_3$ (1.40 g), KI (1.21 g), and additional bromo-ether (1.22 g). Heat at 100° C. 18 h, allow to cool, and partition between ether and water. Dry (MgSO$_4$) and concentrate to obtain the crude product as a yellow oil.

Step 2: Treat the product of Step 1 with piperazine according to the procedure of Preparation 5 to obtain the aryl-piperazine as a yellow oil.

Preparation 32

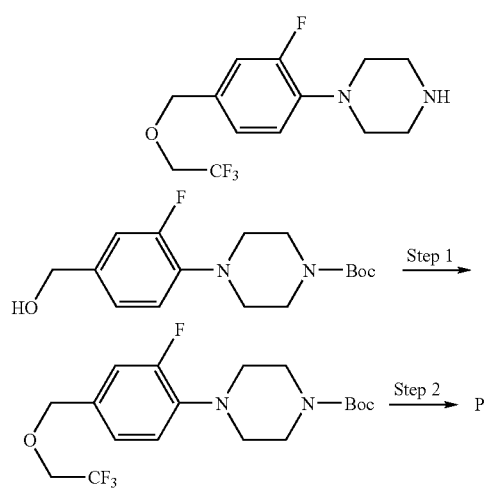

Step 1: To the product of Preparation 12, Step 2 (0.31 g) and ADDP (0.51 g) in benzene (40 ml) add $Bu_3P$ (0.5 mL). Stir 10 min and add dropwise $CF_3CH_2OH$ (0.72 mL). After 1 h, wash with water, dry ($K_2CO_3$), concentrate and chromatograph on silica to obtain the ether.

Step 2: Deprotect the product of Step 1 according to Preparation 9, Step 2, to obtain the aryl-piperazine as a yellow oil.

Preparation 33

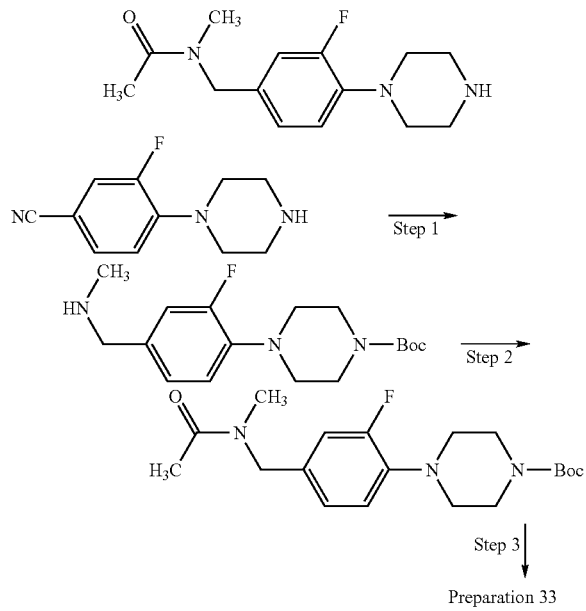

Step 1: To the product of Preparation 18, Step 1 (3.0 g, 9.8 mmol) in 2M methanolic $CH_3NH_2$ (50 ml) add Raney nickel (~0.5 g). Hydrogenate at 60 psi for 18 h, filter through Celite, and concentrate. Partition between $CH_2Cl_2$ and water. Dry ($MgSO_4$) and concentrate to obtain the crude product as a colorless oil.

Steps 2 and 3: Conduct according to Preparation 18, Steps 3 and 4, to obtain the amine as a colorless oil.

In a similar manner to Preparation 18-2, convert the product of Step 1 into Preparation 33-2.

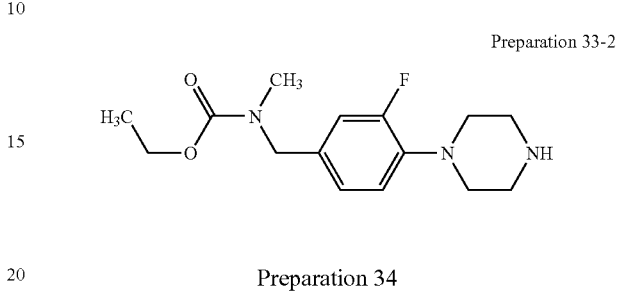

Preparation 34

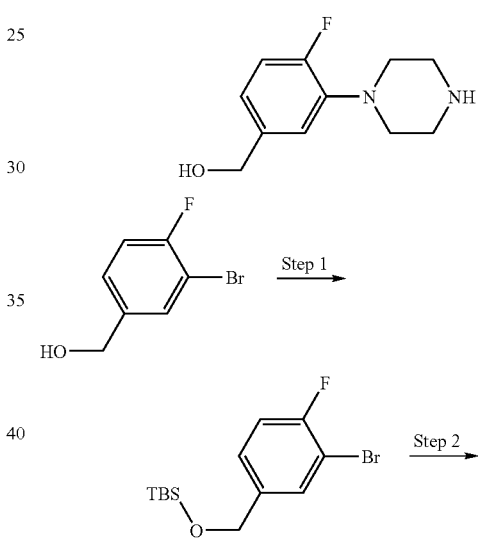

Step 1: To the product of Preparation 22, Step 1 (5.4 g, 26 mmol) in DMF (20 ml) at 0° C. add t-butyldimethylsilyl chloride (4.17 g, 28 mmol) and imidazole (2.69 g, 40 mmol). Stir 2 h and partition between 1:1 ether-hexane and water. Wash with brine, dry ($MgSO_4$) and concentrate to obtain the product as a colorless oil.

Step 2: Treat the product of Step 1 with piperazine according to the procedure of Preparation 5 to obtain the aryl-piperazine as a yellow solid.

Preparation 35

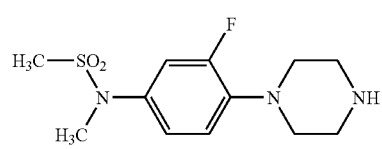

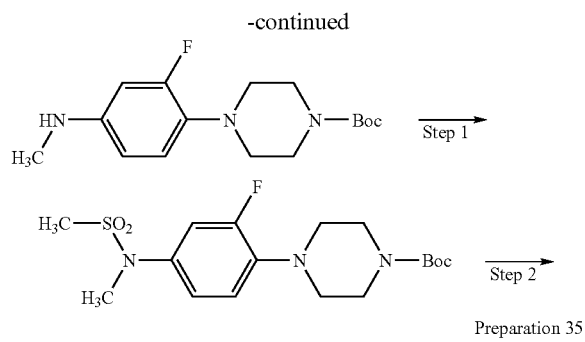

Preparation 35

Step 1: To the product of Preparation 17, Step 6 (0.85 g, 2.7 mmol) and DIPEA (0.72 ml, 4.1 mmol) in CH$_2$Cl$_2$ (15 ml) add CH$_3$SO$_2$Cl (0.26 ml, 3.3 mmol). Stir 1 h and concentrate. Partition between CH$_2$Cl$_2$ and water, wash with brine, dry (MgSO$_4$) and concentrate to obtain the product as a light yellow solid.

Step 2: Treat the product of Step 1 as in Preparation 9, Step 2, to obtain the product as a yellow oil.

In similar fashion, but employing methoxyacetyl chloride in place of CH$_3$SO$_2$Cl in Step 1, obtain Preparation 35-2.

Preparation 35-2

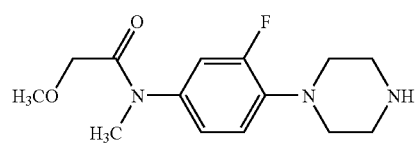

Preparation 36

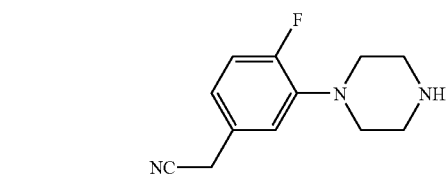

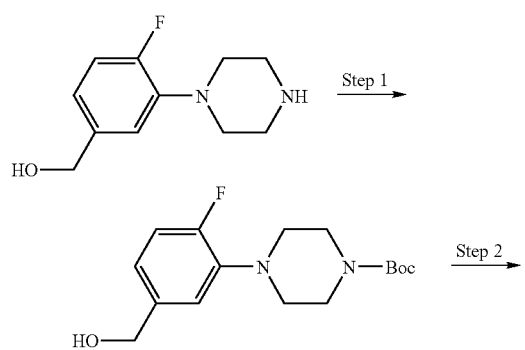

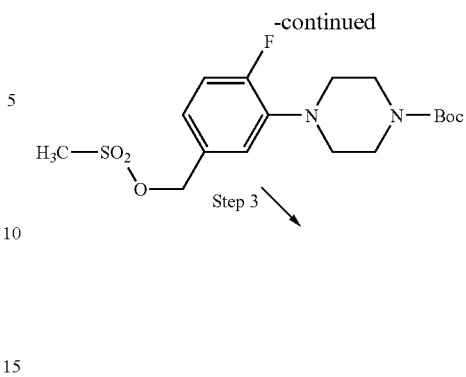

Step 1: Convert the product of Preparation 34 to a solution of the Boc-derivative according to Preparation 18, Step 1.

Step 2: Convert the product of Step 1 to a solution of the crude methanesulfonate ester, an oil, similarly to Preparation 35, Step 1.

Step 3: Treat the product of Step 3 with 3 equivalents of KCN in 5:1 EtOH-water. Reflux 18 h, concentrate, and partition between ether and water. Wash with brine, dry (MgSO$_4$) concentrate, and chromatograph on silica to obtain the product as a yellow oil.

Step 4: Deprotect the product of Step 4 acccording to Preparation 9, Step 2, to obtain the aryl-piperazine as a yellow oil.

Preparation 37

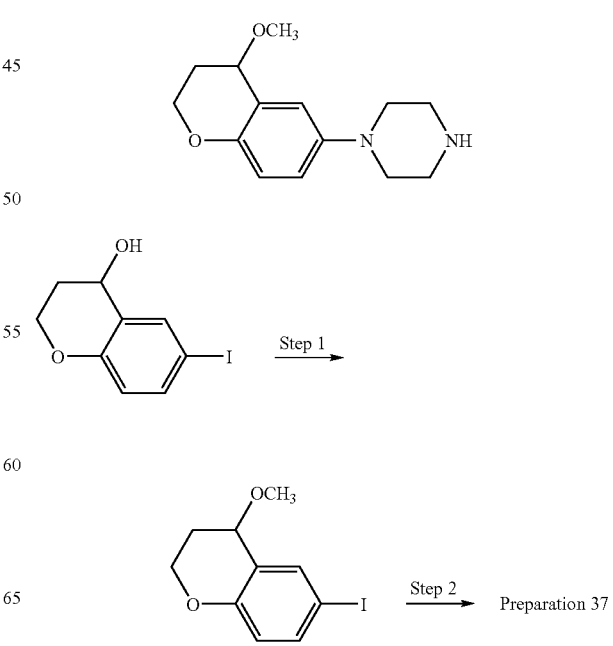

Step 1: Convert the alcohol (obtained by the procedure of *Synthesis* 1997, 23) to the methyl ether according to Preparation 22, Step 2.

Step 2: Treat the product of Step 1 with piperazine according to the procedure of Preparation 5 to obtain the aryl-piperazine as a yellow oil.

Preparation 38

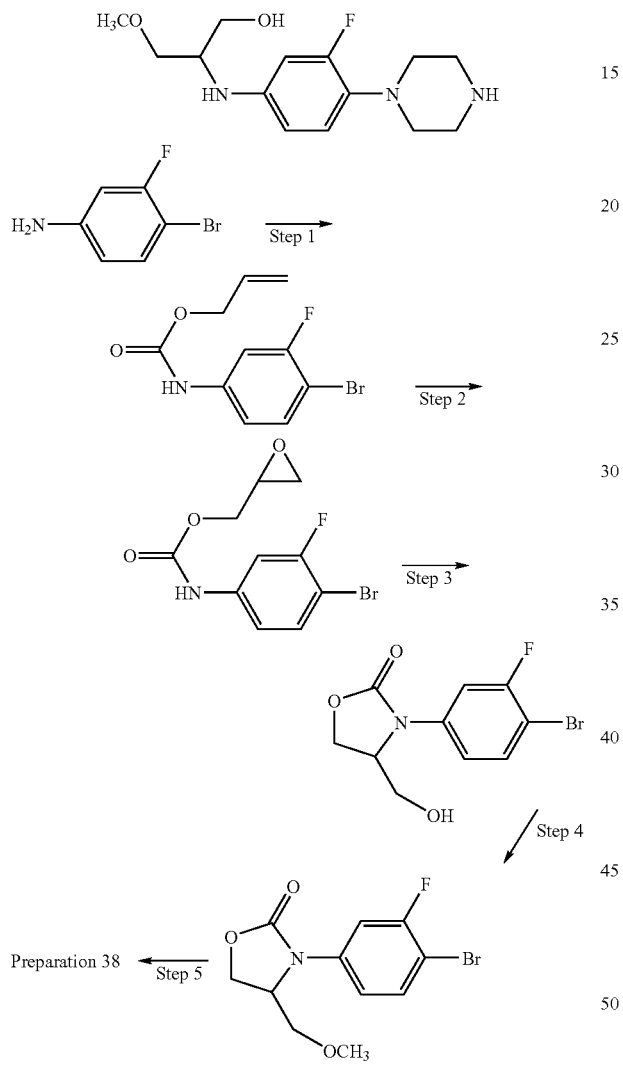

Step 1: Cool in ice a solution of 4-bromo-3-fluoroaniline (2.76 g, 14.5 mmol) in THF 30 ml). Add DIPEA (3.1 ml, 17.4 mmol) and then allyl chloroformate (1.67 ml, 15.2 mmol). Stir 2 h and partition between ether and sat. NaHCO$_3$. Dry (MgSO$_4$) and concentrate to obtain the carbamate as a yellow oil.

Step 2: Treat the product of Step 1 (4.00 g, 14.6 mmol) in CH$_2$Cl$_2$ (40 ml) with m-chloroperbenzoic acid (~70%, 5.38 g, ~20 mmol). Stir 18 h and wash with sat. NaHCO$_3$ (+2 g Na$_2$S$_2$O$_3$). Dry (MgSO$_4$), and concentrate to obtain a yellow solid. Wash with 2:1 hexane-CH$_2$Cl$_2$ to obtain the epoxide as a yellow solid.

Step 3: Heat the product of Step 2 (3.52 g) in pyridine (30 ml) at reflux 10 min. Concentrate and partition between CH$_2$Cl$_2$ and 1N HCl. Wash with 1N NaHCO$_3$, dry (MgSO$_4$), concentrate and chromatograph on silica to obtain the alcohol as a yellow solid.

Step 4: Treat the product of Step 3 with CH$_3$I according to Preparation 22, Step 2, to obtain the ether as a yellow solid.

Step 5: Treat the product of Step 4 with piperazine according to the procedure of Preparation 5. Separate the products by chromatography to obtain the alcohol as a yellow solid.

Preparation 39

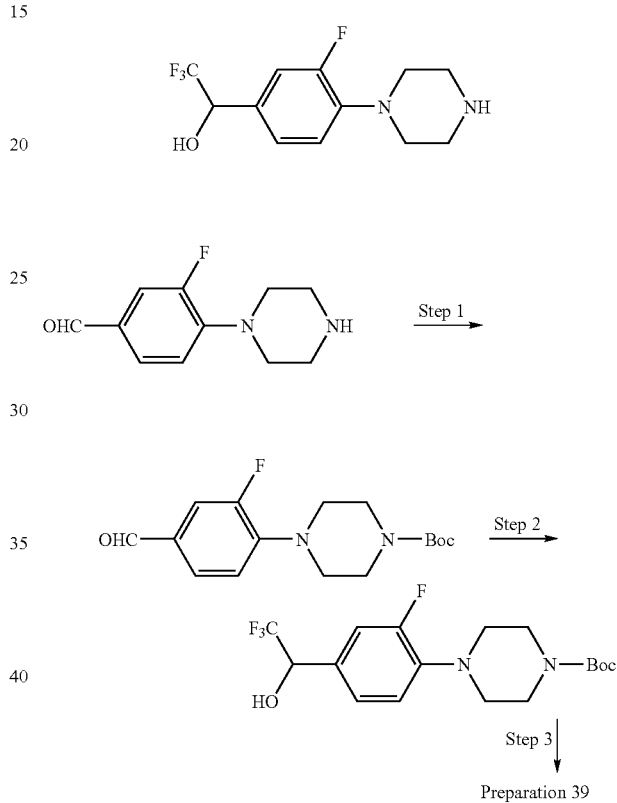

Step 1: Convert the product of Preparation 13-6 to the Boc-derivative according to Preparation 18, Step 1.

Step 2: To a solution of the product of Step 1 (1.5 g) in THF (50 ml) at 0° C. add trifluoromethyltrimethylsilane (1.1 mL), followed by TBAF (0.4 mL). After 1 h quench with 0.5N HCl (10 ml). Stir 15 min, add EtOAc, wash with sat. NaHCO$_3$, dry (K$_2$CO$_3$), and concentrate to give the alcohol as a yellow solid.

Step 3: Deprotect the product of Step 2 according to Preparation 9, Step 2, to obtain the aryl-piperazine as a yellow oil.

Similarly, from 4-fluorobenzaldehyde, proceeding through the N-Cbz-piperazine as in Preparation 47, produce Preparation 39-2 as a yellow oil.

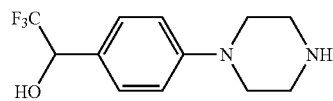

Preparation 40

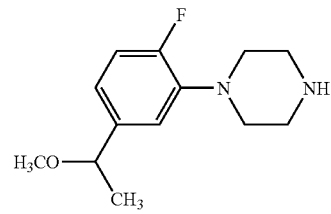

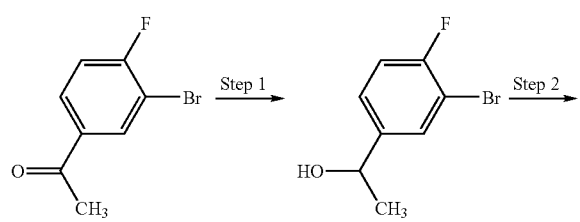

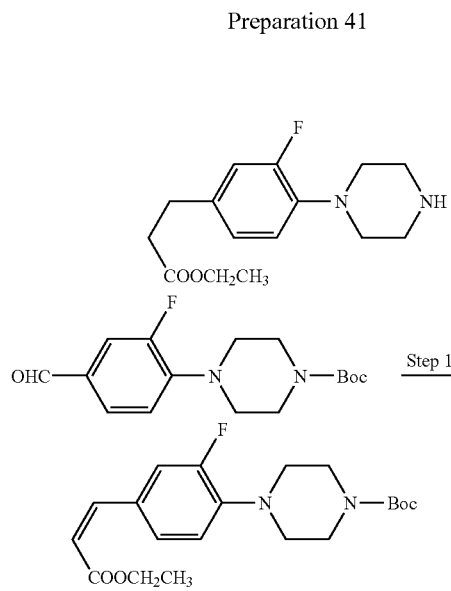

Steps 1 and 2: Reduce the ketone and alkylate according to the procedure of Preparation 22, Steps 1 and 2.

Step 3: Treat the product of Step 2 with piperazine according to the procedure of Preparation 5 to obtain the aryl-piperazine as a yellow oil.

Preparation 41

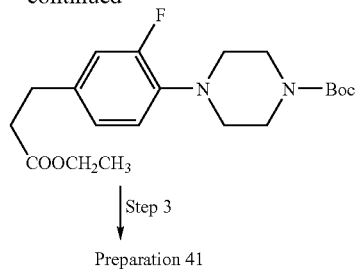

-continued

Step 1: To a suspension of 60% NaH (0.24 g) in THF (20 ml) add diethoxyphosphoryl-acetic acid ethyl ester (1.2 ml). After 0.5 h cool to 0° C. and add the product of Preparation 39, Step 1, (0.93 g) in THF (5 ml). Allow to warm, stir 2 h, and quench with sat. $NH_4Cl$. Extract with EtOAc, dry ($K_2CO_3$), concentrate, and chromatograph on silica to obtain the ester.

Step 2: To the product of Step 1 (1.3 g) in EtOAc (60 ml) add 10% Pd—C (0.15 g). Hydrogenate at 1 atmosphere for 1 h, filter through celite, and concentrate to give the reduced ester as an oil.

Step 3: Deprotect the product of Step 2 according to Preparation 9, Step 2, to obtain the aryl-piperazine as a yellow oil.

Preparation 42

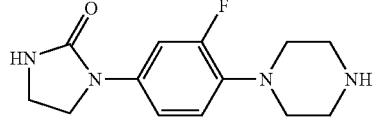

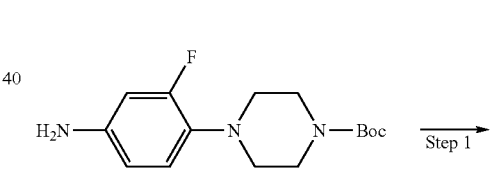

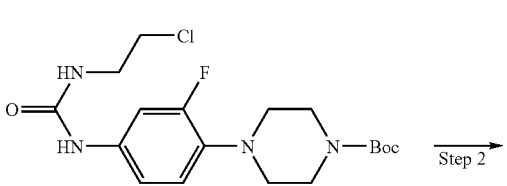

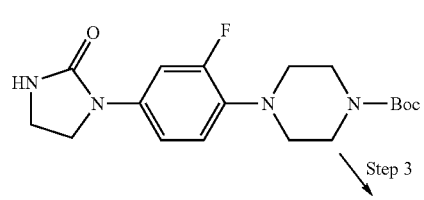

Step 1: Combine the product of Preparation 17, Step 3 (2.2 g, 6.7 mmol) and 2-chloroethyl isocyanate (0.64 ml, 7.4 mmol) in DMF (30 ml). Heat at 60° C. 18 h, allow to cool and partition with CH₂Cl₂ and water. Dry (MgSO₄) and concentrate to obtain the crude urea as a yellow solid.

Step 2: To the crude product of Step 1 above in DMF (100 ml) add NaH (60% in oil, 0.38 g, 0.23 g NaH, 9.5 mmol). Heat at 60° C. 72 h, allow to cool, concentrate, and wash with water to obtain the cyclic urea as a yellow solid.

Step 3: Deprotect the product of Step 2 according to Preparation 9, Step 2, to obtain the aryl-piperazine as a yellow solid.

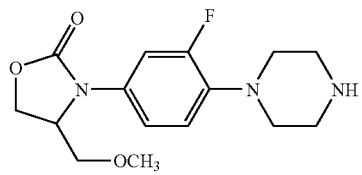

Preparation 43

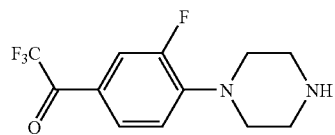

Oxidize the product of Preparation 39, Step 1, with Dess-Martin periodinane in CH₂Cl₂ and deprotect the resulting ketone according to Preparation 9, Step 2, to obtain the aryl-piperazine as a yellow oil.

Preparation 44

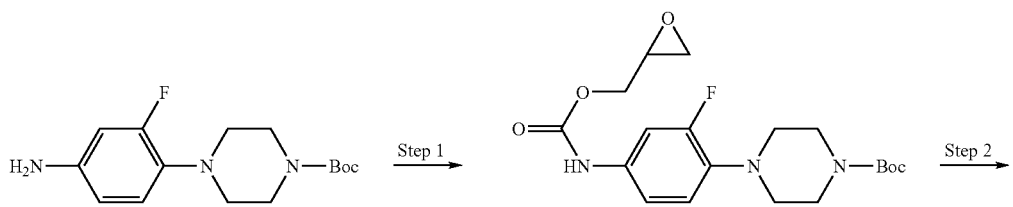

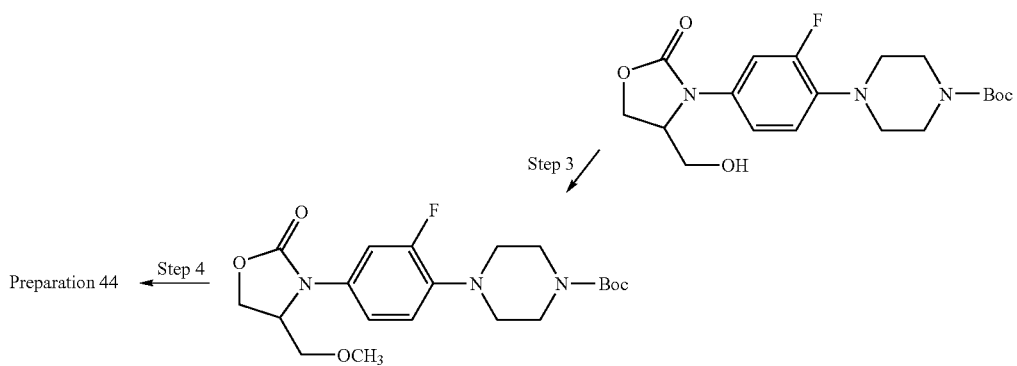

Step 1: Cool in ice a solution of glycidol (0.63 g, 8.5 mmol) in ether (30 ml). Add DIPEA (1.6 ml, 8.5 mmol) and phosgene (1.85M in toluene, 5.8 ml, 10.8 mmol). Stir 2 h, filter, and concentrate. Dissolve in ether (50 ml) and add the product of Preparation 17, Step 3 (2.50 g, 7.7 mmol) and DIPEA (1.6 ml, 8.5 mmol). Stir 2 h, wash with sat. NaHCO₃, dry (MgSO₄), and concentrate to obtain the carbamate as a yellow solid.

Step 2: Treat the product of Step 1 as in Preparation 38, Step 3, and chromatograph on silica to obtain the alcohol as a yellow solid.

Step 3: Treat the product of Step 2 as in Preparation 38, Step 4, to obtain the ether as a yellow oil.

Step 4: Deprotect the product of Step 3 according to Preparation 9, Step 2, to obtain the aryl-piperazine as a yellow solid.

Preparation 45

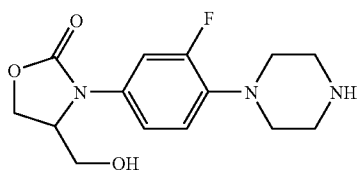

Deprotect the product of Preparation 44, Step 2, according to Preparation 9, Step 2, to obtain the aryl-piperazine as a yellow solid.

Preparation 46

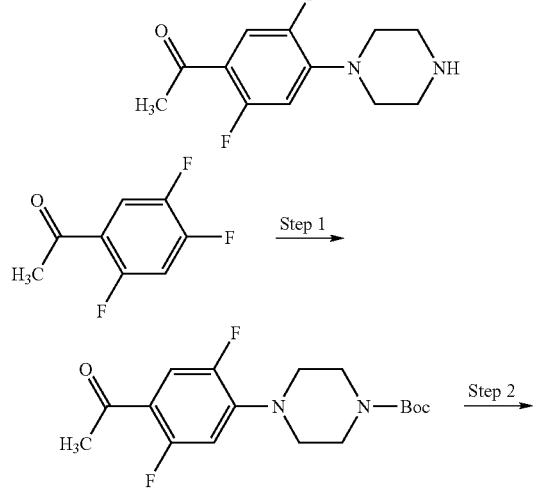

Preparation 46

Step 1: Combine 2',4',5'-trifluoroacetophenone (2.50 g, 14.4 mmol), N-Boc-piperazine (2.87 g, 145.4 mmol) and K₂CO₃ (2.37 g, 17.2 mmol) in DMF (20 ml). Heat at 40° C. 4 h, allow to cool, and stir 64 h. Partition with ether and water, dry (MgSO₄) and concentrate to obtain the aryl-piperazine as a yellow solid.

Step 2: Deprotect the product of Step 1 according to Preparation 9, Step 2, to obtain the aryl-piperazine as a yellow solid.

Similarly produce Preparation 46-2 as a colorless oil.

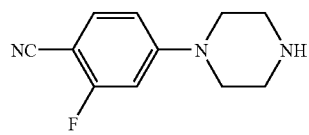

Preparation 47

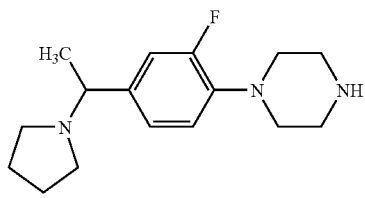

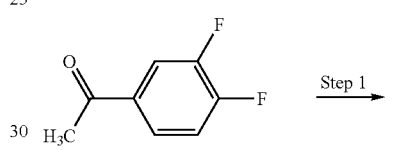

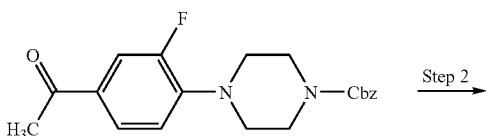

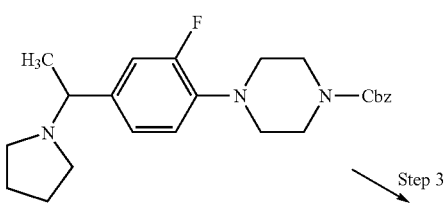

Preparation 47

Step 1: Heat a mixture 3',4'-difluoroacetophenone (0.25 g), piperazine-1-carboxylic acid benzyl ester (1.84 ml), and K₂CO₃ (1.32 g) in toluene (4 ml) by microwave at 150° C. 0.5 h. Allow to cool and partition with EtOAc and water. Dry (K₂CO₃), concentrate and chromatograph on silica to obtain the aryl-piperazine.

Step 2: To the product of Step 1 (0.35 g) in CH₂Cl₂ (10 ml) add pyrrolidine (0.37 g), followed by sodium triacetoxyborohydride (1.1 g). Stir 48 h, quench with sat. NaHCO₃ and extract with CH₂Cl₂. Dry (K₂CO₃), concentrate, and purify by PLC to give the amine.

Step 3: Hydrogenate the product of Step 2 according to Example 41, Step 2 (16 h) to give the piperazine as an oil.

Starting with 2,4,5-trifluorobenzonitrile and employing DMF as solvent in Step 1, produce an N-Cbz aryl-piperazine and deprotect according to Step 3 to provide Preparation 47-2.

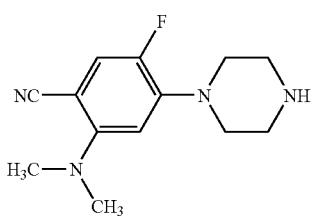

Preparation 48

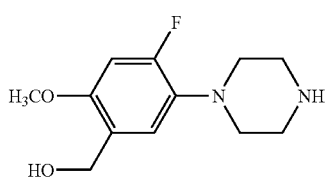

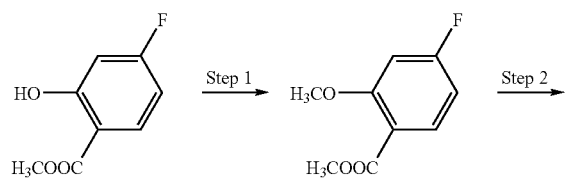

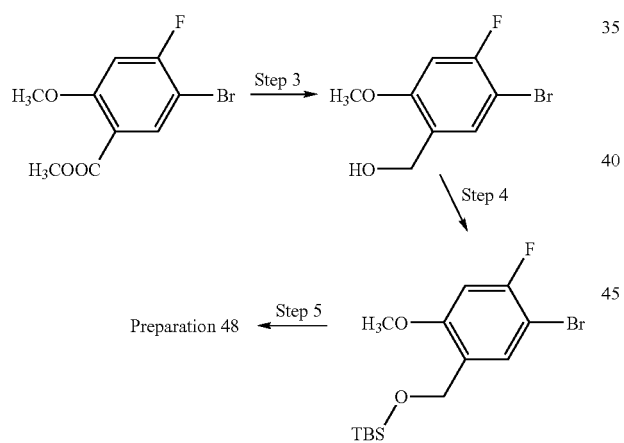

Step 1: Treat methyl 4-fluorosalicylate (1.42 g, 7.7 mmol) in DMF (20 ml) with NaH (60% in oil, 0.46 g, 0.28 g NaH, 12 mmol) and CH$_3$I (0.62 ml, 10 mmol). Stir 18 h and partition with EtOAc and 5% citric acid. Wash with 1N NaOH, then brine, dry (MgSO$_4$) and concentrate to obtain the ether as a yellow oil.

Step 2: Combine the product of Step 1 (1.43 g, 7.2 mmol) and iron powder (0.018 g) in CH$_2$Cl$_2$ (15 ml). Add dropwise Br$_2$ (0.44 ml, 8.7 mmol) in CH$_2$Cl$_2$ (5 ml). Stir 18 h and wash with water, then 1N NaOH. Dry (MgSO$_4$) and concentrate to obtain the bromide as a yellow solid.

Step 3: Cool in ice a solution of the product of Step 2 (1.15 g, 4.1 mmol) in THF (15 ml). Add dropwise BH$_3$.Me$_2$S (2.0M in THF, 4.2 ml, 8.4 mmol). Heat at 60° C. 18 h, allow to cool, quench with methanol, concentrate and partition with EtOAc and sat. NaHCO$_3$. Wash with water, then brine, dry (MgSO$_4$) and concentrate to obtain the alcohol as a yellow oil.

Step 4: Convert the product of Step 3 to the TBS ether acccording to Preparation 34, Step 1, to obtain a colorless oil.

Step 5: Treat the product of Step 4 with piperazine according to the procedure of Preparation 5 to obtain the aryl-piperazine as a yellow solid.

For Preparation 48-2, methylate ethyl 5-bromosalicylate and reduce with BH$_3$.Me$_2$S. Treat the resulting alcohol according to Steps 4 and 5 above to obtain the aryl-piperazine as a brown oil.

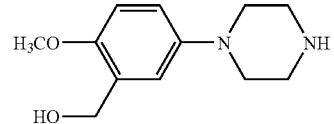

Preparation 49

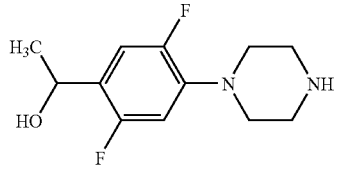

Reduce the product of Preparation 46 as in Preparation 22, Step 1, to obtain the aryl-piperazine as a yellow solid.

Preparation 50

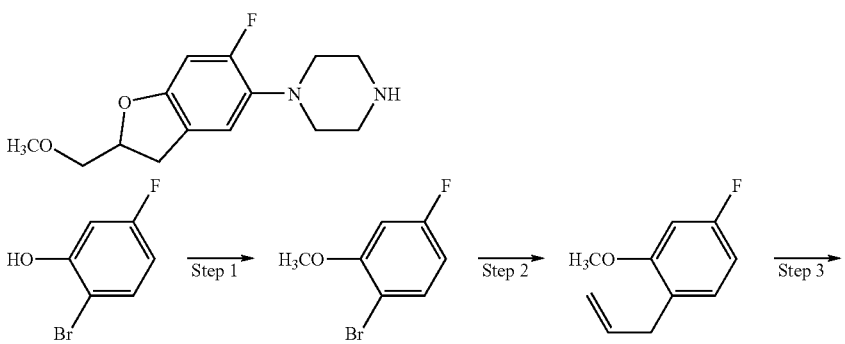

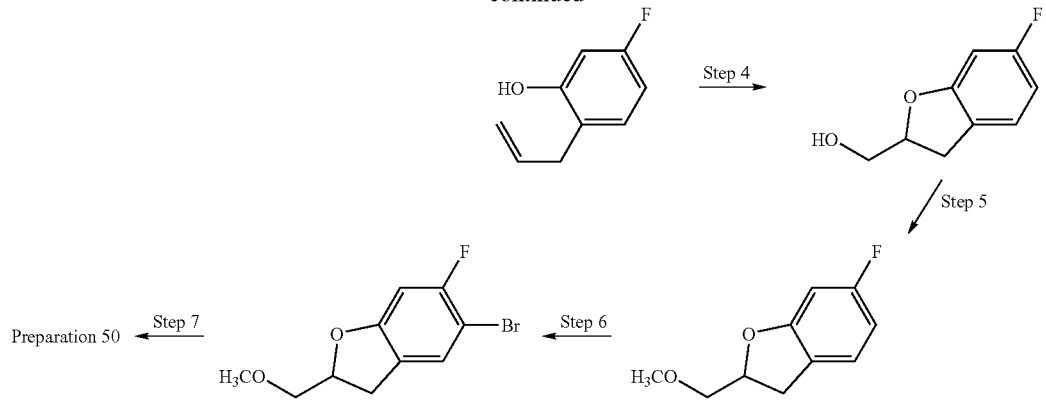

Step 1: Methylate 2-bromo-5-fluorophenol according to the procedure of Preparation 22, Step 2, to obtain the ether as a colorless oil.

Step 2: Cool the product of Step 1 (5.36 g, 26.1 mmol) in ether (100 ml) to −40° C. and add dropwise n-BuLi (2.5M in hexane, 14.6 ml, 37 mmol). Stir 1 h, add CuI (2.48 g, 13.1 mmol) and stir 2 h more. Add allyl bromide (3.80 g, 31 mmol). Allow to warm, stir 18 h, and filter through Celite. Wash with sat. NH$_4$Cl, then brine. Dry (MgSO$_4$) and concentrate to obtain the allyl compound as a yellow oil.

Step 3: Cool to 0° C. the product of Step 2 (4.17 g, 25.1 mmol) in CH$_2$Cl$_2$ (40 ml). Add BBr$_3$ (5.02 g, 20 mmol). Allow to warm and heat at reflux 18 h. Pour onto ice, separate the organic, dry (MgSO$_4$), concentrate and chromatograph on silica to obtain the phenol as a yellow oil.

Steps 4-5: Conduct according to the procedure of Preparation 15, Steps 1 and 2, to obtain the ether after chromatography on silica as a colorless oil.

Step 6: Brominate the product of Step 5 according to the procedure of Preparation 48, Step 2, to obtain the bromide as a yellow oil.

Step 7: Treat the product of Step 6 with piperazine according to the procedure of Preparation 5 to obtain the aryl-piperazine as a yellow oil.

Preparation 51

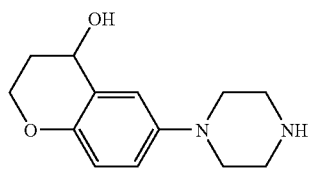

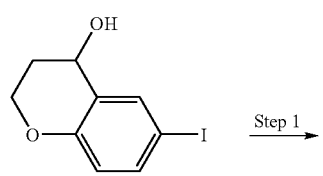

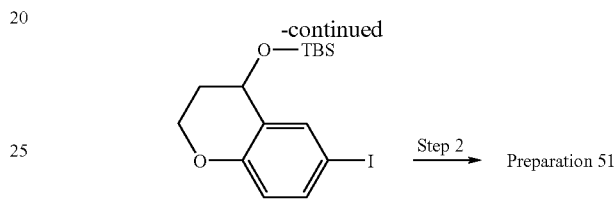

Convert the alcohol (obtained by the procedure of *Synthesis* 1997, 23) according to Preparation 34 to obtain the aryl-piperazine as a yellow oil.

Preparation 52

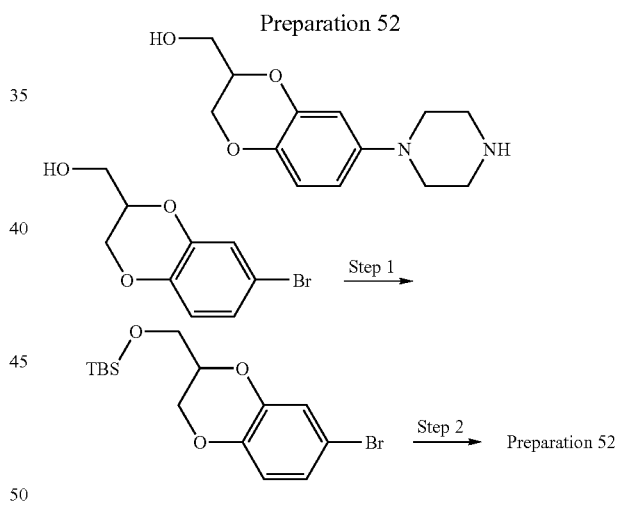

Convert the alcohol (obtained by the procedure of *Bioorg. Med. Chem. Letters* 2001, 2783) according to Preparation 34 to obtain the aryl-piperazine as a yellow solid.

For Preparation 52-2, Boc-protect this material according to Preparation 18, Step 1, and methylate according to Preparation 22, Step 2. Deprotect the resulting material according to Preparation 9, Step 2, to obtain Preparation 55-2 as a yellow solid.

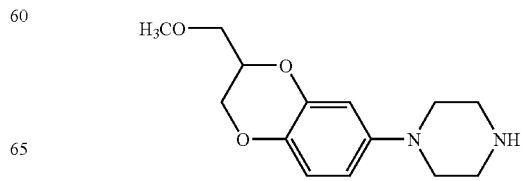

Preparation 53

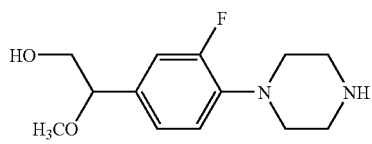

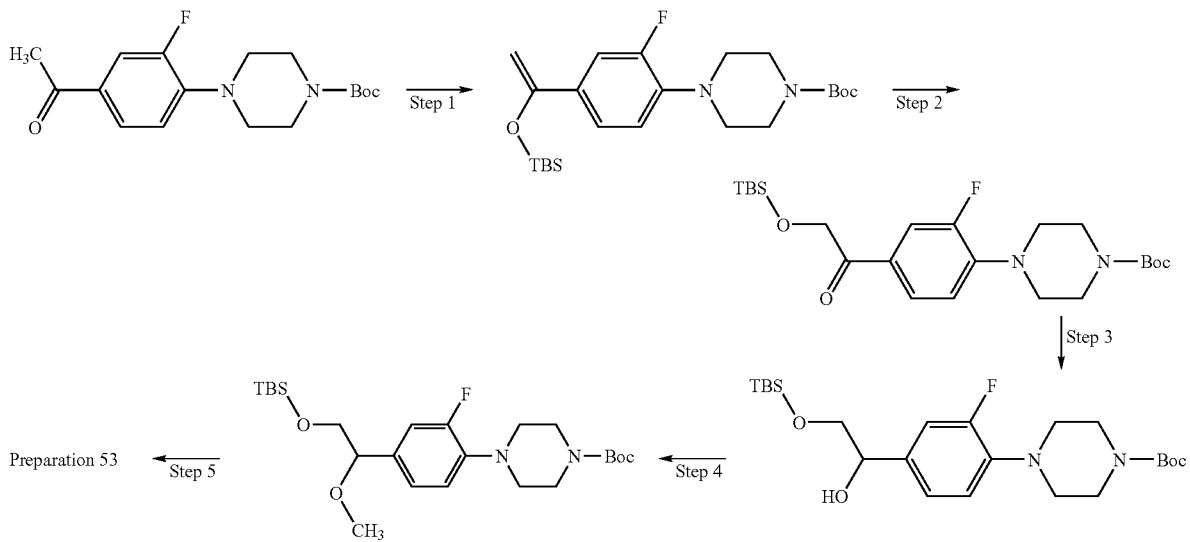

Step 1: Combine the product of Preparation 25, Step 1 (2.95 g, 9.2 mmol), with Et₃N (1.53 ml, 11.0 mmol) in CH₂Cl₂ (15 ml). Cool to 0° C. and add t-butyldimethylsilyl triflate (2.21 ml, 9.6 mmol). Stir 2 h, concentrate and partition with ether and water. Wash with sat. NaHCO₃, dry (MgSO₄), and concentrate to obtain the enol-ether as a yellow oil.

Step 2: Dissolve the product of Step 1 (4.00 g, 9.2 mmol) in CH₂Cl₂ (25 ml). Cool to 0° C. and add m-chloroperbenzoic acid (70-75%, 2.00 g, ~9 mmol). Stir 4 h, wash with sat. NaHCO₃, dry (MgSO₄), concentrate, and chromatograph on silica to obtain the ketone as a white solid.

Step 3: To the product of Step 2 (1.07 g, 2.4 mmol) in THF (15 ml) add NaBH₄ (0.090 g, 2.4 mmol). Stir 3 h, and partition with ether and water. Dry (MgSO₄), and concentrate to obtain the crude alcohol as a yellow oil.

Step 4: Dissolve the crude product of Step 3 above in DMF (5 ml). Add NaH (60% in oil, 0.133 g, 0.080 g NaH, 3.3 mmol), stir 10 min, and add CH₃I (0.16 ml, 2.5 mmol). Stir 1 h and partition with ether and water. Dry (MgSO₄) and concentrate to obtain the crude ether as a yellow oil.

Step 5: Dissolve the crude product of Step 4 above in TFA (15 ml) at 0° C. Stir 0.5 h and concentrate. Basify with aq.ammonia and extract with CH₂Cl₂. Dry (MgSO₄), and concentrate to obtain the aryl-piperazine as a yellow oil.

Preparation 54

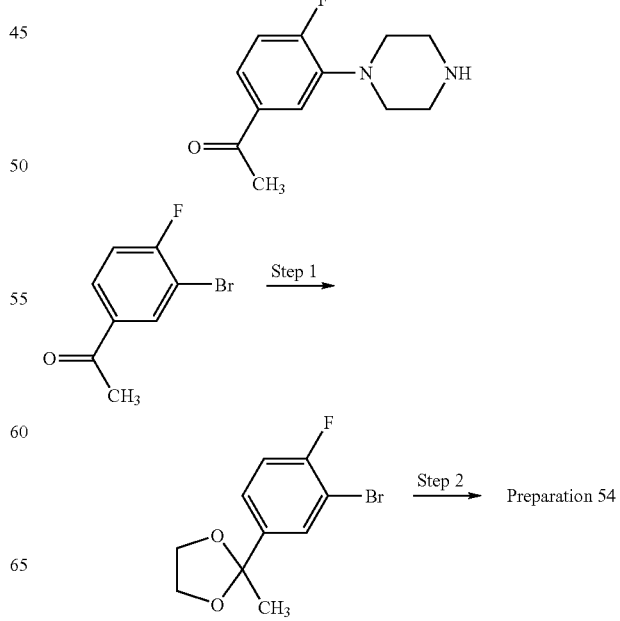

Step 1: Combine 3'-bromo-4'-fluuoroacetophenone (2.60 g, 12.0 mmol), ethylene gycol (3.3 ml, 59 mmol), and TsOH.H₂O (0.23 g, 1.2 mmol) in toluene (60 ml). Reflux with water separation (Dean-Stark) 4 h, allow to cool, and partition with hexane and 1N NaHCO₃. Wash with water, then brine, dry (MgSO₄), and concentrate to obtain the ketal as a colorless oil.

Step 2: Treat the product of Step 1 with piperazine according to the procedure of Preparation 5 to obtain the aryl-piperazine as rosettes, mp 53-6° C.

In similar fashion, convert 3'-bromoacetophenone to Preparation 54-2.

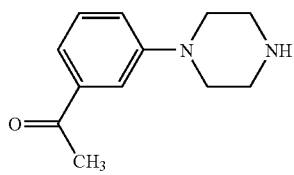

Preparation 55

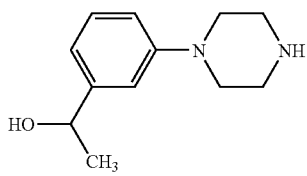

Treat 1-(3-bromophenyl)ethanol according to Preparation 34 to obtain the aryl-piperazine as an off-white solid.

Preparation 56

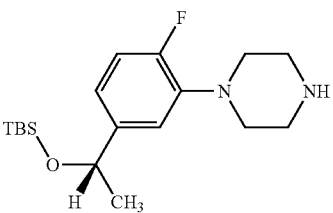

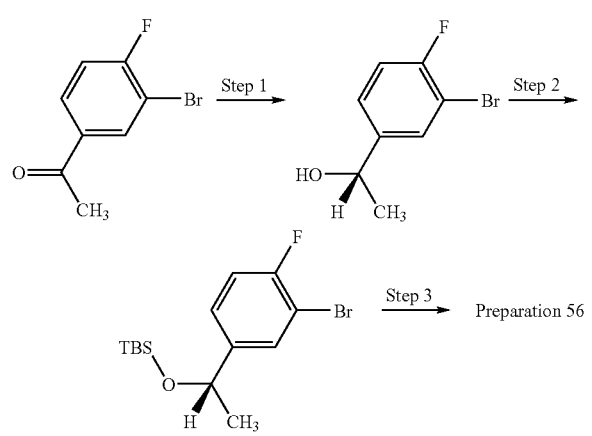

Step 1: To (R)-2-methyl-CBS-oxazaborolidine (1.0M in toluene, 7.1 ml, 7.1 mmol) add BH₃.Me₂S (2.0M in THF, 3.0 ml, 6.0 mmol). Stir 0.5 h and cool to −78° C. Add 3'-bromo-4'-fluoroacetophenone (1.50 g, 6.9 mmol). Allow to warm to −20° C. and stir 5 h at −20° C. Add slowly MeOH (20 ml). Concentrate and chromatograph on silica to obtain the alcohol as a colorless oil.

Steps 2 and 3: Convert the product of Step 1 to the aryl-piperazine according to Preparation 34, modifying the work-up of the piperazine reaction by concentrating, partitioning with CH₂Cl₂ and water, drying (MgSO₄), and concentrating to obtain the product TBS-ether as a yellow oil.

In similar fashion with (S)-2-methyl-CBS-oxazaborolidine, produce the enantiomer, Preparation 56-2, as a yellow oil.

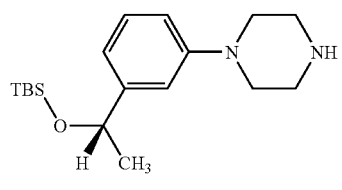

Starting with 3'-bromoacetophenone, in similar fashion prepare the pair of enantiomers Preparation 56-3 and 56-4, as yellow oils.

Prep. 56-3

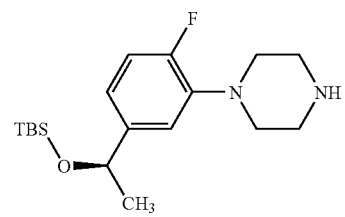

Prep. 56-4

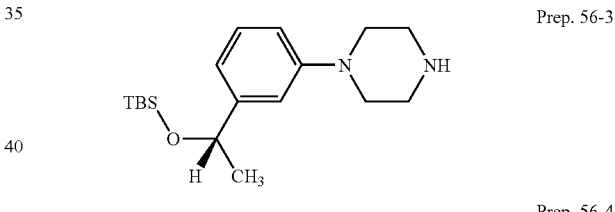

Preparation 57

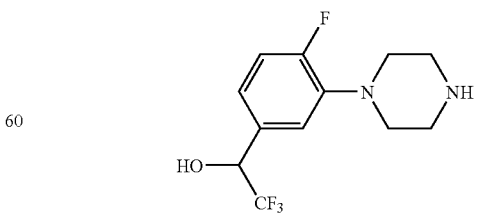

Treat 3-bromo-4-fluorobenzaldehyde with trifluoromethyltrimethylsilane according to Preparation 39, but without HCl work-up, to give the trimethylsilyl ether. React the ether with piperazine according to Preparation 5 to obtain the title aryl-piperazine.

Preparation 58

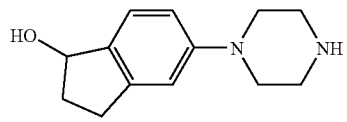

Treat the product of Preparation 13-3 with NaBH₄ according to Preparation 22, Step 1, to obtain the title aryl-piperazine as a yellow solid.

Preparation 59

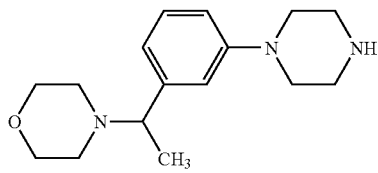

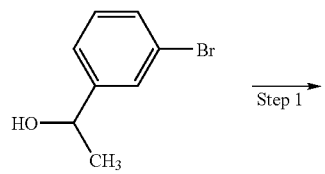

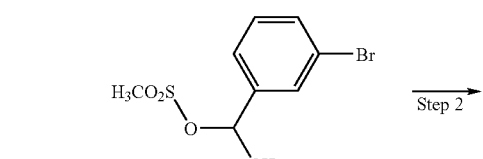

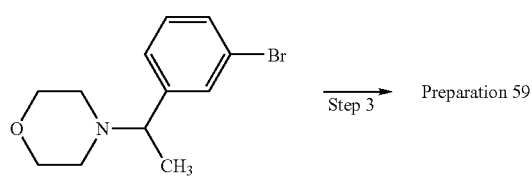

Step 1: Convert 1-(3-bromophenyl)ethanol to the methanesulfonate ester, a pale orange oil, according to Preparation 36, Step 2.

Step 2: Combine the product of Step 1, (3.33 g, 11.9 mmol) and morpholine (3.31 g, 38 mmol) in acetonitrile (10 ml). Heat at 80° C. 4 h, allow to cool, concentrate, and partition with ether and water. Extract with 1N HCl, basify the aqueous with Na₂CO₃, and extract with CH₂Cl₂. Dry (MgSO₄), and concentrate to obtain the product as a pale orange oil.

Preparation 60

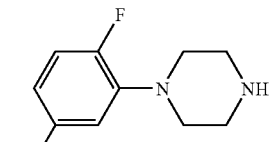

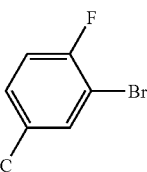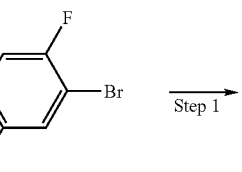

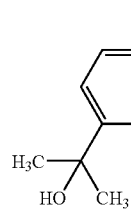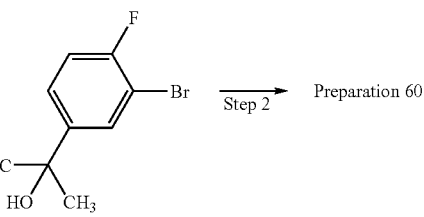

Step 1: To methyl 3-bromo-4-fluorobenzoate (3.02 g, 13.0 mmol) in ether (30 ml) at 0° C. add dropwise MeMgBr (3.0M in ether, 11 ml, 33 mmol). Stir 1 h and pour onto ice. Acidify with 1N HCl, separate the ether, wash with 1N NaHCO₃, dry (MgSO₄), and concentrate to obtain the product as a colorless oil.

Step 2: Treat the product of Step 1 with piperazine according to the procedure of Preparation 5 to obtain the title aryl-piperazine as off-white crystals, mp 171-4° C.

In analogous fashion from 3'-bromoacetophenone produce Preparation 60-2, a yellow solid.

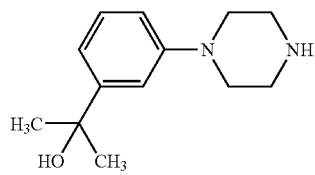

Preparation 61

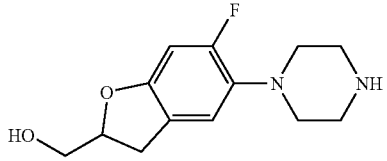

Treat the product of Preparation 50, Step 4, according to Preparation 34 to obtain the title aryl-piperazine as yellow oil.

Preparation 62

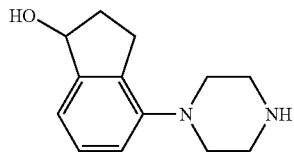

Reduce 4-bromo-1-indanone (prepared according to Synth. Comm. 1994, 2277) according to Preparation 22, Step 1. Convert to the TBS ether and react with piperazine according to Preparation 34. Deprotect the TBS-protected aryl-piperazine according to Example 2, Step 2, to obtain the alcohol as a brown oil.

Preparation 63

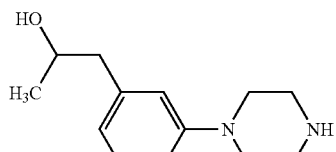

Reduce 1-(3-bromophenyl)-2-propanone according to Preparation 22, Step 1, convert to the TBS ether and react with piperazine according to Preparation 34 to obtain the aryl-piperazine as a yellow oil.

Similarly, convert 1-(4-bromophenyl)-2-propanone to Preparation 63-2, a yellow solid. Likewise, convert 3-bromo-5-acetylpyridine to Preparation 63-3, a yellow oil.

Prep. 63-2

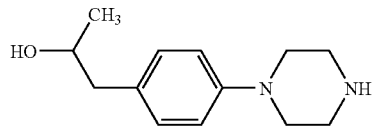

Prep. 63-3

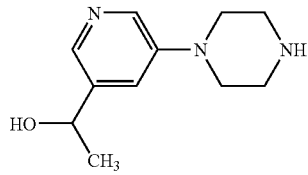

Preparation 64

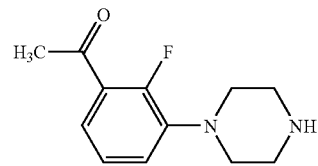

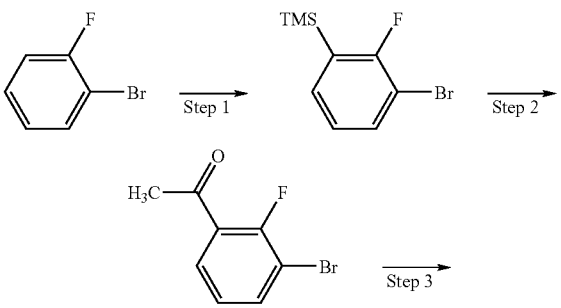

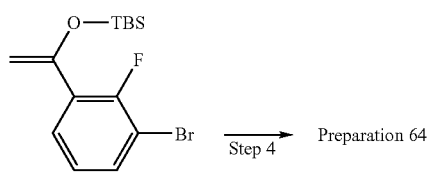

Step 1: To diisopropylamine (6.26 ml, 45 mmol) in THF (80 ml) at −78° C. add n-BuLi (2.5M in hexane, 15.1 ml, 30.2 mmol). Stir 0.5 h and add dropwise 2-bromofluoro-benzene (6.00 g, 34.3 mmol) in THF (5 ml). Stir 2 h and add trimethylsilyl chloride (4.92 ml, 37.7 mmol). Stir 2 h, allow to warm, and stir 18 h. Concentrate, partition with hexane and water, wash with brine, dry (MgSO$_4$), and concentrate to obtain the silane as a yellow oil.

Step 2: Cool to 0° C. a suspension of AlCl$_3$ (4.57 g, 34.3 mmol) in CH$_2$Cl$_2$ (30 ml) add acetyl chloride (2.44 ml, 34.3 mmol). Stir 10 min and add the product of Step 1 (7.70 g, 31.1 mmol) in CH$_2$Cl$_2$ (10 ml). Stir 5 h and add 1N HCl. Dry the CH$_2$Cl$_2$ (MgSO$_4$), and concentrate to obtain the ketone as a yellow oil.

Steps 3 and 4: Convert the product of Step 2 into the silyl enol-ether according to Preparation 53, Step 1, then react with piperazine according to Preparation 5 to obtain the title aryl-piperazine as a yellow solid.

In similar fashion, starting with 2,6-difluorobromobenzene prepare Preparation 64-2, a yellow solid.

Steps 1-4: Treat 3'-bromo-4'-fluoroacetophenone according to Preparation 53, Steps 1-4, to obtain the bromide.

Step 5: React the product of Step 4 with piperazine according to Preparation 5 to obtain the title aryl-piperazine as a yellow oil.

Preparation 66

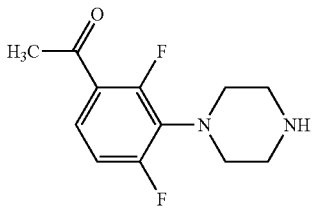

Preparation 65

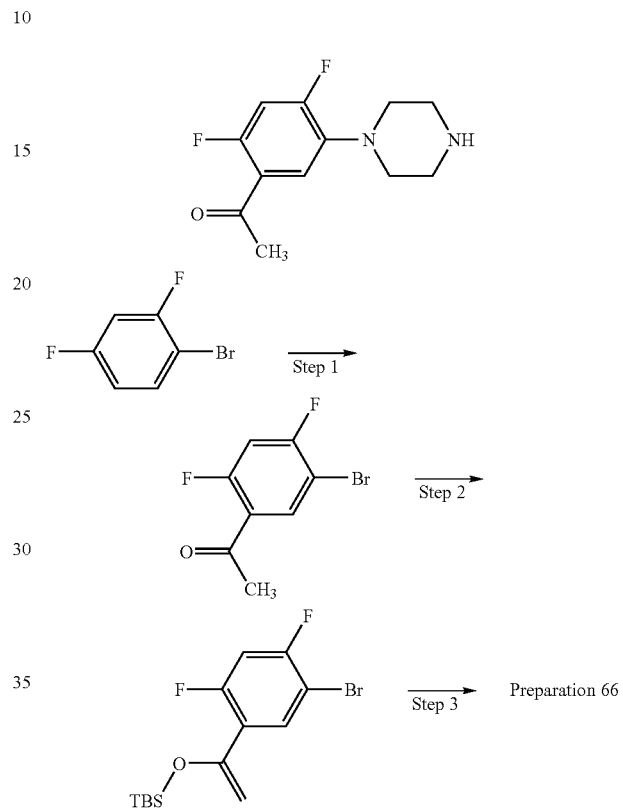

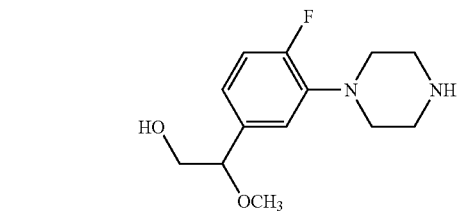

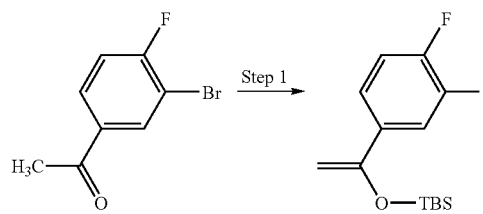

Step 1: Combine 2,4-dibromofluorobenzene (6.00 g, 31 mmol) and $AlCl_3$ (10.4 g, 34.3 mmol) and heat to 60° C. Add dropwise acetyl chloride (3.66 g, 47 mmol). Heat at 95° C. 1.5 h, cool to 0° C., and add ice-water, then conc. HCl (15 ml). Extract with ether, dry ($MgSO_4$), concentrate and chromatograph on silica to obtain the ketone as a brown oil.

Steps 2 and 3: Treat the product of Step 1 according to Preparation 64, Steps 3 and 4, to obtain the title aryl-piperazine as a yellow oil.

Preparation 67

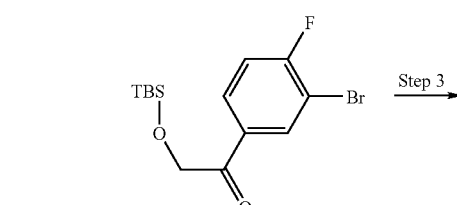

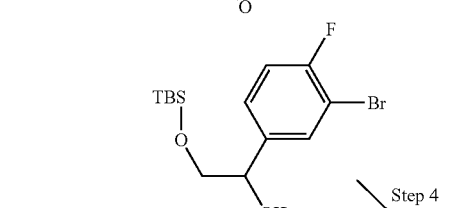

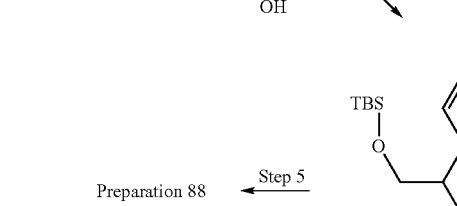

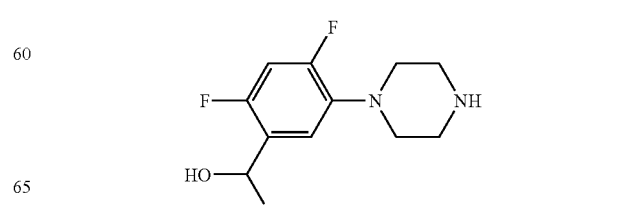

Treat the product of Preparation 66 with NaBH₄ according to the procedure of Preparation 22, Step 1, to obtain the title aryl-piperazine as a yellow oil.

Preparation 68

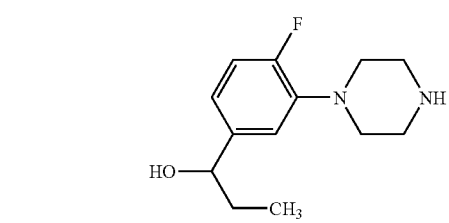

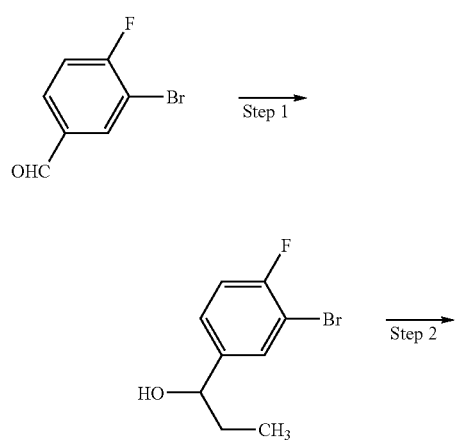

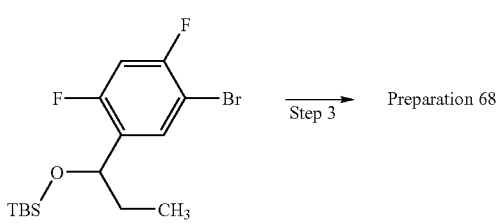 Preparation 68

Step 1: Cool 3-bromo-4-fluorobenzaldehyde (2.00 g, 9.9 mmol) in ether (20 ml) to 0° C. and add dropwise EtMgBr (3.0M in ether, 4.9 ml, 14.8 mmol). Stir 1 h and add 1N HCl. Wash the ether with brine, dry (MgSO₄) and concentrate to obtain the alcohol as a coloress oil Steps 2 and 3: Convert the alcohol to the TBS ether and react with piperazine according to Preparation 34 to obtain the aryl-piperazine as a yellow oil.

In similar fashion, react 3-bromo-6-fluorobenzaldehyde with MeMgBr and convert the resulting alcohol to Preparation 68-2, a sticky solid.

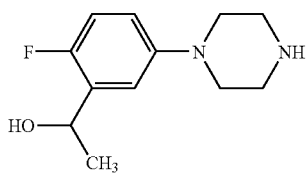

Preparation 69

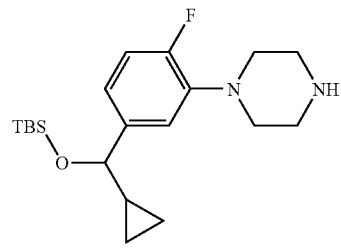

React 3-bromo-4-fluorobenzaldehyde with cyclopropyl-magnesium bromide under the conditions of Preparation 68, Step 1, and treat the alcohol according to Preparation 56, Steps 2 and 3, to obtain the title aryl-piperazine as a black oil.

In similar fashion, obtain Preparation 69-2 as a yellow oil.

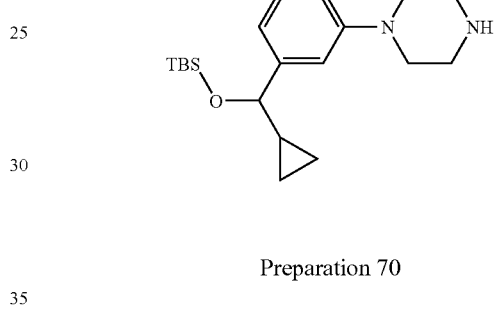

Preparation 70

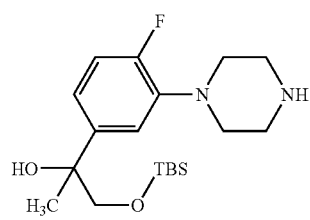

Treat the product of Preparation 65, Step 2 with MeMgBr according to Preparation 68, Step 1, and then with piperazine under the conditions of Preparation 56, Step 3, to obtain the title aryl-piperazine as a yellow oil.

Preparation 71

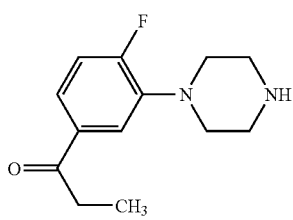

-continued

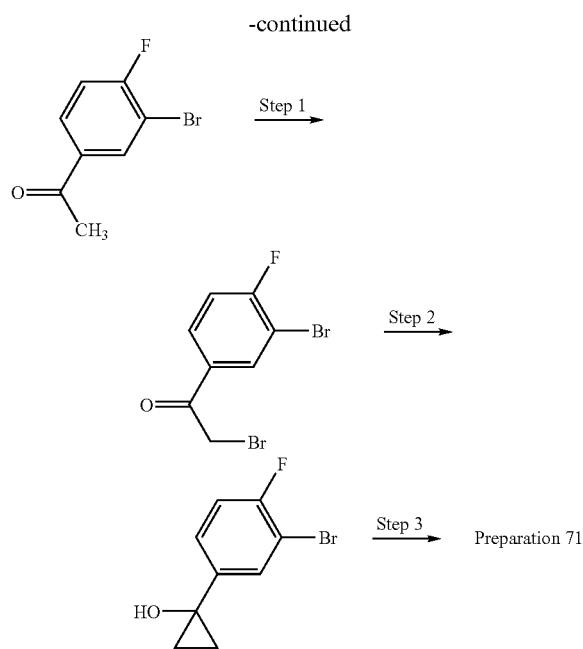

Step, 1: To 3'-bromo-4'-fluoroacetophenone (3.00 g, 13.8 mmol) in CH$_2$Cl$_2$ (15 ml) and acetic acid (0.5 ml) at 10° C. add dropwise bromine (2.43 g, 15.2 mmol) in CH$_2$Cl$_2$ (20 ml). Stir 15 min and concentrate to obtain the crude bromide as a yellow oil.

Step, 2: Cool to 0° C. a suspension of samarium powder (6.24 g, 41.5 mmol) in THF (40 ml). Combine the crude product of Step 1 above with CH$_2$I$_2$ (11.19 g, 41.5 mmol) in THF (60 ml) and add dropwise to the suspension. Stir 0.5 h and add slowly 1N HCl (200 ml). Extract with ether, dry (MgSO$_4$), concentrate, and chromatograph on silica to obtain the cyclopropanol as a yellow oil.

Step, 3: React the product of Step 2 with piperazine according to Preparation 5 and chromatograph on silica to obtain the title propiophenone as a yellow oil.

Preparation 72

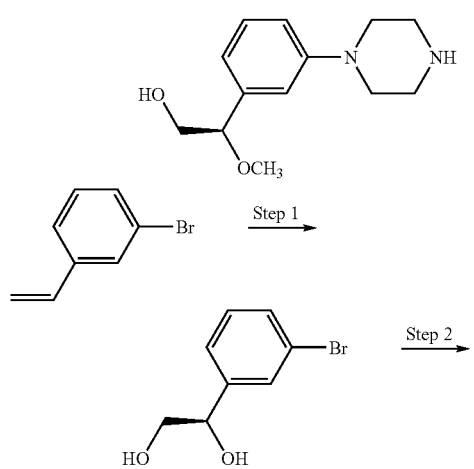

-continued

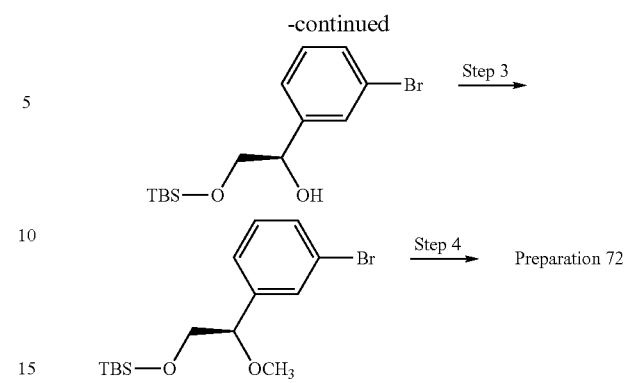

Step 1: Cool to 0° C. the Sharpless oxidizing mixture AD-mix-β (15.3 g) in 1:1 aq. t-BuOH (100 ml). Add m-bromostyrene (2.00 g, 10.9 mmol). Stir at 0° C. 8 h, and allow to warm over 18 h. Add Na$_2$SO$_3$ (16.0 g) and EtOAc (100 ml). Stir 0.5 h, separate the organic, dry (MgSO$_4$), concentrate and chromatograph on silica to obtain the diol as a yellow oil.

Step 2: Treat the product of Step 1 with 1.0 equivalent TBS-Cl according to Preparation 34, Step 1, to obtain the TBS ether as a yellow oil.

Step 3: Methylate product of Step 2 with according to Preparation 22, Step 2, to obtain the methyl ether as a yellow oil.

Step 4: React the product of Step 3 with piperazine according to Preparation 5 and chromatograph on silica to obtain the title aryl-piperazine as a dark oil.

Similarly, employ AD-mix-α to obtain the enantiomer, Preparation 72-2, as a dark oil.

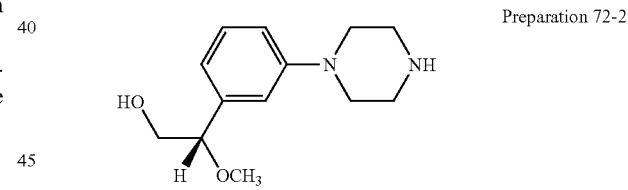

In similar fashion, from 4-bromostyrene, produce preparations 72-3 and 72-4.

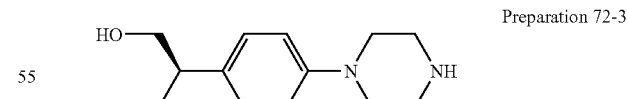

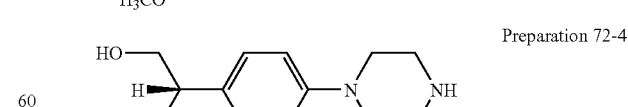

Treat the product of Step 3 above with piperazine under the conditions of Preparation 56, Step 3, to obtain Preparation 72-5 as a yellow oil.

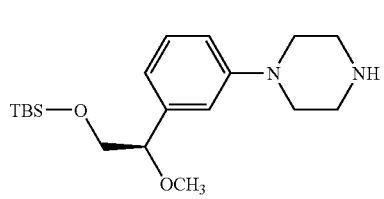

Preparation 73

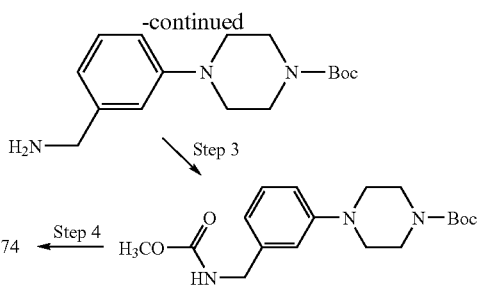

Step 1: Convert the product of Preparation 5-5 according to Preparation 17, Step 2, to the Boc-derivative.

Step 2: Reduce the Product of Step 1 with BH$_3$.Me$_2$S according to Preparation 48, Step 3, and chromatograph on silica to obtain the amine as a yellow oil.

Step 3: Cool to 0° C. the product of Step 2 (2.00 g, 6.9 mmol) and Et$_3$N (1.15 ml, 8.3 mmol) in THF (15 ml). Add methyl chloroformate (0.53 ml, 6.9 mmol). Stir at 0° C. 2 h, partition with EtOAc and sat. NaHCO$_3$, dry (MgSO$_4$), and concentrate to obtain the carbamate as a yellow oil.

Step 4: Deprotect the product of Step 3 according to Preparation 17, Step 8, to obtain the title aryl-piperazine as a yellow oil.

For Preparation 74-2, begin by converting 3-bromo-4-fluorobenzonitrile to 1-(3-cyano-6-fluorophenyl)piperazine according to Preparation 5. Convert this material according to the above procedures to obtain Preparation 74-2, a yellow oil.

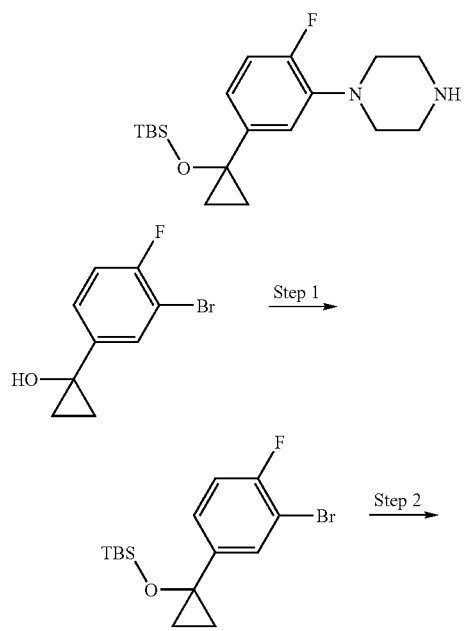

Convert the product of Preparation 71, Step 2, according to Preparation 34, Step 1, to obtain the TBS ether, then with piperazine under the conditions of Preparation 56, Step 3, to obtain the title aryl-piperazine as a yellow solid.

Preparation 74

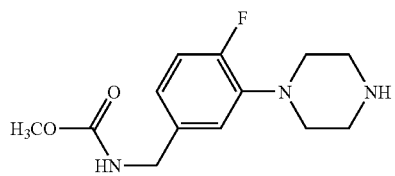

Preparation 75

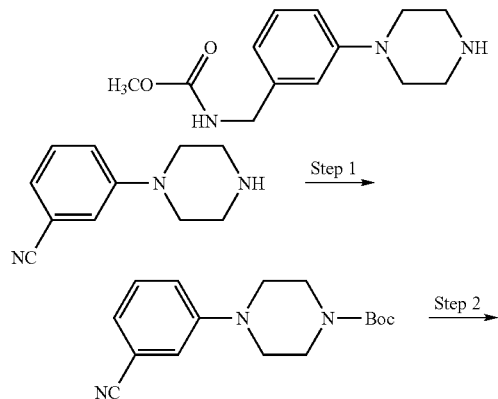

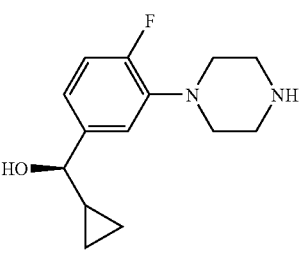

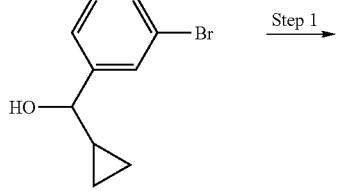

-continued

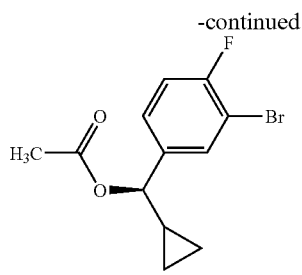

Step 2 → Preparation 75

Step 1: Combine the cyclopropyl carbinol intermediate of Preparation 69 (4.90 g, 20 mmol) with vinyl acetate (9.26 ml, 100 mmol) and Amano lipase C-II (2.50 g) in isopropyl ether (200 ml). Stir at 27° C. 18 h. Filter, concentrate, and chromatograph on silica to obtain the (R)-acetate (analysis via HPLC on Chiralcel OD) as a colorless oil.

Step 2: React the acetate of Step 1 with piperazine according to Preparation 5 and chromatograph on silica to obtain the title aryl-piperazine as a yellow oil.

Preparation 76

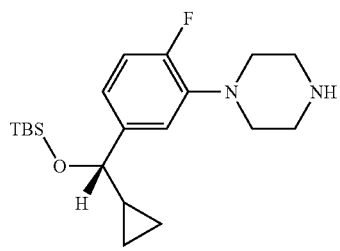

Treat the (S)-alcohol obtained by chromatography in Preparation 75, Step 1, according to the procedure of Preparation 56, Steps 2 and 3, to obtain the title aryl-piperazine as a yellow oil.

Preparation 77

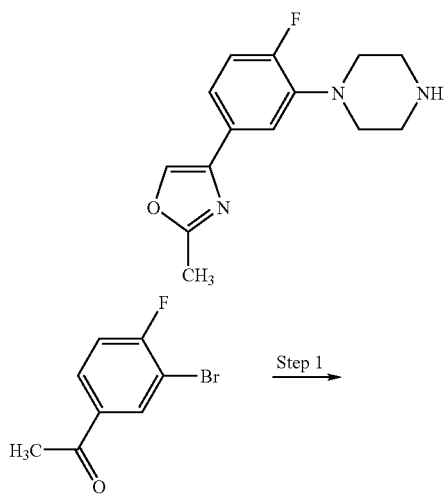

Step 1 →

-continued

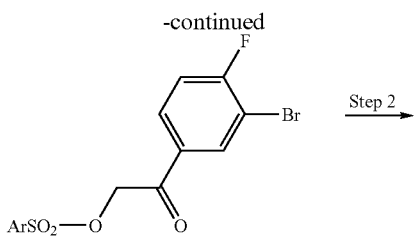

Step 2 →

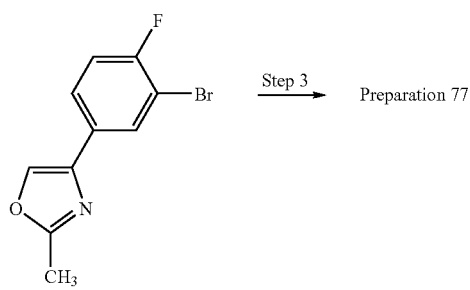

Step 3 → Preparation 77

Steps 1 and 2: Convert 3'-bromo-4'-fluoroacetophenone to the 2-(2,4-dinitrobenzene-sulfonyloxy) derivative according to the procedure of *Synth. Comm.* 2003, 1611, and react this with acetamide in CH$_3$CN (reflux 18 h) to give, after chromatography on silica, the oxazole as a white solid.

Step 3: React the product of Step 2 with piperazine according to Preparation 5 to obtain the title aryl-piperazine as a yellow oil.

In similar fashion, from 3'-bromo-4'-fluoropropiophenone, produce Preparation 77-2.

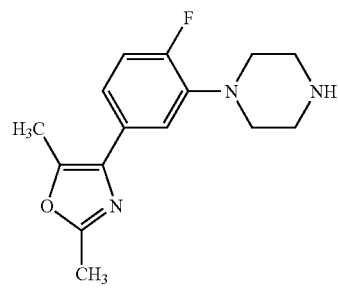

In similar fashion, from the ketone of Preparation 64, Step 2, produce Preparation 77-3.

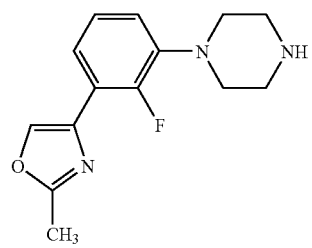

Preparation 78

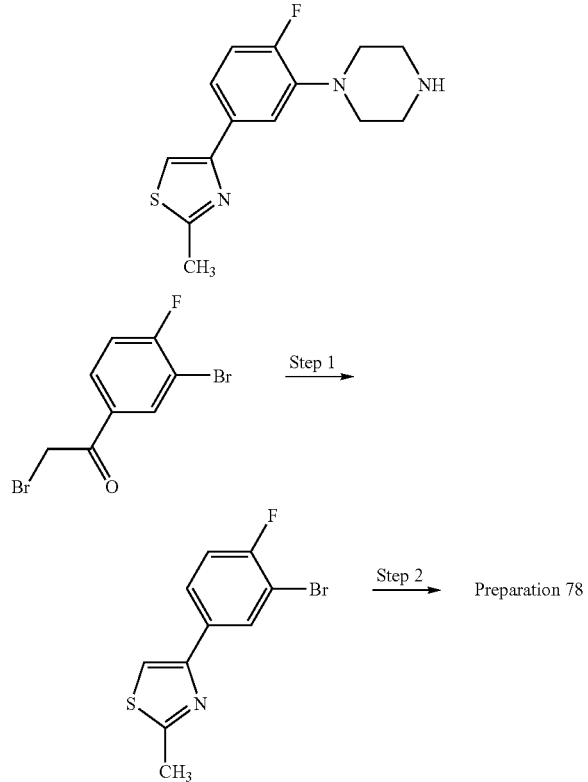

Step 1: Combine 2,3'-dibromo-4'-fluoroacetophenone (3.4 g, 11.5 mmol) and thioacetamide (1.00, 13.2 mmol) in dioxane and heat at 80° C. 2 h. Allow to cool, concentrate, and partition with ether and sat. NaHCO$_3$. Dry (MgSO$_4$), concentrate, and chromatograph on silica to obtain the thiazole as a yellow solid.

Step 2: React the product of Step 1 with piperazine according to Preparation 5 to obtain the aryl-piperazine as a yellow oil.

Preparation 79

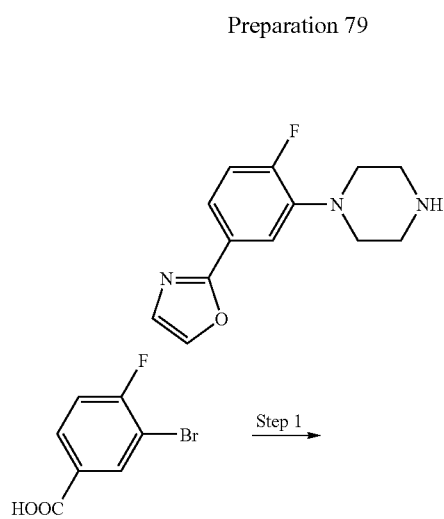

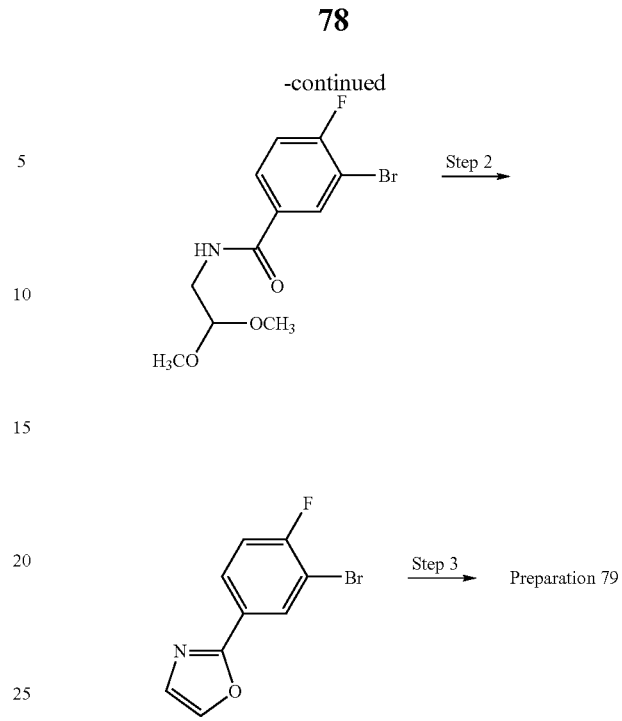

Step 1: To 3-bromo-4-fluorobenzoic acid (5.00 g, 22.8 mmol) in THF (100 ml) add isopropyl chloroformate (1.0M in toluene, 22.8 ml, 22.8 mmol), followed by N-methylmorpholine (2.76 ml, 25.1 mmol). Stri 1 h and add aminoacetaldehyde dimethyl acetal (2.49 ml, 22.8 mmol). Stir 0.75 h and partition with ether and satd. NaHCO$_3$. Dry (MgSO$_4$), and concentrate to obtain the amide as a yellow oil.

Step 2: Combine the product of Step 1 (3.75 g, 12.3 mmol) with Eaton's reagent (10% P$_2$O$_5$ in CH$_3$SO$_3$H, 30 ml). Heat at 110° C. 18 h, allow to cool, pour onto ice, and stir 0.5 h. Collect the solid to obtain the oxazole as a gray powder.

Step 3: React the product of Step 2 with piperazine according to Preparation 5 to obtain the aryl-piperazine as a yellow oil.

Preparation 80

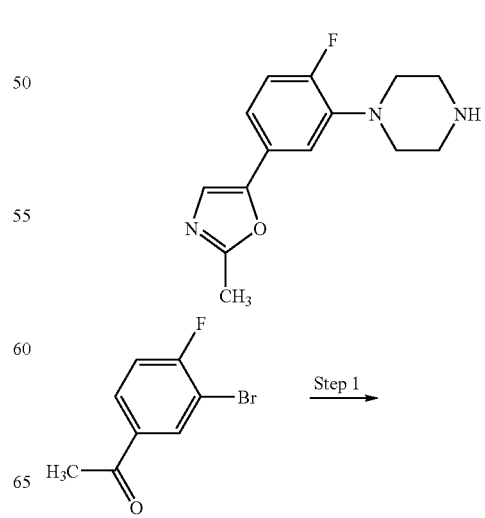

79

-continued

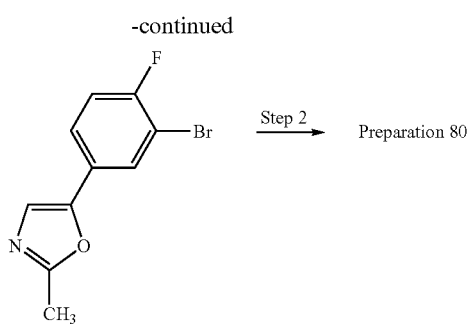

Step 1: To iodobenzene diacetate (5.34 g, 16.6 mmol) in acetonitrile (140 ml) add trifluoromethanesulfonic acid (5.5 ml, 62 mmol). Stir 30 min and add 3'-bromo-4'-fluoroacetophenone (3.00 g, 13.8 mmol). Heat at reflux 2 h, allow to cool, concentrate, and partition with EtOAc and satd. NaHCO$_3$. Dry (MgSO$_4$), concentrate, and chromatograph on silica to obtain the oxazole as a yellow oil.

Step 2: React the product of Step 1 with piperazine according to Preparation 5 to obtain the aryl-piperazine as a yellow solid.

Preparation 81

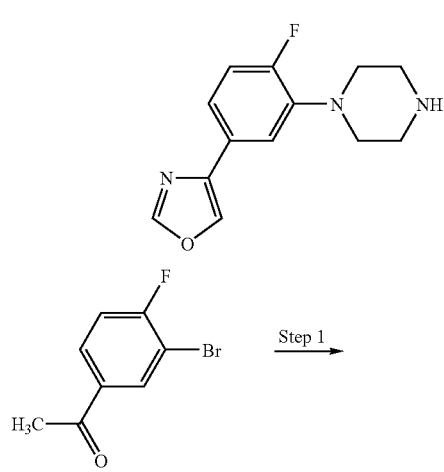

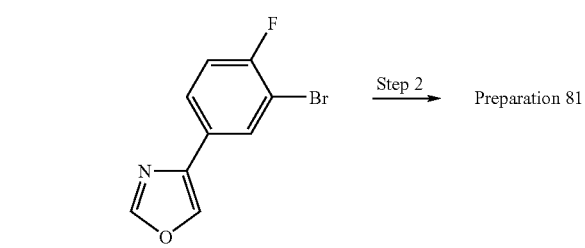

Step 1: To 3'-bromo-4'-fluoroacetophenone (3.50 g, 16.1 mmol) in formamide (10 ml) add bromine (0.83 ml, 16.1 mmol). Heat at 75° C. 2 h, then 135° C. 5 h. Allow to cool and partition with EtOAc and satd. NaHCO$_3$. Dry (MgSO$_4$), concentrate, and chromatograph on silica to obtain the oxazole as a yellow oil.

80

Step 2: React the product of Step 1 with piperazine according to Preparation 5 to obtain the title compound as a yellow oil.

Preparation 82

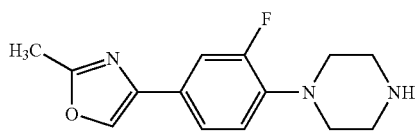

Steps 1 and 2: Convert 3'-fluoro-4'-methoxyacetophenone to the aryl-oxazole employing the method of Preparation 77, Steps 1 and 2.

Step 3: De-methylate the product of Step 2 with BBr$_3$ according to the method of Preparation 50, Step 3 to obtain the phenol as a yellow solid.

Step 4: Cool to −78° C. a solution of the product of Step 3 (1.73 g, 9.0 mmol) and Et$_3$N (2.5 ml, 7.9 mmol) in CH$_2$Cl$_2$ (50 ml). Add, dropwise, triflic anhydride (1.82 ml, 10.7 mmol). Stir 2 h, allow to warm to 0° C., wash with 1N NaOH (20 ml). Dry (MgSO$_4$) and concentrate to obtain the triflate as a yellow solid.

Step 5: Combine the product of Step 4 (1.70 g, 5.2 mmol), piperazine (2.7 g, 31.3 mmo), Cs$_2$CO$_3$ (2.55 g, 7.9 mmol), (±)-BINAP (0.20 g, 0.3 mmol), and Pd(OAc)$_2$ (0.047 g, 0.21 mmol) in DMF (20 ml). Heat at 90° C. 18 h, allow to cool, filter, and partition between EtOAc and 1N HCl. Basify the aqueous to pH 13, extract with CH$_2$Cl$_2$, dry (MgSO$_4$), and concentrate to obtain the title compound as a yellow solid.

Preparation 83

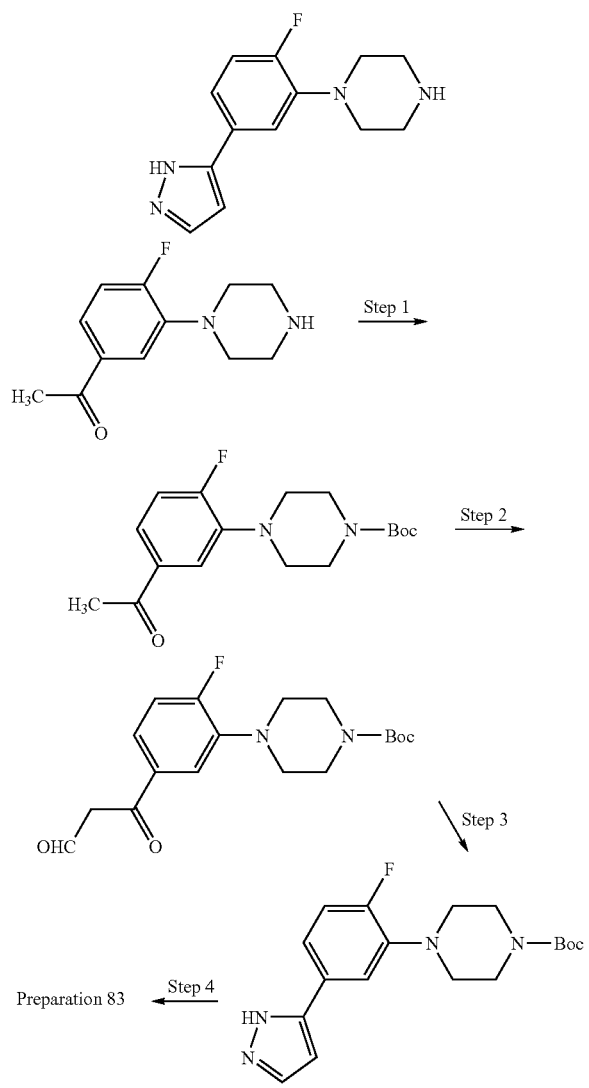

Step 1: Convert the product of Preparation 54 to the Boc-derivative according to Preparation 17, Step 2.

Step 2: Heat KO-tBu (1.00 g, 8.9 mmol) in THF (40 ml) to 50° C. and add dropwise a mixture of the product of Step 1 (2.00 g, 6.2 mmol) and ethyl formate (1.5 ml, 19 mmol) in THF (20 ml). After 2 h, allow to cool and partition between EtOAc and water. Wash the organic layer with 1N NaOH. Combine the aqueous layers and acidify to pH7-8 with NH$_4$Cl. Extract with EtOAc, dry (MgSO$_4$), and concentrate to obtain the crude formyl compound as a yellow solid.

Step 3: Combine the crude product of Step 2 (2.10 g, 6.0 mmol), hydrazine (0.28 ml, 9.0 mmol) and AcOH (0.69 ml, 12 mmol) in EtOH (30 ml). Heat at reflux 2 h and concentrate. Partition between EtOAc and 1N NaOH. Dry (MgSO$_4$), concentrate, and chromatograph on silica to obtain the pyrazole as a yellow solid.

Step 4: Deprotect according to Preparation 53, Step 5, and chromatograph on silica to obtain the piperazine as a yellow oil.

In similar fashion, treat the product of Step 1 with EtOAc (heat for 4 h) and continue as in Steps 3 and 4 to obtain Preparation 83-2 as a yellow solid.

Preparation 84

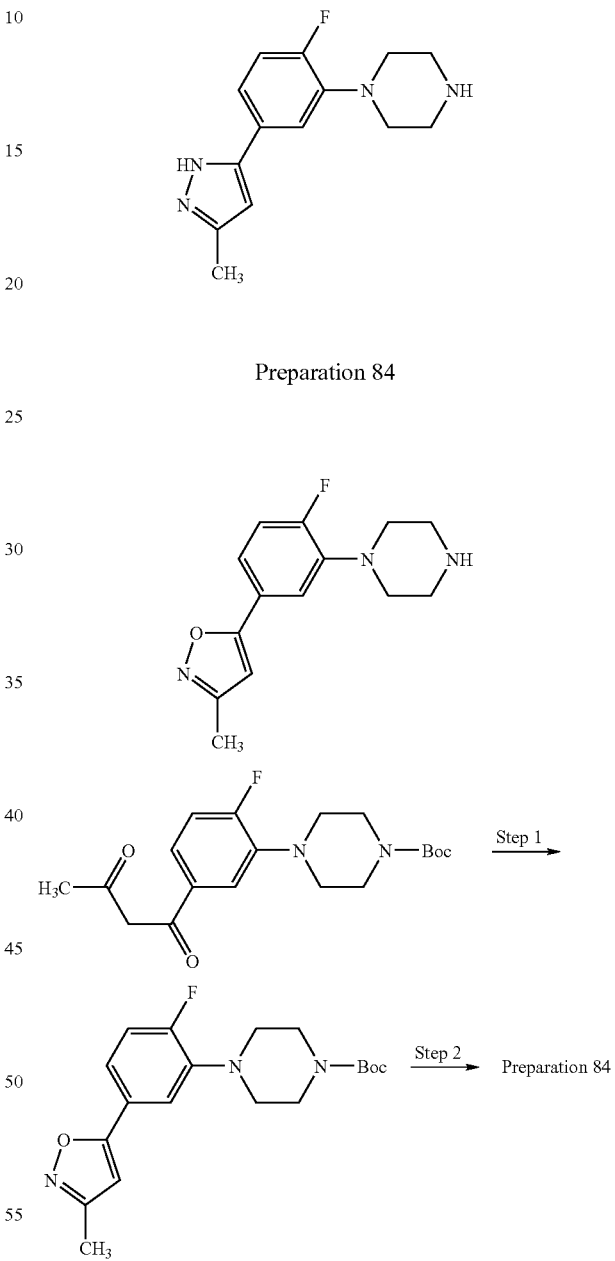

Step 1: Combine the diketone intermediate of Preparation 83-2 (1.50 g, 4.7 mmol) and hydroxylamine hydrochloride (0.66 g, 10.9 mmol) in EtOH (50 ml). Heat at reflux 5 h, allow to cool, concentrate, treat with 7N methanolic ammonia, concentrate, and chromatograph on silica to obtain the isoxazole as a yellow oil.

Step 2: Deprotect according to Preparation 53, Step 5, and chromatograph on silica to obtain the title compound as a yellow oil.

Preparation 85

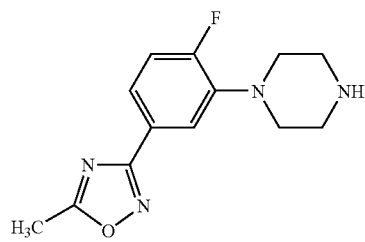

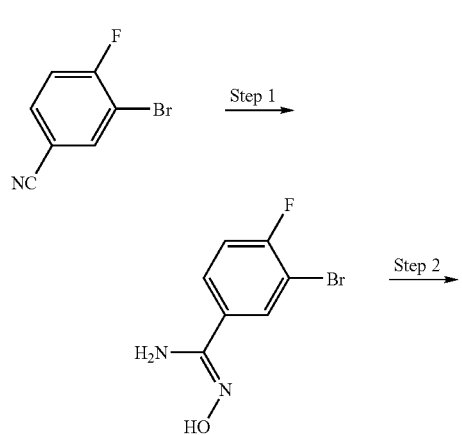

Step 1: To 3-bromo-4-fluorobenzonitrile (10 g, 50 mmol) in ethanol (125 ml) add Et$_3$N (16.1 ml, 115 mmol) and then hydroxylamine hydrochloride (7.64 g, 110 mmol). Heat to 75° C. and stir 24 h. Allow to cool, concentrate, and partition with EtOAc and water. Dry (MgSO$_4$) and concentrate to obtain the amide oxime as a white solid.

Step 2: To the product of Step 1 add acetic anhydride (20 ml). Heat at reflux for 2 h. Dilute with water, adjust pH to 8 with concentrated NH$_4$OH. Partition with Et$_2$O and water. Dry (MgSO$_4$) and concentrate to obtain the 1,2,4-oxadiazole as a white solid.

Step 3: React the product of Step 2 with piperazine according to Preparation 5 to obtain the title compound as a yellow oil.

Similarly, convert 3-bromobenzonitrile to Preparation 85-2.

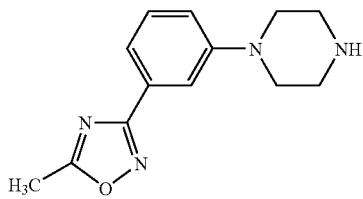

Preparation 86

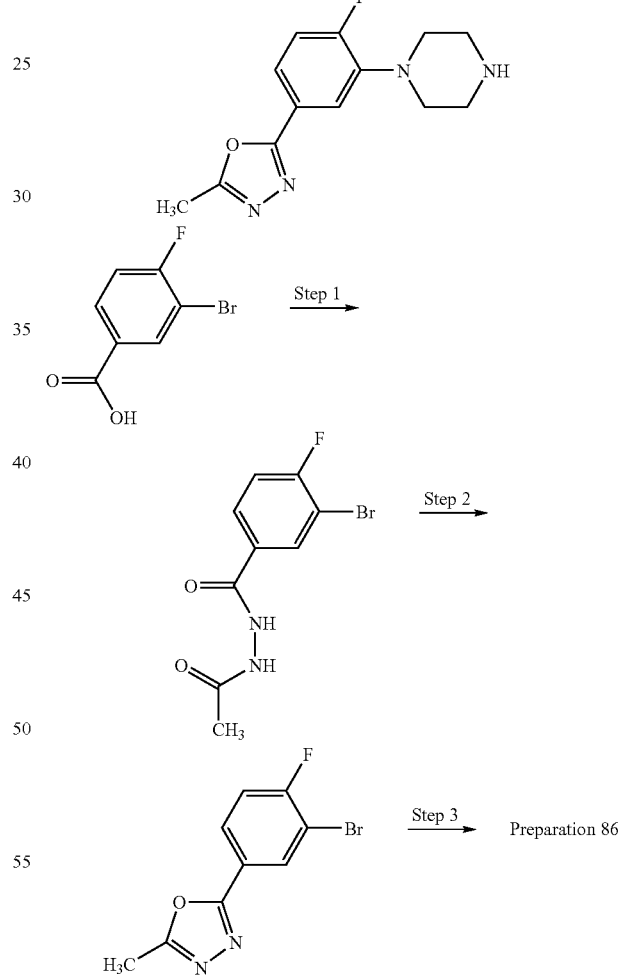

Step 1: To 3-bromo-4-fluorobenzoic acid (2.50 g, 110 mmol) in DMSO (35 ml) add acetic hydrazide (1.02 g, 13.7 mmol) and EDCl (2.63 g, 13.7 mmol), then HOBt.H$_2$O (1.85 g, 13.7 mmol). Stir 24 h. Partition with EtOAc and water. Dry (MgSO$_4$) and concentrate to obtain the hydrazide as a yellow oil.

Step 2: To the product of Step 1, add phosphorous oxychloride (30 ml). Heat at reflux 17 h, allow to cool, concentrate, and partition with EtOAc and water. Dry (MgSO₄), concentrate, and recrystallize with CH₂Cl₂/hexanes to obtain the 1,3,4-oxadiazole as a tan solid.

Step 3: React the product of Step 2 with piperazine according to Preparation 5 to obtain the title compound as a yellow solid.

Preparation 87

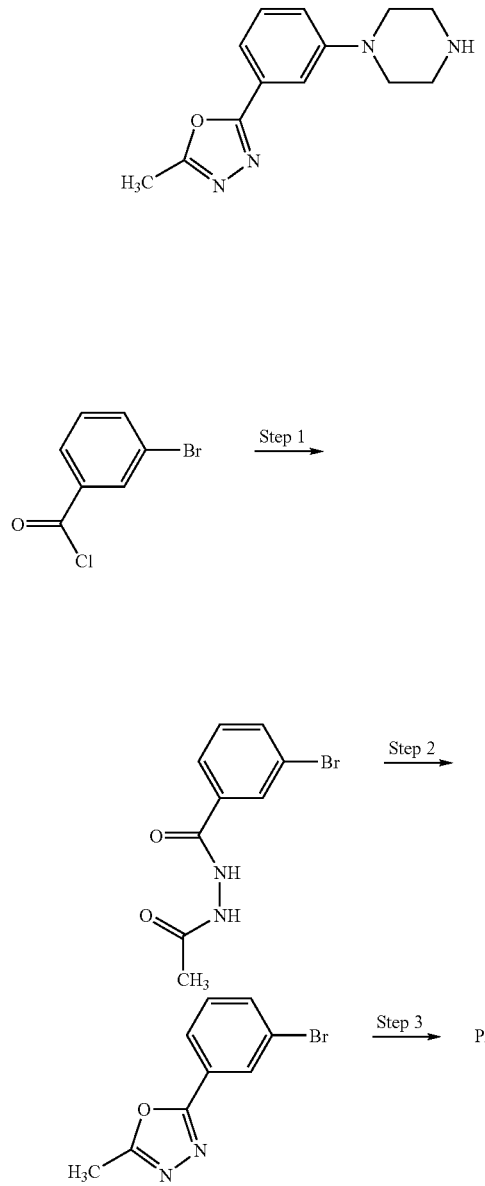

Step 3: React the product of Step 3 with piperazine according to Preparation 5 to obtain the title compound as a yellow solid.

Preparation 88

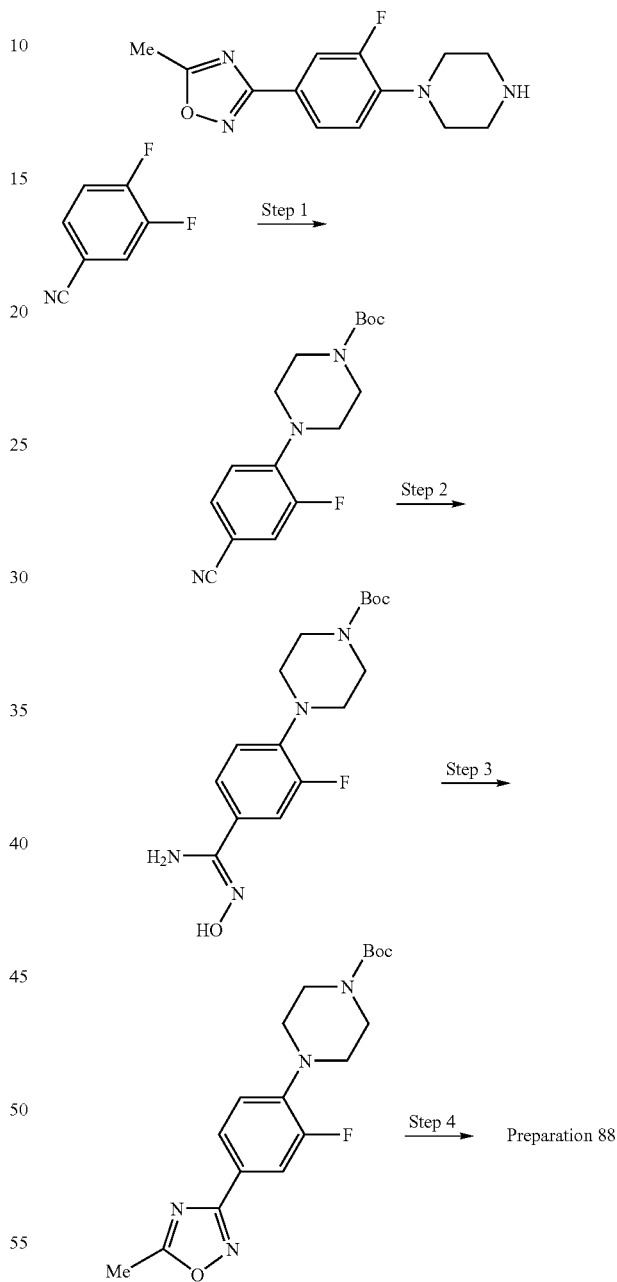

Step 1: To 3-bromobenzoyl chloride (5.0 g, 23 mmol) in CH₂Cl₂ (75 ml) at 0° C. add pyridine (3.7 ml, 46 mmol) and acetic hydrazide (2.2 g, 30 mmol). Stir for 1 h. Partition with CH₂Cl₂ and satd. NaHCO₃. Dry (MgSO₄), concentrate to obtain the hydrazide as a white solid.

Step 2: React the product of Step 1 with phosphorus oxychloride according to Preparation 86, Step 2, to obtain the 1,3,4-oxadiazole as a white solid.

Step 1: To 3,4-difluorobenzonitrile (1.5 g, 11 mmol) in DMSO (25 ml) add tert-butyl piperazine-1-carboxylate (2.4 g, 13 mmol) and K₂CO₃ (2.2 g, 16 mmol). Heat to 110° C. and stir 24 h. Allow to cool and add water (300 ml). Filter, wash with water, and dry under vacuum to obtain the aryl-piperazine as a white solid.

Step 2: To the product of Step 1 (1.0 g, 3.3 mmol) in ethanol (12 ml) add Et₃N (1.0 ml, 7.5 mmol) and then hydroxylamine hydrochloride (0.50 g, 7.2 mmol). Heat to 75° C. and stir 24 h. Allow to cool, concentrate and partition with EtOAc and water. Dry (MgSO$_4$) and concentrate to obtain the amide oxime as a white solid.

Step 3: To the product of Step 2 add acetic anhydride (12 ml). Heat at reflux for 2 h. Dilute with water, adjust pH to 8 with NH$_4$OH. Partition with Et$_2$O and water. Dry (MgSO$_4$) and concentrate to obtain the 1,2,4-oxadiazole as a yellow solid.

Step 4: To the product of Step 3 (0.64 g, 1.8 mmol) in CH$_2$Cl$_2$ (15 ml) add TFA (1.4 ml, 17 mmol). Stir 4 h, adjust pH to 11 with NH$_4$OH, and partition with CH$_2$Cl$_2$ and water. Dry (MgSO$_4$) and concentrate to obtain the title compound as a white solid.

In similar fashion, with propionic anhydride in place of acetic anhydride, produce Preparation 88-2, a brown solid.

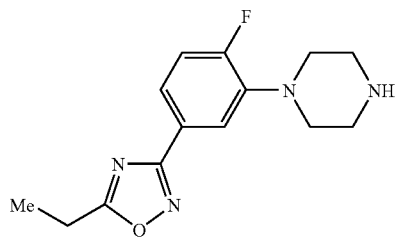

Preparation 89

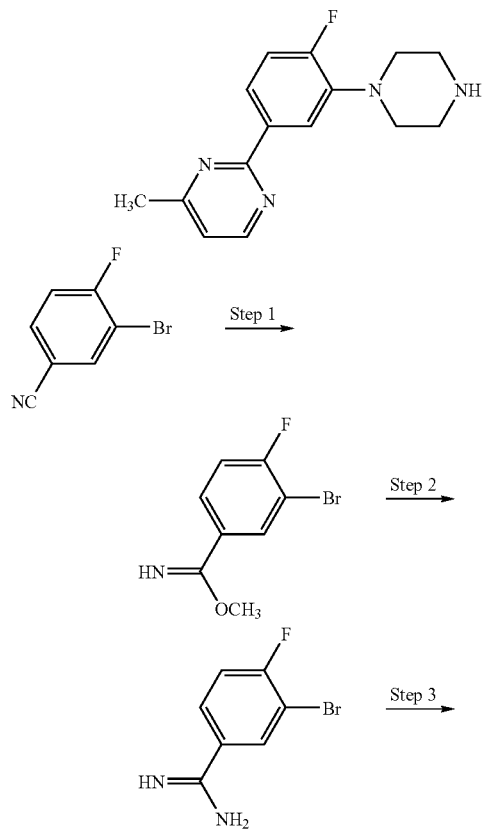

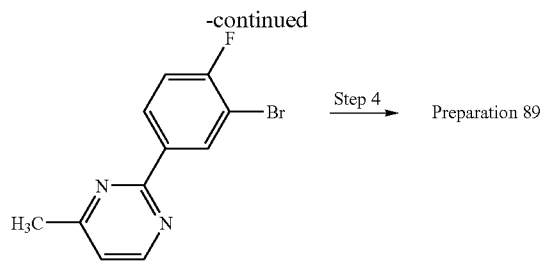

Step 1: Combine 3-bromo-4-fluorobenzonitrile (10.0 g, 50 mmol) with CH$_3$OH (4.8 g, 150 mmol) in ether (10 ml). Add 1.M HCl in ether (110 ml, 110 mmol) and keep at 5° C. 12 days. Filter to obtain the imidate hydrochloride as a white solid.

Step 2: Dissolve the product of Step 1 (1.85 g, 6.9 mmol) in 7M NH$_4$OH/CH$_3$OH (20 ml, 140 mmol). Keep at 5° C. 4 days and concentrate to give the amidine hydrochloride as a white solid.

Step 3: Combine the product of Step 2 (1.00 g, 3.9 mmol) and 4-methoxy-3-buten-2-one (0.48 g, 4.7 mmol) in CH$_3$OH (10 ml). Heat to 50° C. and add NaOMe (0.43 g, 7.9 mmol) in CH$_3$OH (5 ml). Heat 24 h, allow to cool, and concentrate. Dissolve in water, adjust to pH 7 with AcOH, and extract with CH$_2$Cl$_2$. Wash with brine, dry (MgSO$_4$), concentrate, and chromatograph on silica to obtain the pyrimidine as a white solid.

Step 4: React the product of Step 3 with piperazine according to Preparation 5 to obtain the title compound as a brown oil.

Preparation 90

Cool to −78° C. a solution of diisopropylamine (4.19 ml, 34.9 mmol) in THF (100 ml). Add slowly butyllithium (2.5M in hexanes, 12.9 ml, 32 mmol). Stir 40 min, add dropwise 2-furonitrile (4.9 ml, 27 mmol), and stir 1 h at −78° C. Add dry ice and stir 1 h at −78° C. 30 min. Allow to warm to RT and add water (150 ml). Extract with ether, then acidify the aqueous with conc. HCl to pH=2. Extract with ether, dry (MgSO$_4$), and concentrate to obtain the title acid as a yellow solid.

Preparation 91

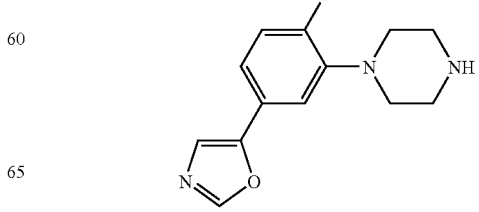

-continued

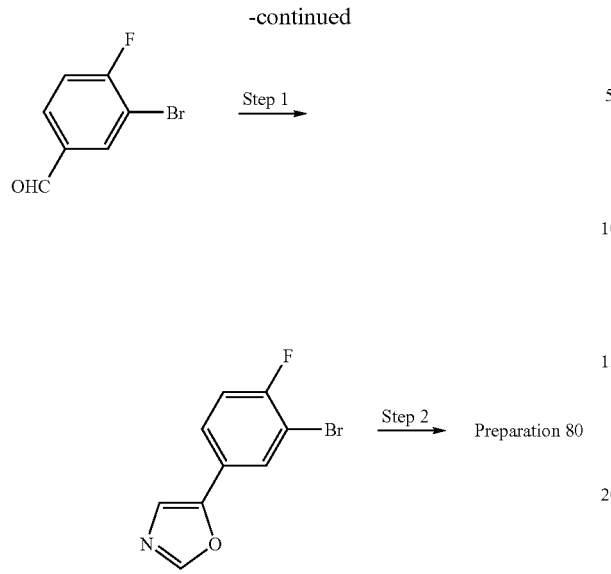

Step 1: To a solution of 3-bromo-4-fluorobenzaldehyde (4.90 g, 24 mmol) in MeOH (60 ml) add $K_2CO_3$ (6.66 g, 48 mmol) and toluenesulfonylmethyl isocyanate (5.42 g, 28 mmol). Heat at reflux 3 h, allow to cool, concentrate, and chromatograph on silica to obtain the oxazole as a yellow solid.

Step 2: React the product of Step 1 with piperazine according to Preparation 5 to obtain the title aryl-piperazine as a yellow oil.

Preparation 92

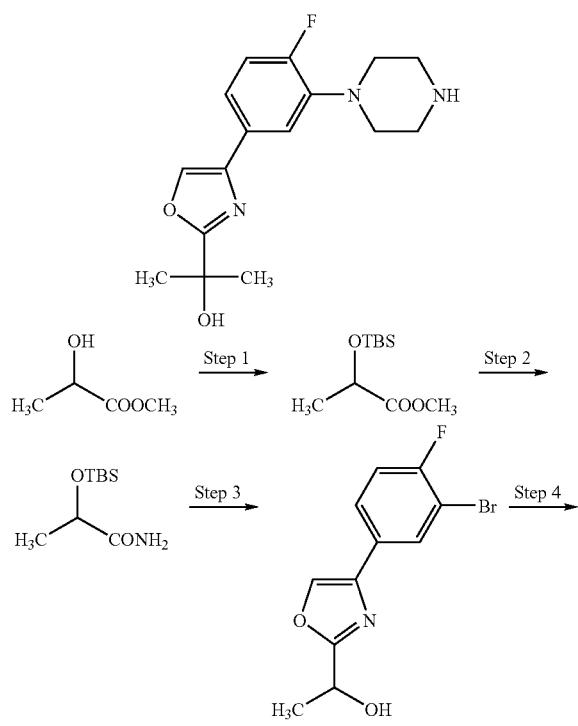

-continued

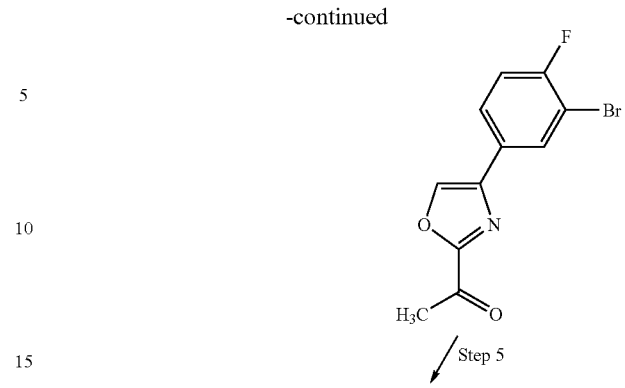

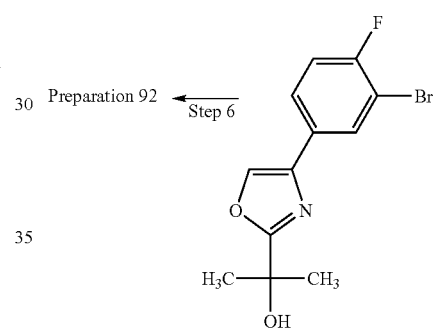

Step 1: To methyl (±)-lactate (8.0 g, 77 mmol) in THF (80 ml) add TBS-Cl (11.6 g, 77 mmol) and imidazole (6.3 g, 92 mmol). Stir 4 h and then heat at 50° C. 0.5 h. Allow to cool, add water and extract with ether. Dry ($MgSO_4$) and concentrate to obtain the crude product as a colorless oil.

Step 2: Combine the product of Step 2 with 7N $NH_3$/MeOH (40 ml) and heat at 50° C. 18 h. Allow to stand 3 days and concentrate to obtain the crude amide as a yellow oil.

Step 3: Combine the product of Step 2 (14.7 g, 72 mmol) with a solution of the product of Preparation 77, Step 1, from 6.0 g of the acetophenone. Heat at reflux 40 h, allow to cool, and add 7N $NH_3$/MeOH (20 ml). Concentrate and chromatograph on silica to obtain the oxazole as a yellow solid.

Step 4: Combine the product of Step 3 (1.8 g, 6.3 mmol) with pyridinium chlorochromate (6.8 g, 31 mmol) in $CH_2Cl_2$ (50 ml). Stir 18 h and add ether (100 ml). Filter through Celite, concentrate, and chromatograph on silica to obtain the ketone as a yellow solid.

Step 5: Cool a solution of the product of Step 4 (1.13 g, 4.0 mmol) in ether (25 ml) to 0° C. and add dropwise MeMgBr (3.0M in ether, 2.0 ml, 6.0 mmol). Stir 1 h and add 100 ml 8% $NH_4Cl$. Extract with ether and wash with $NaHCO_3$, then brine. Dry ($MgSO_4$) and concentrate to obtain the product as a white solid.

Step 6: React the product of Step 5 with piperazine according to Preparation 5 to obtain the title aryl-piperazine as a dark oil.

Preparation 93

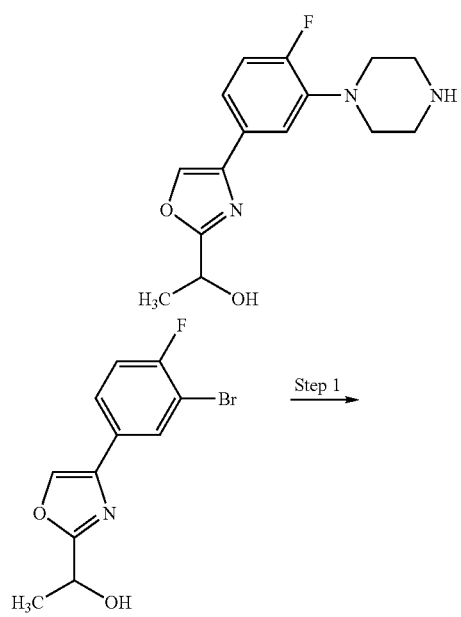

Step 1: Convert the product of Preparation 92, Step 3, to the TBS ether according to Preparation 92, Step 1.

Step 2: React the product of Step 1 with piperazine according to Preparation 5 to obtain the title aryl-piperazine as a yellow solid.

Preparation 94

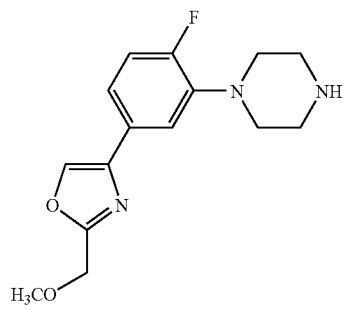

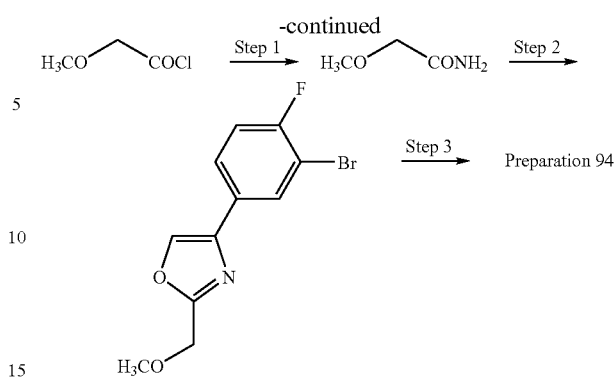

Step 1: To conc. NH$_4$OH (40 ml) cooled to 0° C. add dropwise methoxyacetyl chloride (10.0 g, 92 mmol). Stir 1 h, concentrate, treat with 9:1 ether/MeOH, filter, and concentrate to obtain the amide as a white solid.

Step 2: Treat the product of Step 1 with the sulfonyloxy-ketone as described in Preparation 92, Step 3. Concentrate and chromatograph on silica to obtain the oxazole as a yellow oil.

Step 3: React the product of Step 2 with piperazine according to Preparation 5 to obtain the title aryl-piperazine as a yellow oil.

Preparation 95

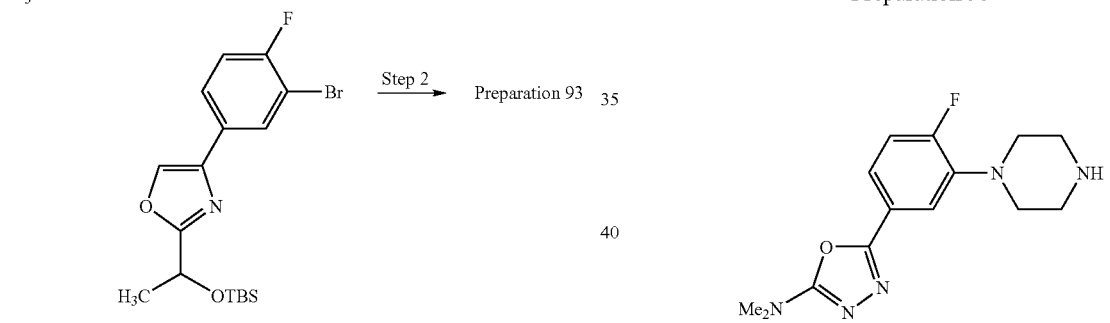

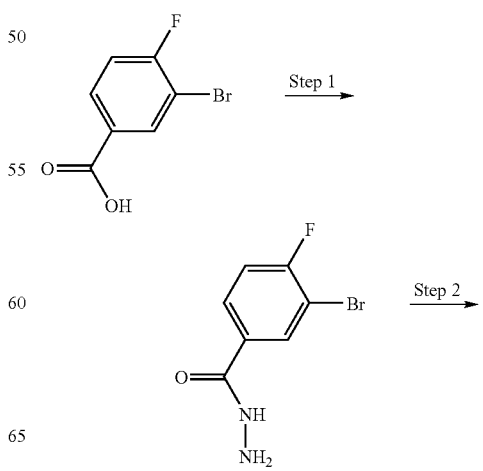

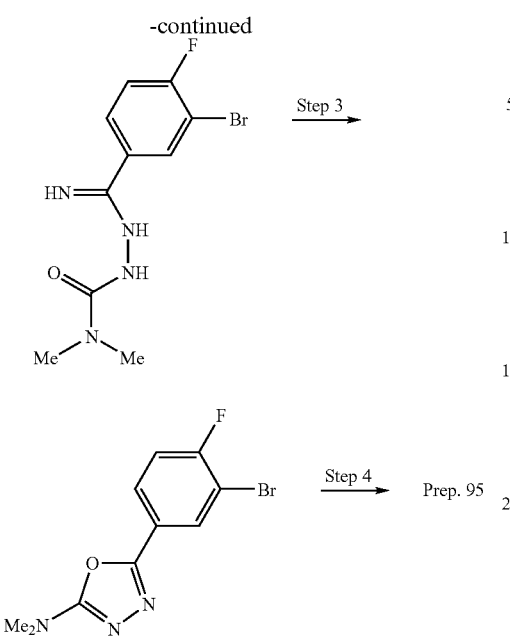

Step 1: To 3-bromo-4-fluorobenzoic acid (5.0 g, 22.8 mmol) in $CH_3CN$ (120 ml), add EDCl (5.25 g, 27.4 mmol), and $HOBt.H_2O$ (3.70 g, 27.4 mmol). Stir 2 h. Add the solution slowly over 15 min to a solution of hydrazine (1.43 ml, 45.7 mmol) in $CH_3CN$ (20 ml) at 0° C. Allow to warm and stir 1 h. Partition with EtOAc and water. Dry ($MgSO_4$) and concentrate to obtain the hydrazide as a white solid.

Step 2: To the product of Step 1 (1.00 g, 4.29 mmol) in $CH_2Cl_2$ (40 ml) add pyridine (0.52 ml, 6.44 mmol). Cool to 0° C. and add dimethylcarbamyl chloride (0.44 ml, 4.72 mmol), then THF (20 ml). Stir 4 h, allow to warm, and stir 12 h. Partition with $CH_2Cl_2$ and water. Dry ($MgSO_4$) and concentrate to obtain the hydrazide as a solid.

Step 3: To the product of Step 2 add phosphorous oxychloride (15 ml). Heat at reflux 5 h, allow to cool, concentrate, and partition with EtOAc and water. Dry ($MgSO_4$) and concentrate to obtain the 1,3,4-oxadiazole as an orange solid.

Step 4: React the product of Step 3 with piperazine according to Preparation 5 to obtain the title aryl-piperazine as a yellow oil.

Preparation 96

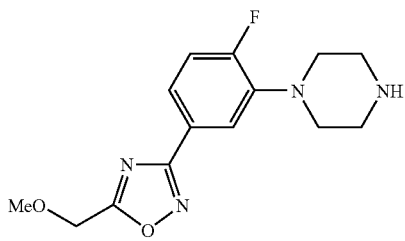

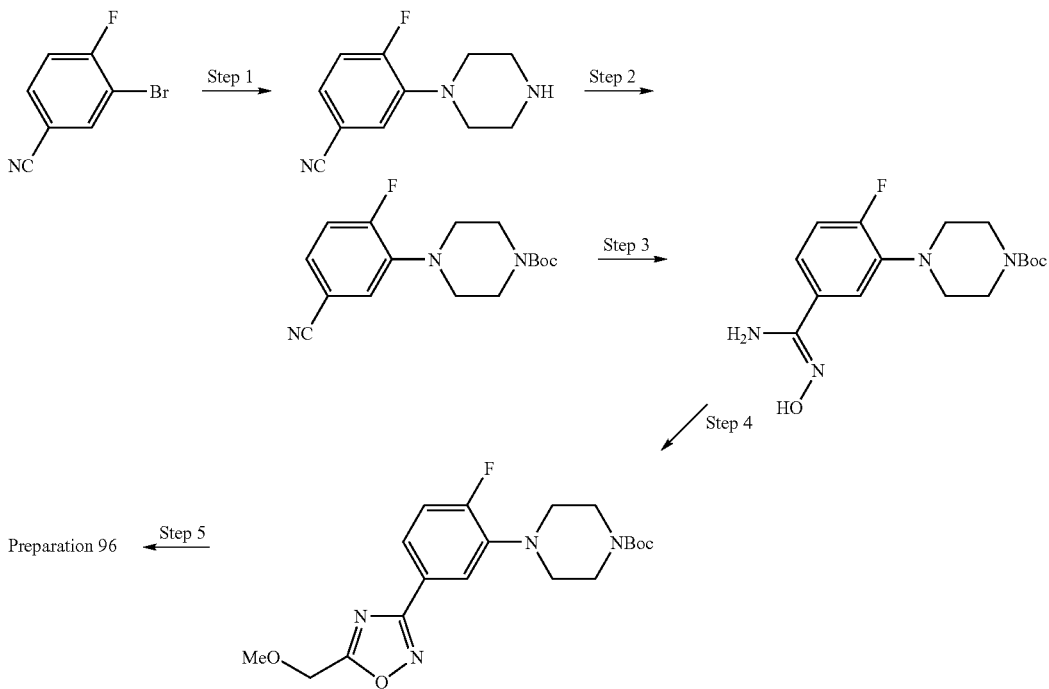

Step 1: React 3-bromo-4-fluorobenzonitrile with piperazine according to Preparation 5 to obtain the substituted piperazine as a brown oil.

Step 2: To the product of Step 1 (7.1 g, 35 mmol) in CH$_2$Cl$_2$ (175 ml) add Et$_3$N (9.7 ml, 69 mmol) and dimethylaminopyridine (1.1 g, 8.7 mmol), then di-tert-butyl dicarbonate (9.8 g, 45 mmol). Stir 24 h and partition with CH$_2$Cl$_2$ and water. Dry (MgSO$_4$) and concentrate to obtain the protected piperazine as a brown oil.

Step 3: To the product of Step 2 (10.0 g, 33 mmol) in ethanol (150 ml) add Et$_3$N (12 ml, 85 mmol) and hydroxylamine hydrochloride (5.7 g, 82 mmol). Heat at 75° C. 20 h and allow to cool. Add 1N HCl to adjust pH to 6, concentrate, and partition with EtOAc and water. Dry (MgSO$_4$) and concentrate to obtain the amide oxime as a yellow solid.

Step 4: To the product of Step 3 (0.79 g, 2.3 mmol) in pyridine (10 ml) add methoxyacetyl chloride (0.320 ml, 3.5 mmol). Heat at 110° C. 4 h and allow to cool. Partition with CH$_2$Cl$_2$ and water. Dry (MgSO$_4$) and concentrate to obtain the 1,2,4-oxadiazole as a brown oil.

Step 5: Deprotect according to Preparation 88, Step 4, and chromatograph on silica to obtain the title compound as a yellow oil.

Preparation 97

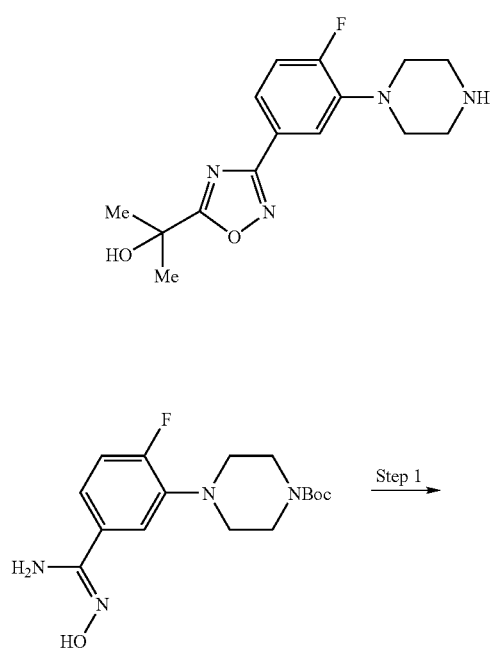

-continued

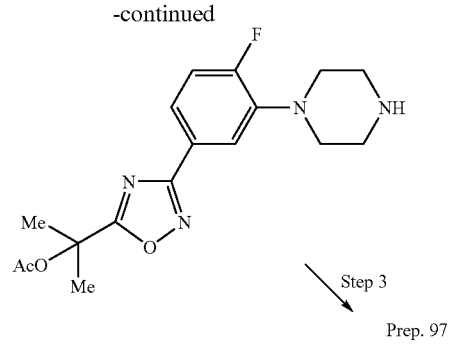

Step 1: To the product of Preparation 96, Step 3, (2.0 g, 5.9 mmol) in pyridine (20 ml) add 1-chlorocarbonyl-1-methylethyl acetate (1.1 ml, 7.7 mmol). Heat at 110° C. 18 h and allow to cool. Partition with CH$_2$Cl$_2$ and water. Dry (MgSO$_4$) and concentrate to obtain the 1,2,4-oxadiazole as a yellow oil.

Step 2: Remove the Boc group according to Preparation 88, Step 4, and chromatograph on silica to obtain the piperazine as an oil.

Step 3: To the product of Step 2 (0.40 g, 1.2 mmol) in MeOH (6 ml) add 1N NaOH (5.5 ml, 5.5 mmol) and stir 0.5 h. Concentrate, partition with EtOAc and water, dry (MgSO$_4$), and concentrate to obtain the title compound as a white solid.

Preparation 98

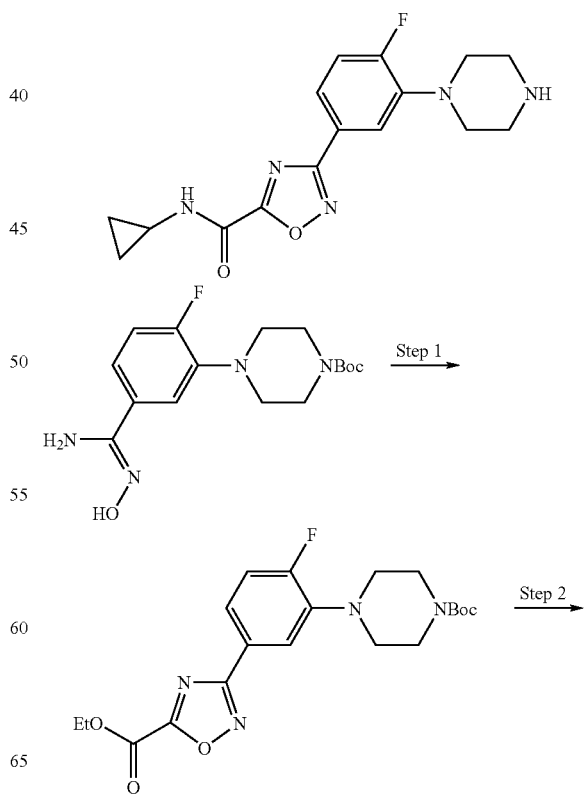

-continued

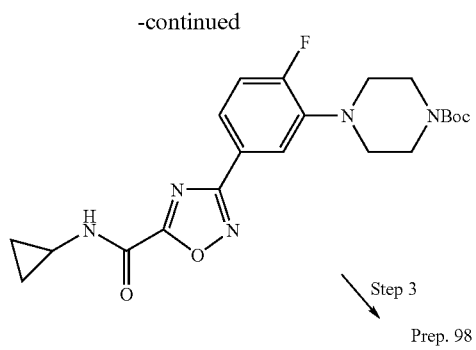

Step 3
Prep. 98

Step 1: To the product of Preparation 96, Step 3, (1.0 g, 3.0 mmol) in CH₂Cl₂ (15 ml) add pyridine (0.96 ml, 12 mmol), then ethyl oxalyl chloride (0.43 ml, 3.8 mmol). Stir 18 h and partition with CH₂Cl₂ and water. Dry (MgSO₄) and concentrate to obtain the 1,2,4-oxadiazole as a yellow oil.

Step 2: To the product of Step 1 (1.0 g, 2.4 mmol) in EtOH (12 ml) add cyclopropylamine (0.50 ml, 7.2 mmol). Heat at 80° C. 3 h, allow to cool, and concentrate to obtain the amide as a yellow oil.

Step 3: Deprotect according to Preparation 88, Step 4, and chromatograph on silica to obtain the title piperazine as a yellow solid.

Example 1

Combine the product of Preparation 2 (0.150 g, 0.34 mmol), the product of Preparation 8 (0.15 g, 0.77 mmol), and DIPEA (0.071 ml, 0.41 ml) in DMF (6 ml). Heat at 80° C. 18 h and allow to cool. Concentrate and triturate three times with MeOH. Filter to give the title compound as a yellow solid, MS m/e 474 (M+1).

In similar fashion, employing Preparation 2 together with the appropriate piperazine and purifying the crude product by PLC where necessary, produce the following compounds:

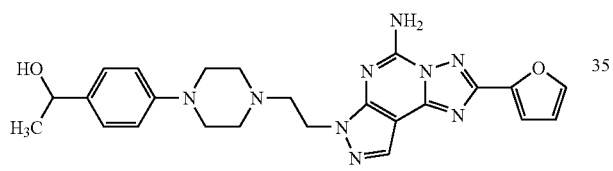

| Example | Z | MS m/e |
|---|---|---|
| 1-2 | OHC—⟨phenyl⟩— | 458 |
| 1-3 | HO—CH₂—⟨phenyl⟩— | 460 |
| 1-4 | morpholine-CH₂-⟨phenyl⟩- | 529 |
| 1-5 | H₃C-C(O)-NH-⟨3-F-4-Me-phenyl⟩ | 505 |
| 1-6 | H₃CN-piperazine-CH₂-⟨phenyl⟩- | 542 |
| 1-7 | H₃CO-CH₂CH₂-NH-C(O)-⟨phenyl⟩- | 549 |
| 1-8 | morpholine-C(O)-⟨phenyl⟩- | 561 |
| 1-9 | H₃CO-CH₂CH₂-O-CH₂-⟨phenyl⟩- | 518 |
| 1-10 | HO-CH₂CH₂-N(CH₃)-C(O)-⟨3-F-4-Me-phenyl⟩ | 549 |
| 1-11 | H₃CO-CH₂-⟨phenyl⟩- | 474 |
| 1-12 | NC-CH₂-⟨phenyl⟩- | 469 |

-continued

[Structure: piperazine-N-Z with ethylene linker to pyrazolo-triazolopyrimidine core bearing NH₂ and 2-furyl groups]

| Example | Z | MS m/e |
|---|---|---|
| 1-13 | H₃C—SO₂—NH—(3-F-4-methylphenyl) | 541 |
| 1-14 | H₂N-C(O)-CH₂-(4-methylphenyl) | 487 |
| 1-15 | 4-methylpiperazin-1-yl-C(O)-(3-F-4-methylphenyl) | 574 |
| 1-16 | 2-oxo-oxazolidin-3-yl-(4-methylphenyl) | 515 |
| 1-17 | H₃CO-CH₂-(3-F-4-methylphenyl) | 492 |
| 1-18 | H₃C-C(O)-(3-F-4-methylphenyl) | 490 |
| 1-19 | 7-methyl-3,4-dihydro-2H-1,5-benzodioxepin | 502 |
| 1-20 | 2-(methoxymethyl)-5-methyl-2,3-dihydrobenzofuran | 516 |

-continued

[Same core structure]

| Example | Z | MS m/e |
|---|---|---|
| 1-21 | H₃CO-CH₂CH₂-N(CH₃)-C(O)-(3-F-4-methylphenyl) | 563 |
| 1-22 | H₃C-C(O)-N(CH₃)-(3-F-4-methylphenyl) | 519 |
| 1-23 | H₃C-C(O)-NH-CH₂-(3-F-4-methylphenyl) | 519 |
| 1-24 | CH₃CH₂O-C(O)-N(CH₃)-(3-F-4-methylphenyl) | 549 |
| 1-25 | (CH₃)₃C-O-C(O)-(5-methyl-2,3-dihydroindol-1-yl) | 571 |
| 1-26 | CH₃CH₂O-C(O)-NH-CH₂-(3-F-4-methylphenyl) | 549 |
| 1-27 | NC-CH₂-(3-F-4-methylphenyl) | 487 |
| 1-28 | HO-CH₂-(3-F-4-methylphenyl) | 478 |
| 1-29 | H₃CO-CH₂-(4-F-3-methylphenyl) | 492 |

-continued

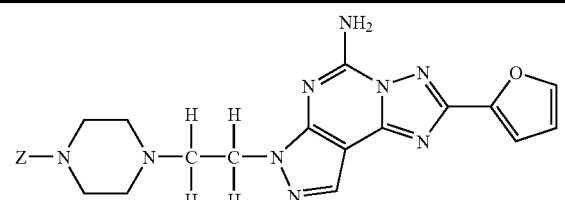

| Example | Z | MS m/e |
|---|---|---|
| 1-30 | 3-fluoro-4-methylphenyl-oxazolidin-2-one | 533 |
| 1-31 | 1-(3-fluoro-4-methylphenyl)pyrrolidin-2-one | 531 |
| 1-32 | 1-(3-fluoro-4-methylphenyl)-1-methoxyethyl | 506 |
| 1-33 | 2-methoxy-5-methylbenzyl methyl ether | 504 |
| 1-34 | 1,2-dimethoxy-1-(4-methylphenyl)ethyl | 514 |
| 1-35 | 2-hydroxy-1-methoxy-1-(4-methylphenyl)ethyl | 504 |
| 1-36 | 3,4-bis(methoxymethyl)toluene | 518 |
| 1-37 | 2-(4-methylphenyl)-1,3-dioxane | 516 |
| 1-38 | 3-fluoro-4-methylbenzyl 2-methoxyethyl ether | 536 |

-continued

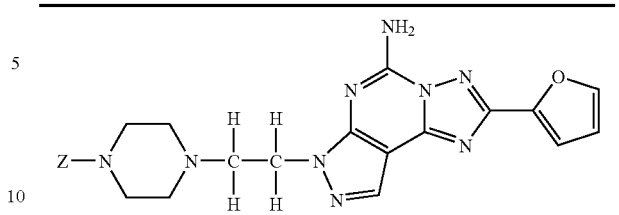

| Example | Z | MS m/e |
|---|---|---|
| 1-39 | 3-fluoro-4-methylbenzyl 2,2,2-trifluoroethyl ether | 560 |
| 1-40 | N-(3-fluoro-4-methylbenzyl)-N-methylacetamide | 533 |
| 1-41 | ethyl N-(3-fluoro-4-methylbenzyl)-N-methylcarbamate | 563 |
| 1-42 | (4-fluoro-3-methylphenyl)methanol | 478 |
| 1-43 | N-(3-fluoro-4-methylphenyl)-N-methylmethanesulfonamide | 555 |
| 1-44 | N-(3-fluoro-4-methylbenzyl)-N-methyl-2-methoxyacetamide | 549 |
| 1-45 | (4-fluoro-3-methylphenyl)acetonitrile | 487 |
| 1-46 | 3,5-bis(methoxymethyl)toluene | 518 |

-continued

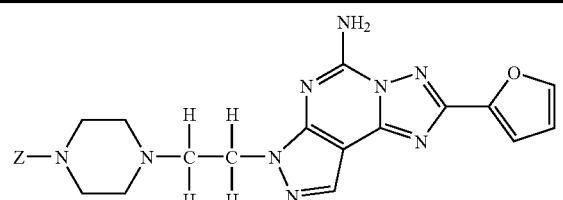

| Example | Z | MS m/e |
|---|---|---|
| 1-47 | 6-methyl-4-methoxychroman | 516 |
| 1-48 | H3CO-CH2-CH(NH-3-fluoro-4-methylphenyl)-CH2-OH | 551 |
| 1-49 | 1-(3-fluoro-4-methylphenyl)-2,2,2-trifluoroethanol | 546 |
| 1-50 | 1-(4-fluoro-3-methylphenyl)-1-methoxyethyl | 506 |
| 1-51 | ethyl 3-(3-fluoro-4-methylphenyl)propanoate | 548 |
| 1-52 | 1-(3-fluoro-4-methylphenyl)imidazolidin-2-one | 532 |
| 1-53 | 1-(3-fluoro-4-methylphenyl)-2,2,2-trifluoroethanone | 544 |
| 1-54 | 3-(3-fluoro-4-methylphenyl)-4-(hydroxymethyl)oxazolidin-2-one | 563 |

-continued

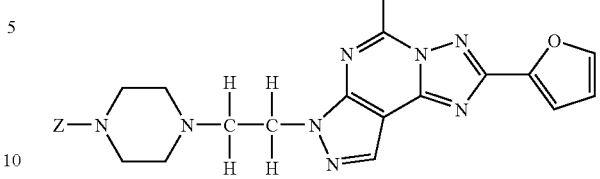

| Example | Z | MS m/e |
|---|---|---|
| 1-55 | 3-(3-fluoro-4-methylphenyl)-4-(methoxymethyl)oxazolidin-2-one | 577 |
| 1-56 | 1-(2,5-difluoro-4-methylphenyl)ethanone | 508 |
| 1-57 | 1-(3-fluoro-4-methylphenyl)-1-(pyrrolidin-1-yl)ethyl | 545 |
| 1-58 | (5-fluoro-2-methoxy-4-methylphenyl)methanol | 508 |
| 1-59 | 1-(2-(4-fluoro-3-methylphenyl)ethyl)cyclopropanol | 532 |
| 1-60 | 1-(4-methylphenyl)-2,2,2-trifluoroethanol | 528 |
| 1-61 | 1-(2,5-difluoro-4-methylphenyl)ethanol | 510 |

-continued
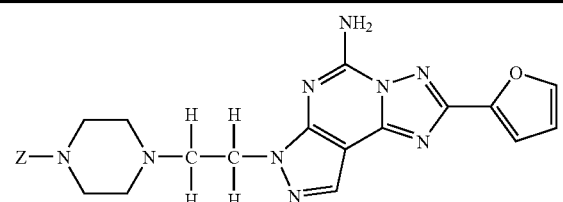
| Example | Z | MS m/e |
|---|---|---|
| 1-62 | 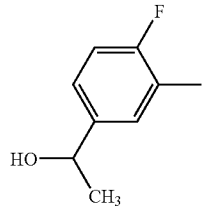 | 492 |
| 1-63 | 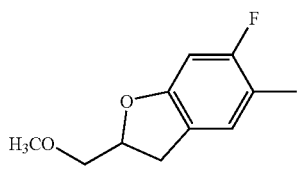 | 534 |
| 1-64 | 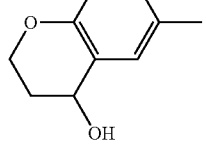 | 502 |
| 1-65 | 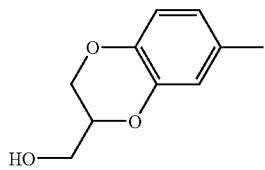 | 518 |
| 1-66 | 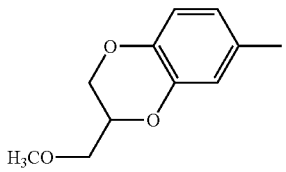 | 532 |
| 1-67 | 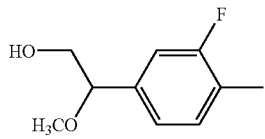 | 522 |
| 1-68 | 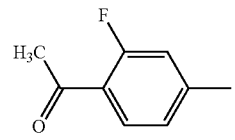 | 490 |
-continued
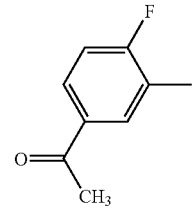
| Example | Z | MS m/e |
|---|---|---|
| 1-69 | 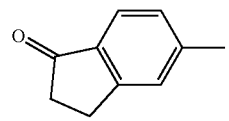 | 490 |
| 1-70 | 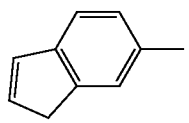 | 492 |
| 1-71 | 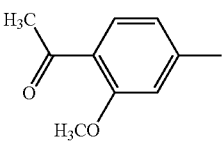 | 456 |
| 1-72 | | 468 |
| 1-73 | 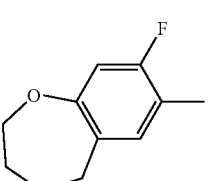 | 502 |
| 1-74 | 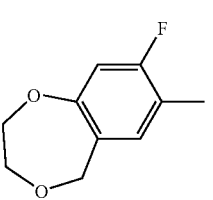 | 504 |
| 1-75 | | 520 |
| 1-76 | 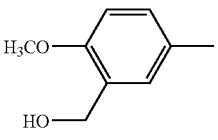 | 490 |

-continued
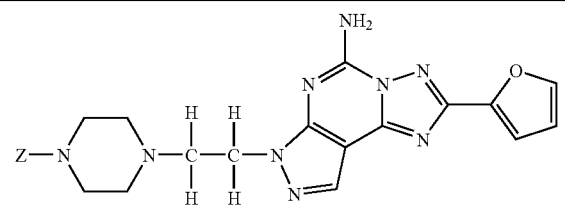
| Example | Z | MS m/e |
|---|---|---|
| 1-77 | 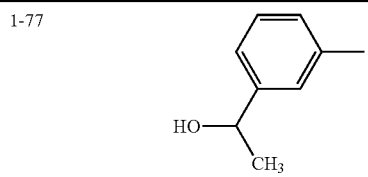 | 474 |
| 1-78 | 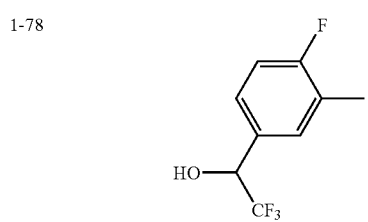 | 546 |
| 1-79 | 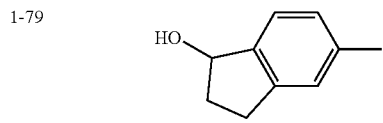 | 486 |
| 1-80 | 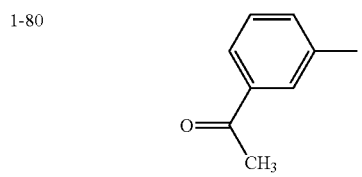 | 472 |
| 1-81 | 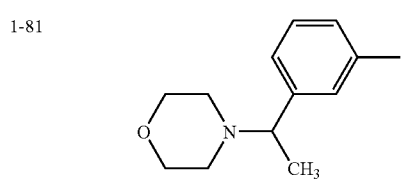 | 543 |
| 1-82 | 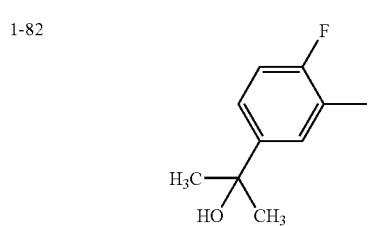 | 506 |
| 1-83 | 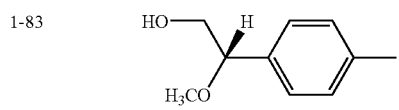 | 504 |
-continued
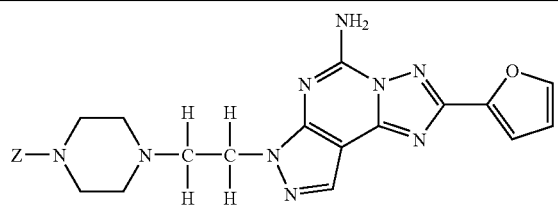
| Example | Z | MS m/e |
|---|---|---|
| 1-84 | 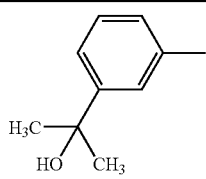 | 488 |
| 1-85 | 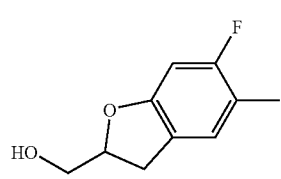 | 520 |
| 1-86 | 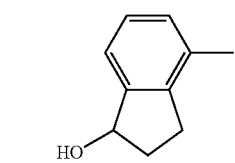 | 486 |
| 1-87 | 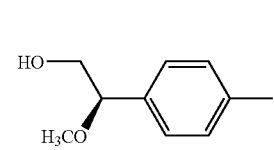 | 504 |
| 1-88 | 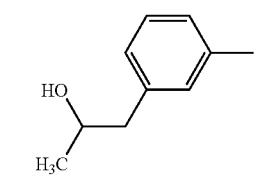 | 488 |
| 1-89 | 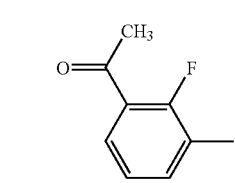 | 490 |
| 1-90 | 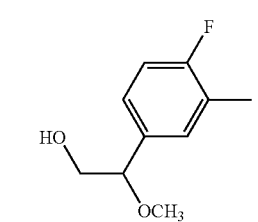 | 522 |

-continued
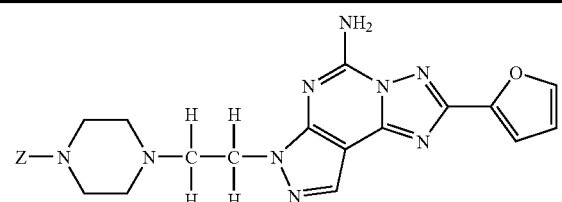
| Example | Z | MS m/e |
|---|---|---|
| 1-91 |  | 508 |
| 1-92 | 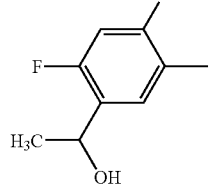 | 510 |
| 1-93 | 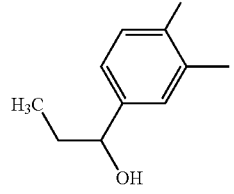 | 506 |
| 1-94 | 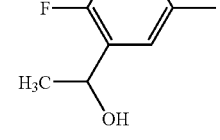 | 492 |
| 1-95 | 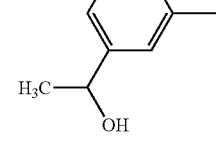 | 475 |
| 1-96 | 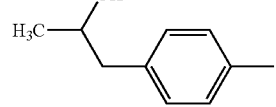 | 488 |
| 1-97 | 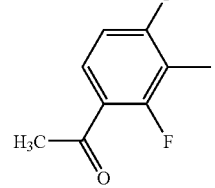 | 508 |
-continued
| Example | Z | MS m/e |
|---|---|---|
| 1-98 | 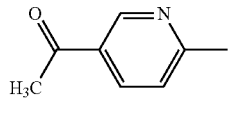 | 473 |
| 1-99 | 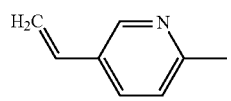 | 457 |
| 1-100 | 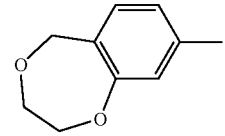 | 502 |
| 1-101 | 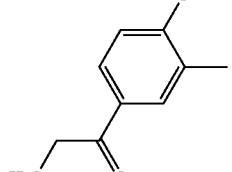 | 504 |
| 1-102 | 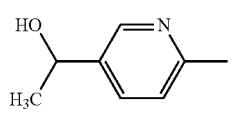 | 475 |
| 1-103 | 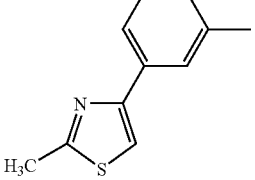 | 527 |
| 1-104 | 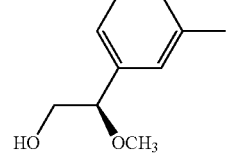 | 504 |
| 1-105 | 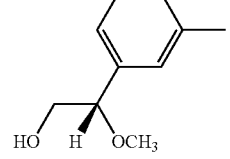 | 504 |

-continued
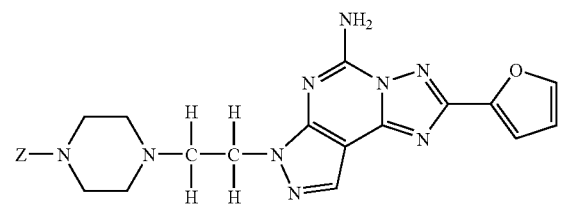
| Example | Z | MS m/e |
|---|---|---|
| 1-106 | 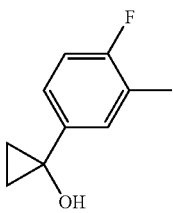 | 504 |
| 1-107 | | 473 |
| 1-108 | | 488 |
| 1-109 | | 502 |
| 1-110 | | 469 |
| 1-111 | | 517 |
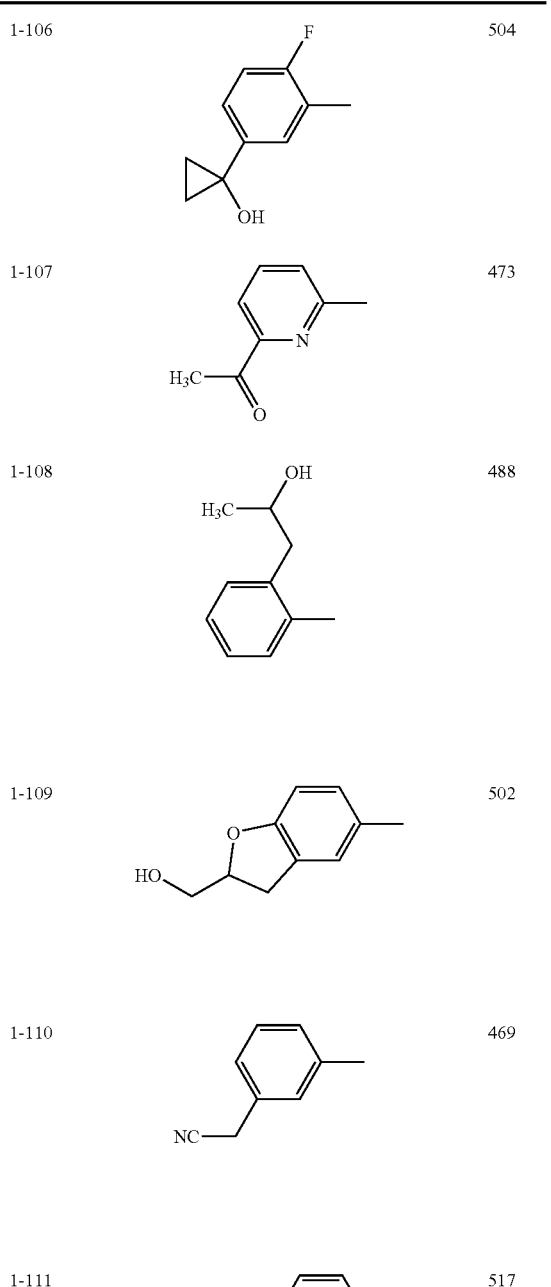
-continued
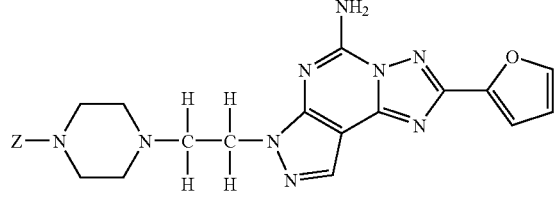
| Example | Z | MS m/e |
|---|---|---|
| 1-112 | | 535 |
| 1-113 | | 529 |
| 1-114 | | 545 |
| 1-115 | | 515 |
| 1-116 | | 529 |
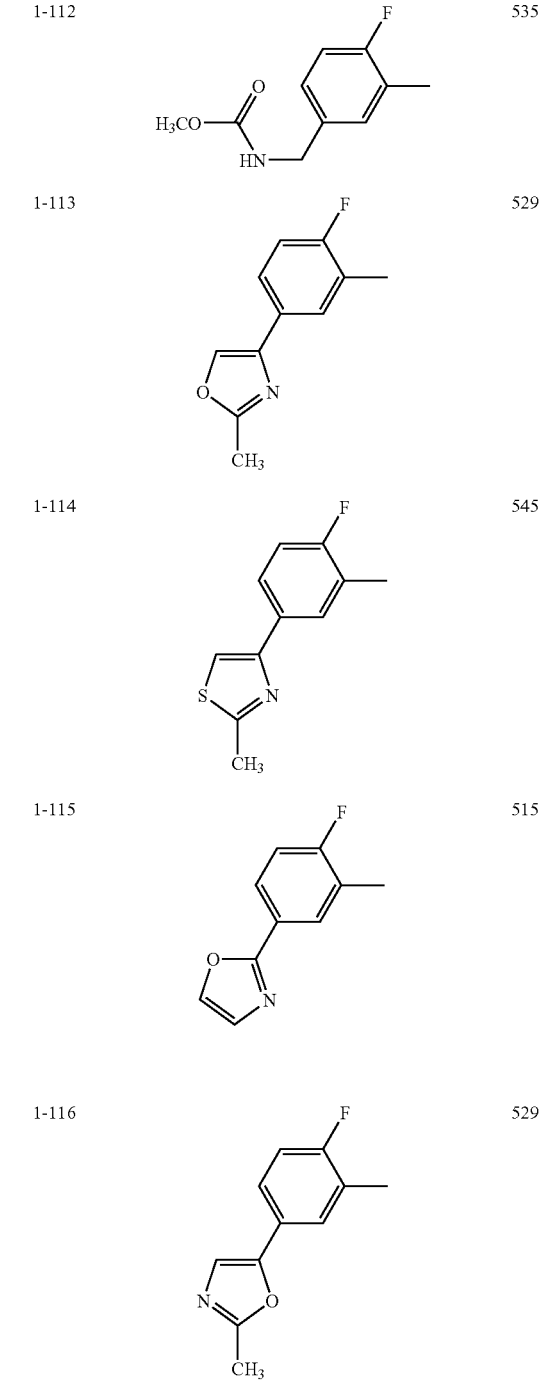

Example 2

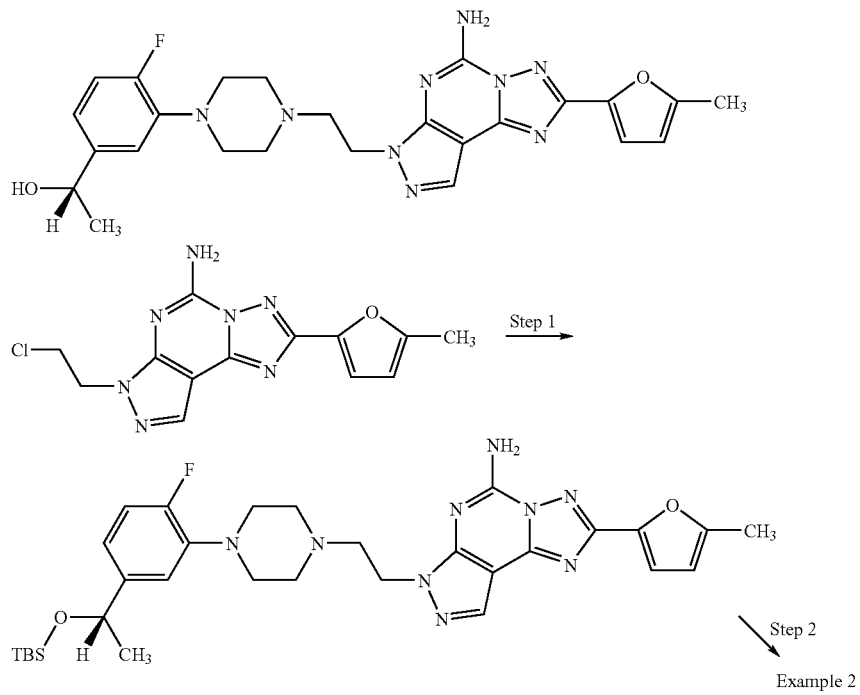

Step 1: Combine the product of Preparation 4 (0.173 g, 0.54 mmol), the product of Preparation 56 (0.367 g, 1.09 mmol) and KI (0.090 g, 0.55 mmol) in DMF (6 ml). Heat at 120° C. 24 h and concentrate. Purify by PLC to obtain the piperazine product as a yellow solid.

Step 2: To the product of Step 1 (0.149 g, 0.24 mmol) in THF (5 ml) add TBAF (1.0M in THF, 0.29 ml, 0.29 mmol). Stir 18 h and concentrate. Add MeOH (5 ml), stir, filter, and wash the solid with MeOH. Dry to obtain the title compound as an off-white solid, MS: m/e 506 (M+1).

In similar fashion, employing the appropriate chloride from Preparation 4 together with Preparation 56, prepare the following compounds:

| Example | R | MS m/e |
|---|---|---|
| 2-2 | 3-methylfuran | 492 |
| 2-3 | 2-methylthiophene | 508 |
| 2-4 | 5-methyl-2-bromofuran | 570, 572 |
| 2-5 | 3-cyanophenyl-methyl | 527 |
| 2-6 | 2-methylpyridine | 503 |

-continued

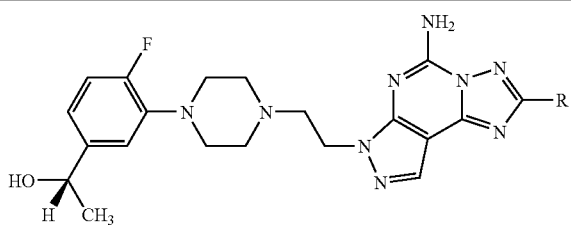

| Example | R | MS m/e |
|---|---|---|
| 2-7 | [5-methyl-oxazole] | 493 |
| 2-8 | [5-methyl-furan-2-CN] | 517 |
| 2-9 | [5-methyl-furan-2-CH3] | 506 |

Example 3

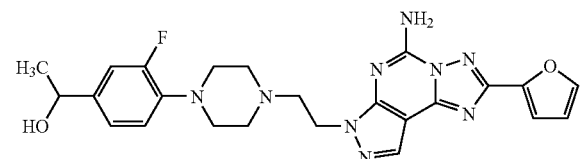

Treat the product of Preparation 4-5 with the product of Preparation 72-5 according to Example 2, Steps 1 and 2, to obtain the title compound as an off-white solid, MS: m/e 539 (M+1).

Example 4

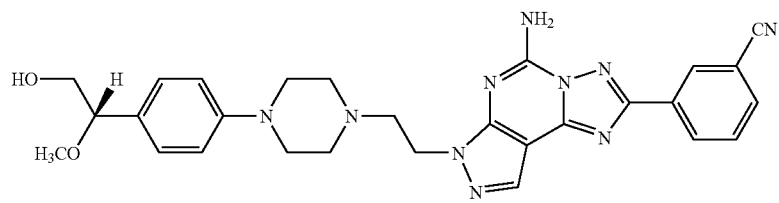

Dissolve the product of Example 1-18 (0.181 g, 0.37 mmol) in THF (30 ml). Add NaBH$_4$ (0.070 g, 1.8 mmol). Stir at RT 3 h, then 60° C. 2 h. Concentrate and add CH$_3$OH (10 ml). Filter to obtain the title compound as a yellow solid, MS: m/e 492 (M+1).

Example 5

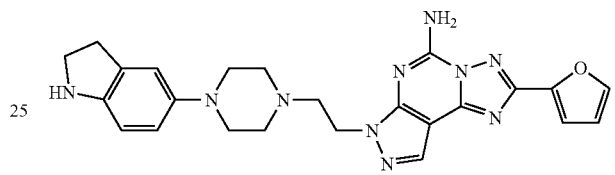

Dissolve the product of Example 1-25 (0.35 g, 0.62 mmol) in TFA (8 ml) cooled in an ice bath. Stir 1 h, concentrate, and treat the residue with 7N methanolic NH$_3$. Concentrate and purify by PLC to obtain the title compound as a yellow solid, MS: m/e 471 (M+1).

Example 6

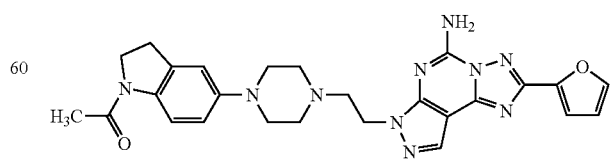

To the product of Example 5 (0.090 g, 0.19 mmol) in DMF (5 ml) add DIPEA (0.041 ml, 0.23 mmol) and acetic anhydride (0.022 ml, 0.23 mmol). Stir 2 h, concentrate, treat with MeOH and filter to obtain the title compound as a white solid, MS: m/e 513 (M+1)

Example 7

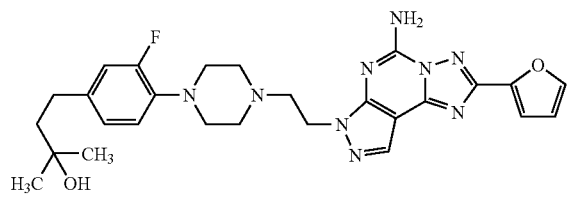

Treat Example 1-51 with methylmagnesium bromide according to Preparation 68 (THF solvent) and purify by PLC to obtain Example 7, a yellow solid, MS: m/e 534 (M+1).

Similarly, treat Example 1-53 with methylmagnesium bromide and purify by PLC to obtain Example 7-2, a yellow solid, MS: m/e 506 (M+1).

Example 7-2

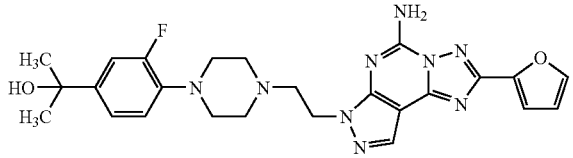

Similarly, treat the 2-fluoro analog of Example 1-2 (prepared analogously) with cyclopropylmagnesium bromide and purify by PLC to obtain Example 7-3, a yellow solid, MS: m/e 518 (M+1).

Example 7-3

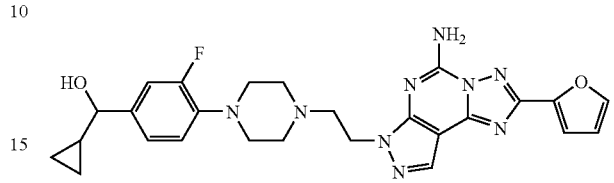

In similar fashion with isopropylmagnesium bromide prepare Example 7-4, a yellow solid, MS: m/e 520 (M+1).

Example 7-4

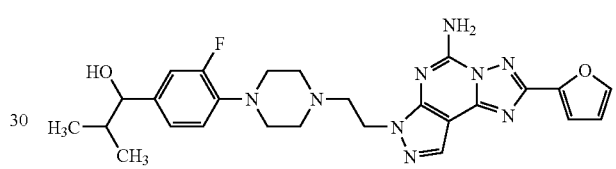

Example 8

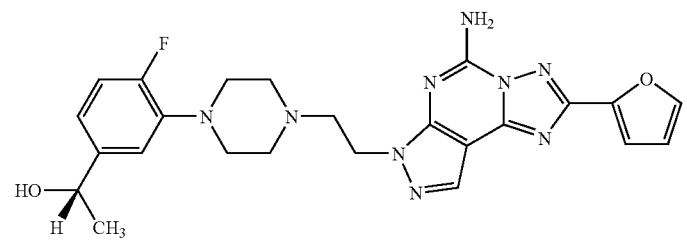

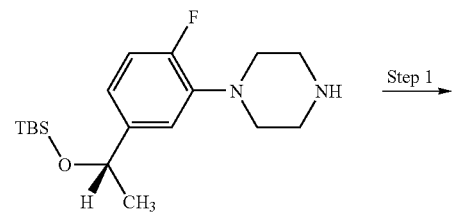

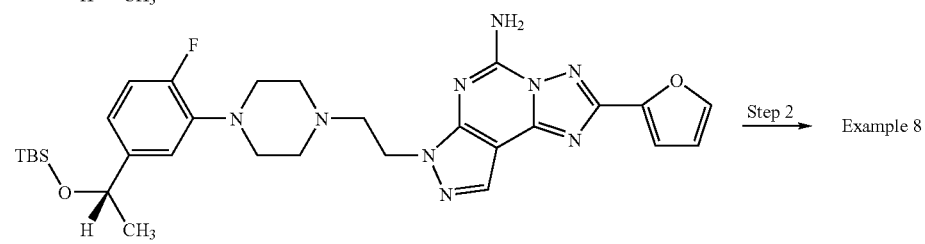

Step 1: Treat the product of Preparation 2 with the product of Preparation 56 according to the procedure of Example 1 to obtain the silyl ether as a yellow solid.

Step 2: Deprotect the product of Step 1 according to Example 2, Step 2, and purify by PLC to obtain the title compound as a white solid, MS: m/e 492 (M+1).

In similar fashion from Preparation 56-2 prepare the enantiomer, Example 8-2, also a white solid, MS: m/e 492 (M+1).

Example 8-2

From Preparation 69 prepare Example 8-3, a yellow solid, MS: m/e 518 (M+1).

ExampleS 8-3

From Preparation 70 prepare Example 8-4, a white solid, MS: m/e 522 (M+1).

Example 8-4

From the product of Preparation 69-2 prepare Example 8-5, a yellow solid, MS: m/e 500 (M+1).

Example 8-5

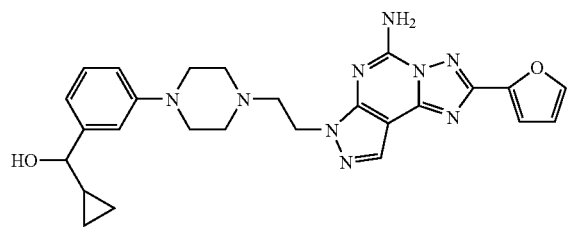

From Preparation 56-3 prepare Example 8-6, a yellow solid, MS: m/e 474 (M+1).

Example 8-6

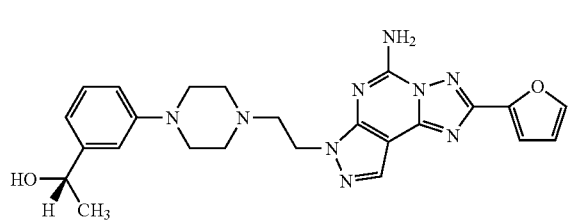

Likewise, from Preparation 56-4 prepare the enantiomer Example 8-7, also a yellow solid, MS: m/e 474 (M+1).

Example 8-7

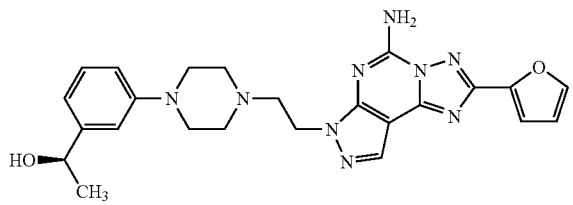

From the product of Preparation 75 (no TBS protection) prepare Example 8-8, a yellow solid, MS: m/e 518 (M+1).

Example 8-8

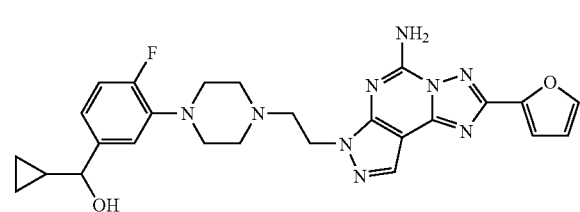

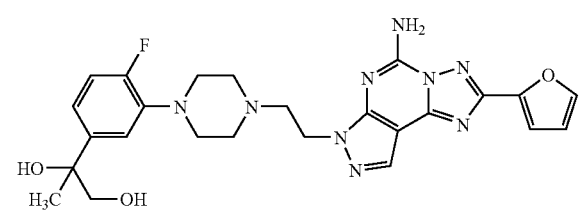

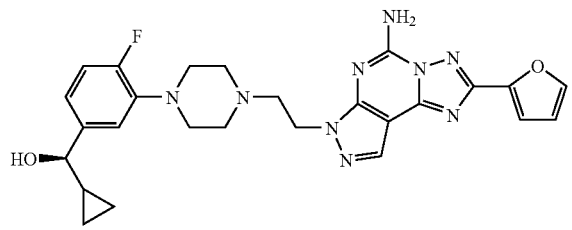

From the product of Preparation 76 prepare Example 8-9, a yellow solid, MS: m/e 518 (M+1).

Example 8-9

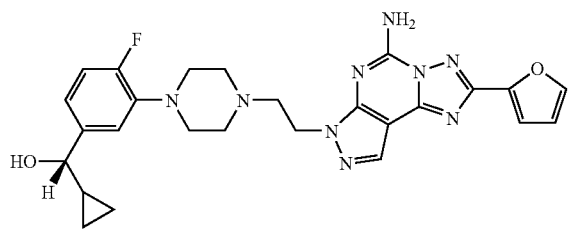

From Preparation 4-6 and Preparation 69, prepare Example 8-10, a yellow solid, MS: m/e 529 (M+1).

Example 8-10

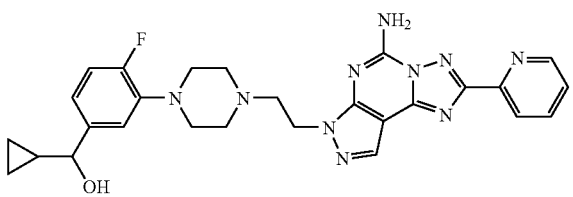

Example 9

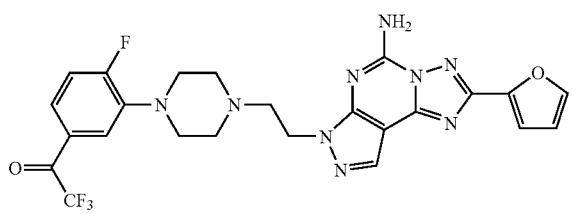

Oxidize the product of Example 1-78 with Dess-Martin periodinane in CH₂Cl₂. Purify the resulting ketone by PLC to give the title compound as a yellow solid, MS: m/e 544 (M+1).

Example 10

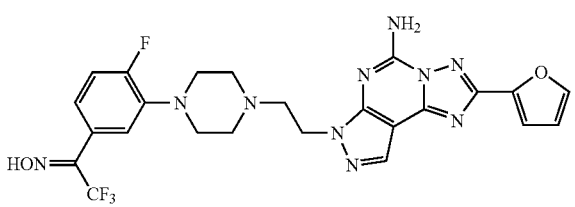

Treat the ketone of Example 9 with hydroxylamine hydrochloride in pyridine (60° C., 16 h). Purify by PLC to give the title compound as a yellow solid, MS: m/e 559 (M+1).

Example 11

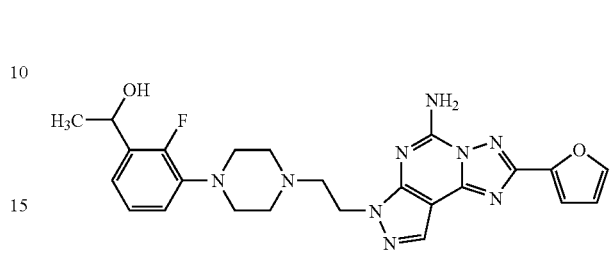

Reduce Example 1-89 according to Example 4. Purify by PLC to obtain the title compound as a white solid, MS: m/e 492 (M+1).

Similarly, from the product of Example 1-97 obtain Example 11-2 as a yellow solid, MS: m/e 510 (M+1).

Example 11-2

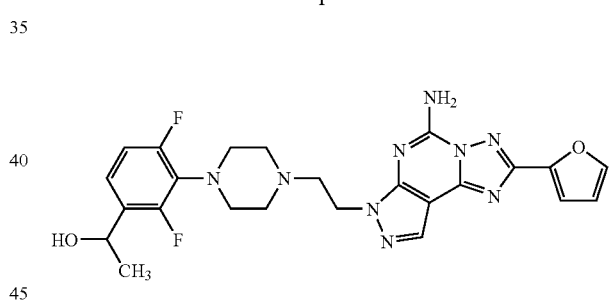

Similarly, from the product of Example 1-107 obtain Example 11-3 as a white solid, MS: m/e 475 (M+1).

Example 11-3

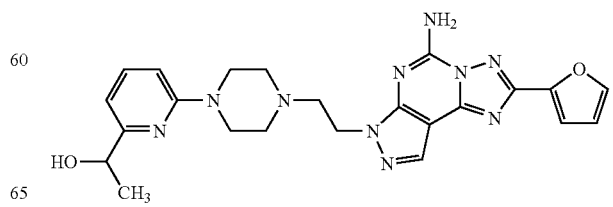

Example 12

In similar fashion to Example 2, Step 1, employ the appropriate chloride from Preparation 4 together with Preparation 80 to prepare the following compounds:

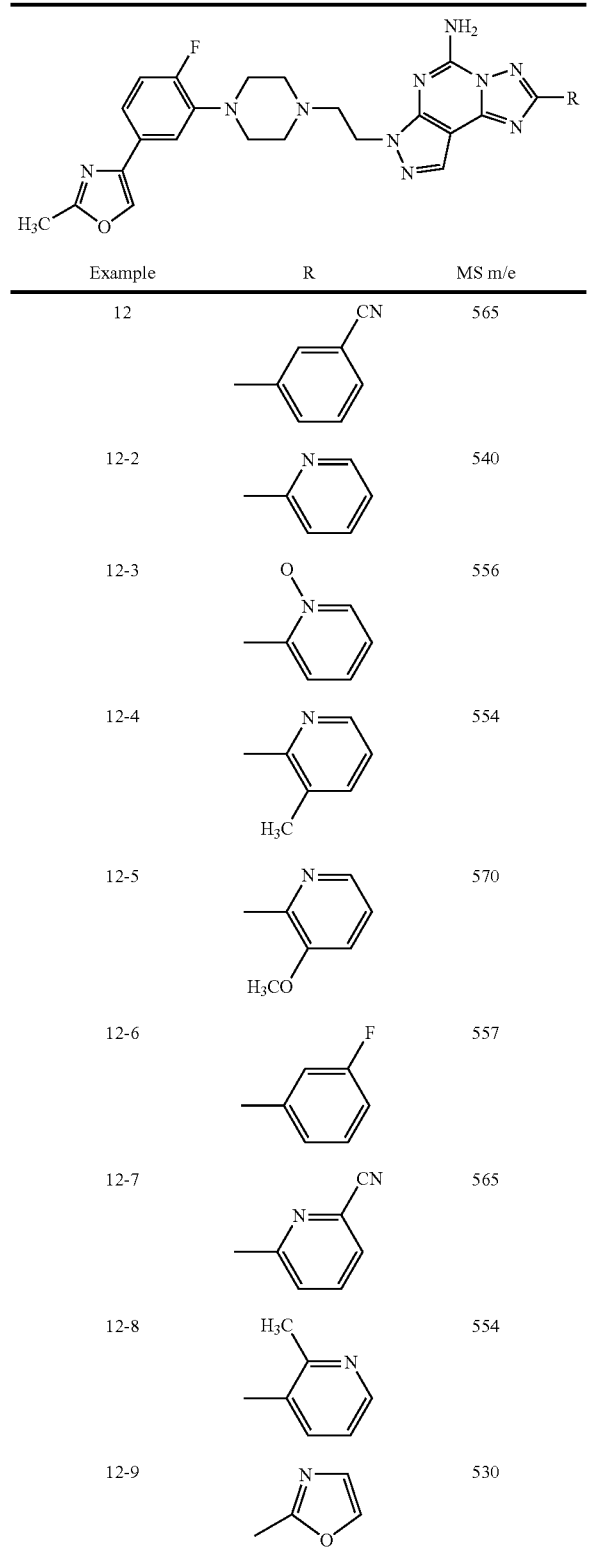

| Example | R | MS m/e |
|---|---|---|
| 12 | 3-cyanophenyl (CN, methyl) | 565 |
| 12-2 | 6-methylpyridin-2-yl | 540 |
| 12-3 | 6-methylpyridin-2-yl N-oxide | 556 |
| 12-4 | 2-methyl-3-methylpyridinyl | 554 |
| 12-5 | 2-methyl-3-methoxypyridinyl | 570 |
| 12-6 | 3-fluoro-5-methylphenyl | 557 |
| 12-7 | 6-methyl-2-cyanopyridinyl | 565 |
| 12-8 | 2,6-dimethylpyridin-3-yl | 554 |
| 12-9 | 2-methyloxazol-5-yl | 530 |

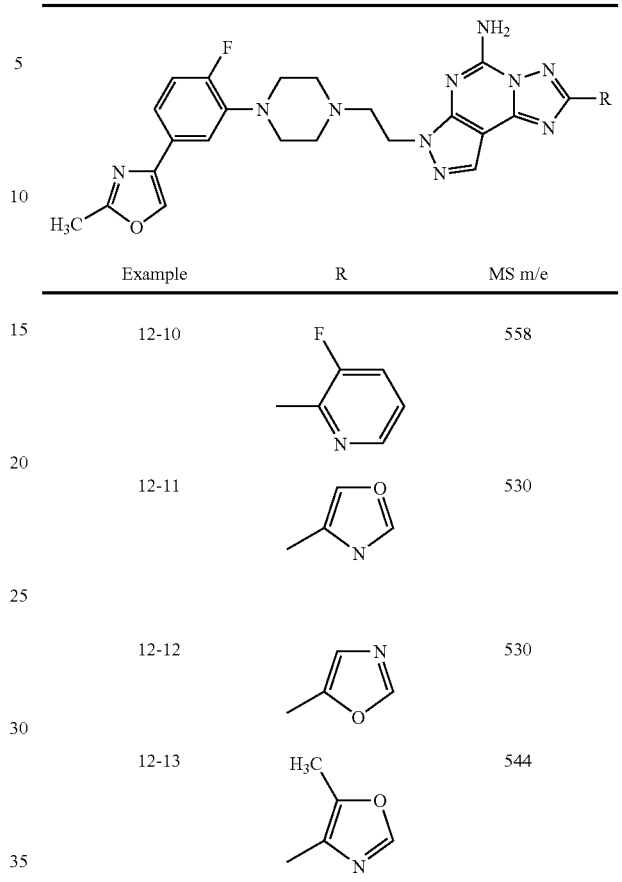

| Example | R | MS m/e |
|---|---|---|
| 12-10 | 3-fluoro-2-methylpyridinyl | 558 |
| 12-11 | 4-methyloxazol-5-yl | 530 |
| 12-12 | 2-methyloxazol-4-yl | 530 |
| 12-13 | 4,5-dimethyloxazolyl | 544 |

Employ the appropriate chloride from Preparation 4 together with Preparation 81 to prepare the following compounds:

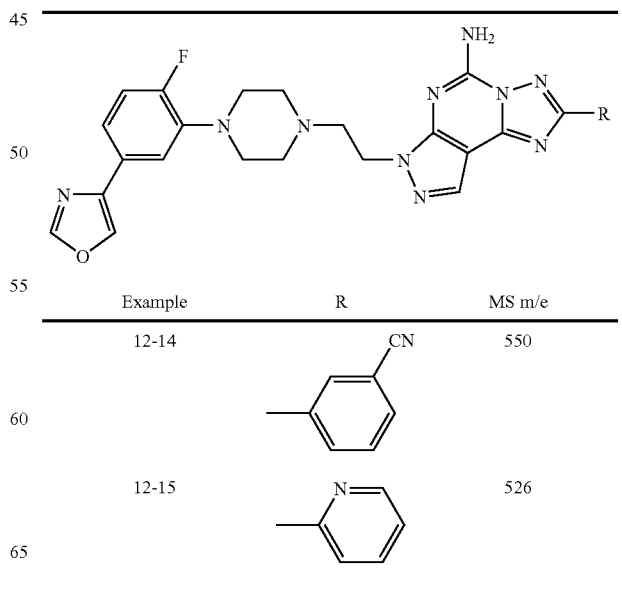

| Example | R | MS m/e |
|---|---|---|
| 12-14 | 3-cyano-5-methylphenyl | 550 |
| 12-15 | 6-methylpyridin-2-yl | 526 |

-continued

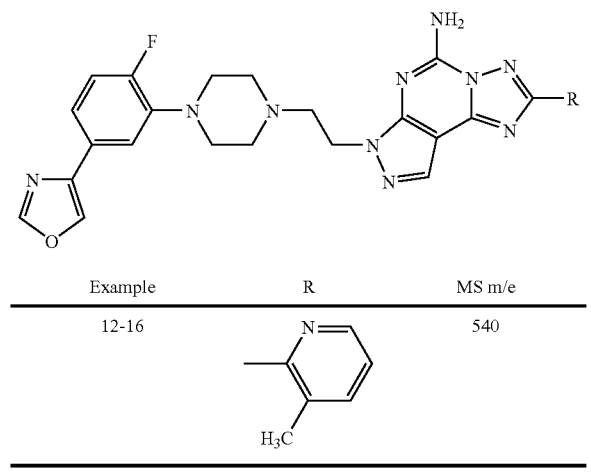

| Example | R | MS m/e |
|---|---|---|
| 12-16 | (2-methyl-pyridin-3-yl) | 540 |

Similarly, from Preparation 77-2, prepare Example 12-17 as a yellow solid, MS: m/e=554 (M+1).

From Preparation 77-3, prepare Example 12-18 as a yellow solid, MS: m/e=540 (M+1).

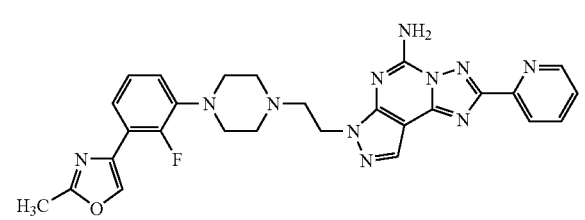

From Preparation 80, prepare Example 12-19 as a yellow solid, MS: m/e=554 (M+1).

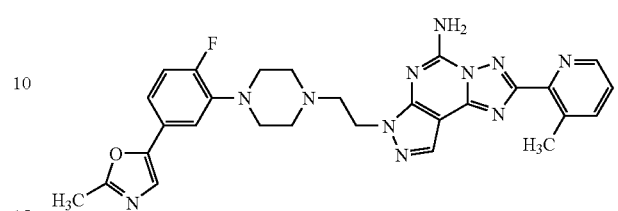

Employ the appropriate chloride from Preparation 4 together with Preparation 80 to prepare the following compounds:

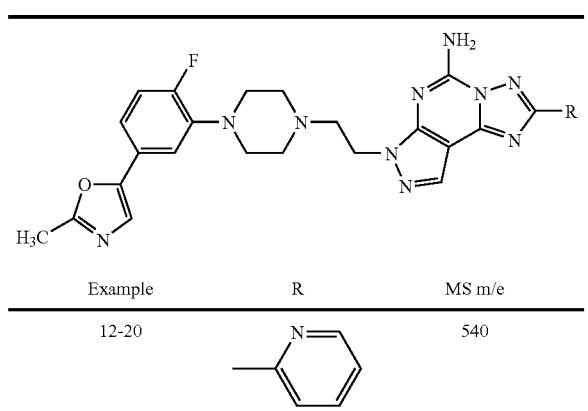

| Example | R | MS m/e |
|---|---|---|
| 12-20 | 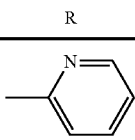 | 540 |
| 12-21 | 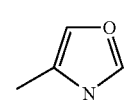 | 530 |
| 12-22 | 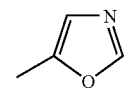 | 530 |

From Prep. 91, prepare Ex. 12-23 as a yellow solid, MS: m/e=526 (M+1)

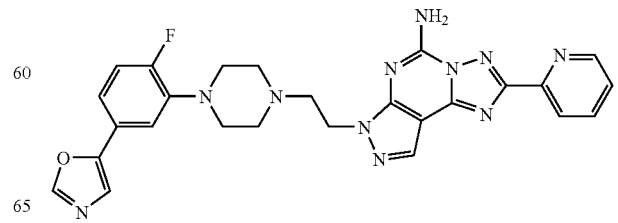

From Prep. 82, prepare Ex. 12-24 as a yellow solid, MS: m/e=554 (M+1).
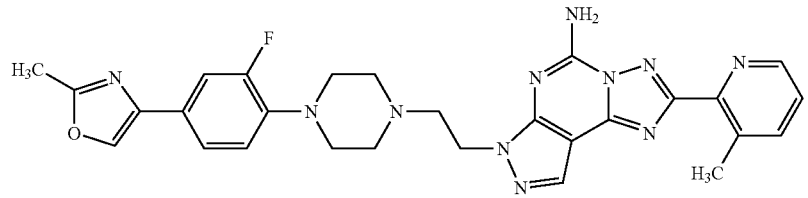
From Prep. 82, prepare Ex. 12-25 as a yellow solid, MS: m/e=540 (M+1)
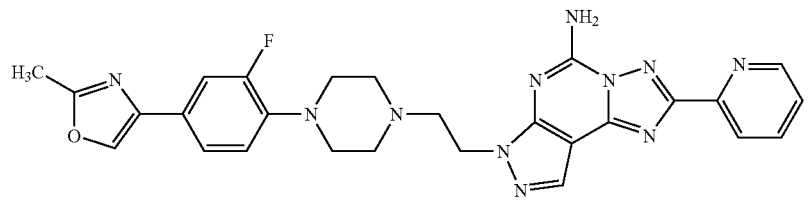
From Prep. 83, prepare Ex. 12-26 as a yellow solid, MS: m/e=525 (M+1).
From Prep. 84, prepare Ex. 12-28 as a yellow solid, MS: m/e=540 (M+1).
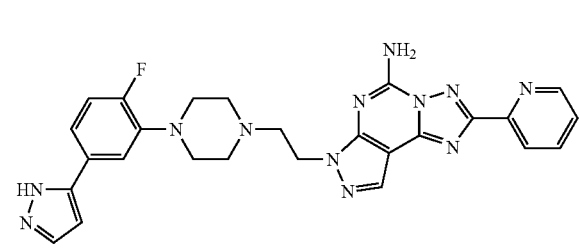
From Prep. 83-2, prepare Ex. 12-27 as a yellow solid, MS: m/e=553 (M+1).
From Prep. 84, prepare Ex. 12-29 as a yellow solid, MS: m/e=554 (M+1)
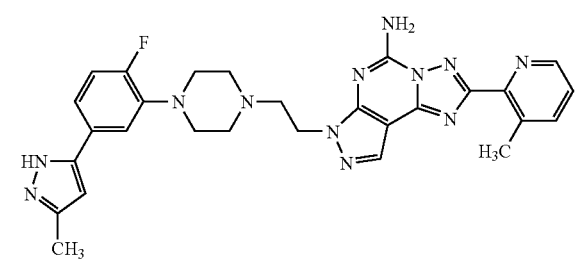
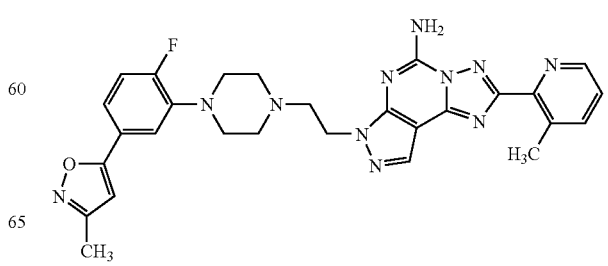

From Prep. 78, prepare Ex. 12-30 as a yellow solid, MS: m/e=556 (M+1)

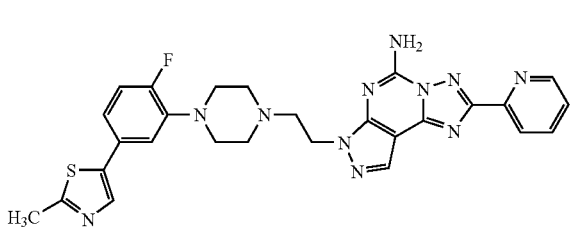

From Prep. 79, prepare Ex. 12-31 as a yellow solid, MS: m/e=526 (M+1)

Example 13

In similar fashion to Example 12, employ the appropriate chloride from Preparation 4 together with Preparation 85 to prepare the following compounds:

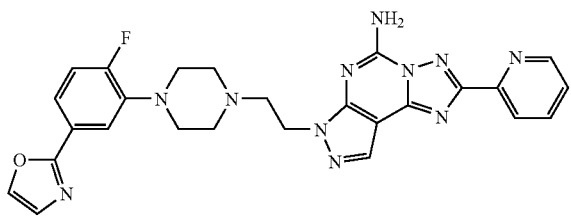

| Example | R | MS m/e |
|---|---|---|
| 13 | 2-pyridyl | 541 |
| 13-2 | 2-methyl-3-pyridyl | 555 |
| 13-3 | 3-cyanophenyl | 565 |
| 13-4 | 2-methyl-3-bromo-pyridyl | 619, 621 |
| 13-5 | 4-methyl-5-oxazolyl | 545 |
| 13-6 | 2-methyl-3-fluoro-pyridyl | 559 |

In similar fashion, employ the appropriate chloride from Preparation 4 together with Preparation 86 to prepare the following compounds:

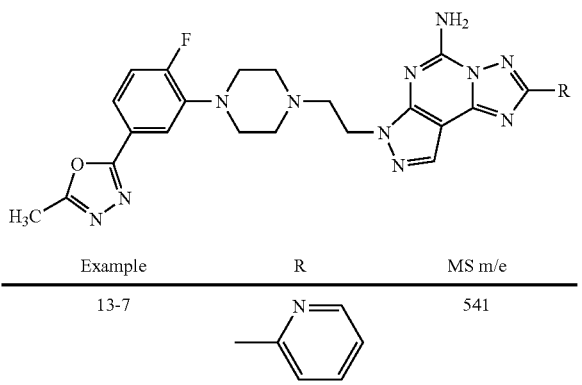
| Example | R | MS m/e |
|---|---|---|
| 13-7 | 6-methylpyridin-2-yl | 541 |
| 13-8 | 2-methyl-3-pyridyl (with H₃C) | 555 |
| 13-9 | 3-cyanophenyl (CN) | 565 |
From Preparation 87, prepare Example 13-10 as a yellow solid, MS: m/e=523 (M+1).
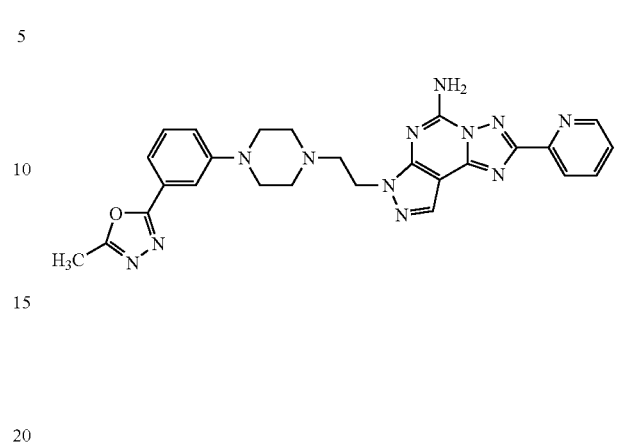
From Preparation 85-2, prepare Example 13-11 as a brown solid, MS: m/e=537 (M+1).
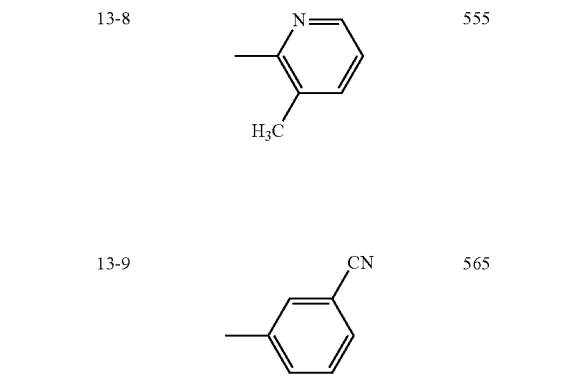
From Preparation 88, prepare Example 13-12 as a brown solid, MS: m/e=555 (M+1).
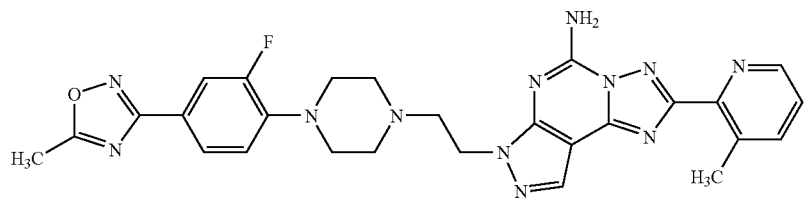

Example 14

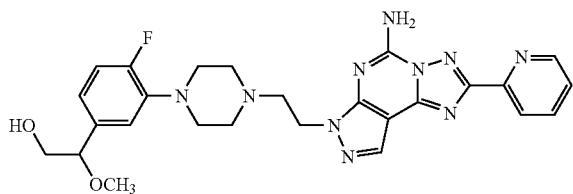

In similar fashion to Example 12, employ Preparation 4-6 together with Preparation 65 to prepare the title compound as a yellow solid, MS: m/e=533 (M+1).

Example 15

In similar fashion to Example 12, combine Preparation 4-8 together with Preparation 89 to prepare the title compound, a tan solid, MS: m/e=565 (M+1).

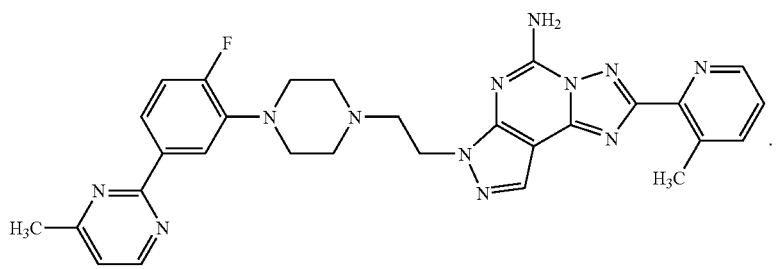

Example 16

Similarly to Ex. 12, combine Prep. 4-6 with Prep. 92 to prepare the title compound, a yellow solid, MS: m/e=584 (M+1).

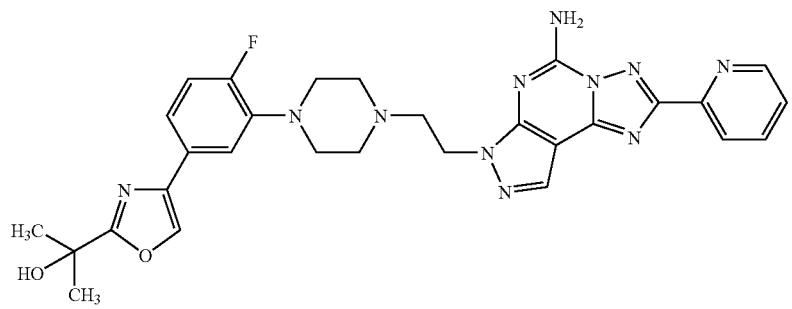

Similarly, from Prep. 4-8, prepare Ex. 16-2, a yellow solid, MS: m/e=598 (M+1).
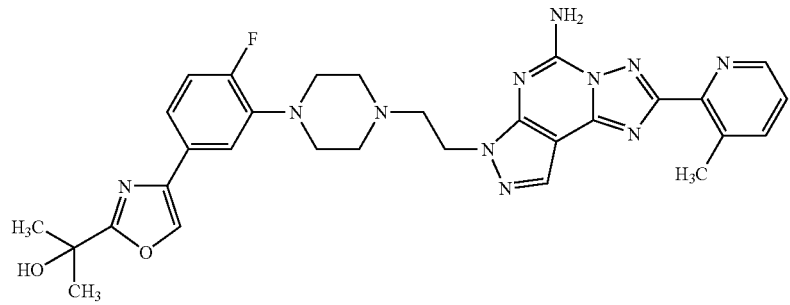
Similarly, combine Prep. 4-6 with Prep. 93 to prepare Ex. 16-3, a yellow solid, MS: m/e=570 (M+1).
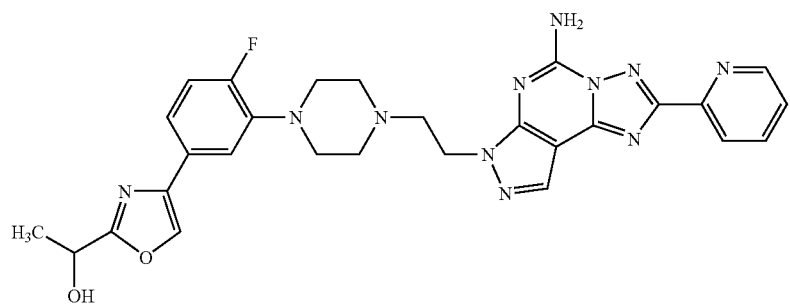
Similarly, from Prep. 4-8, prepare Ex. 16-4, a yellow solid, MS: m/e=584 (M+1).
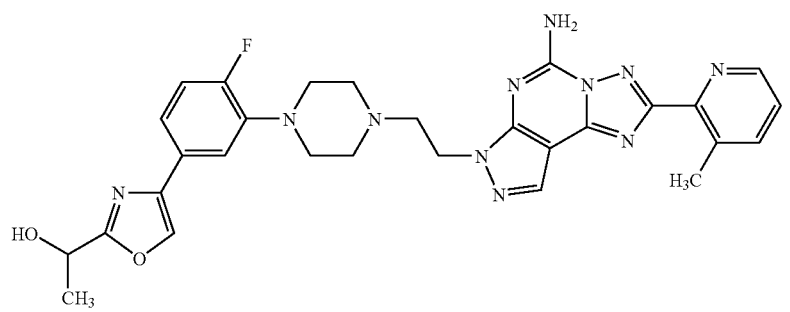

Similarly, combine Prep. 4-6 with Prep. 94 to prepare Ex. 16-5, a yellow solid, MS: m/e=570 (M+1).
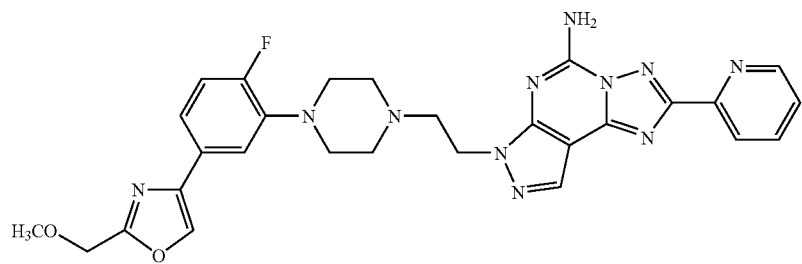
Similarly, from Prep. 4-8, prepare Ex. 16-6, a yellow solid, MS: m/e=584 (M+1).
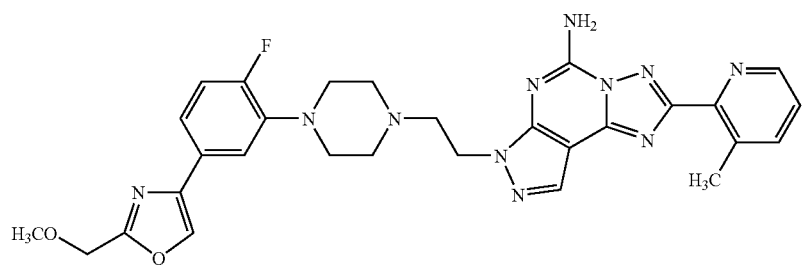
Similarly, from Prep. 4-20, prepare Ex. 16-7, a yellow solid, MS: m/e=588 (M+1).
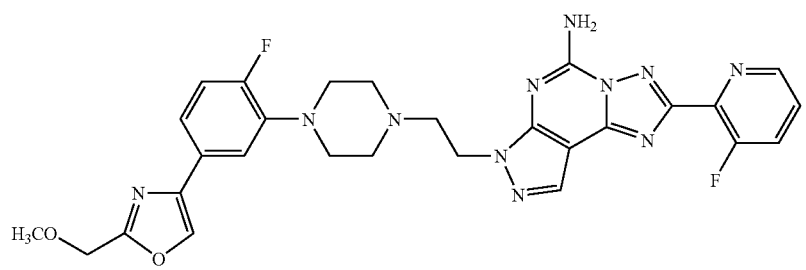

Example 17

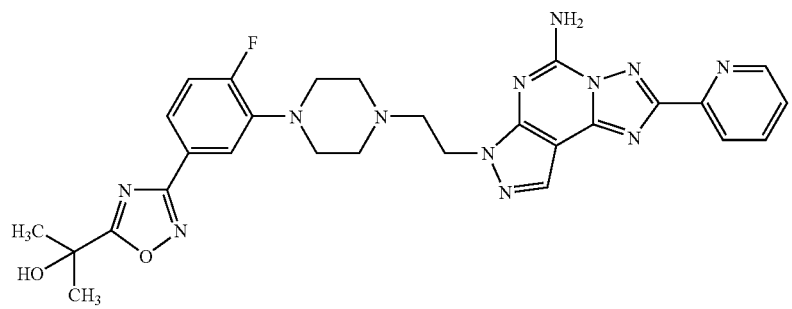

In similar fashion to Example 12, combine Preparation 4-6 with Preparation 97 to prepare the title compound, a tan solid, MS: m/e=585 (M+1).

Employ the appropriate chloride from Preparation 4 with Preparation 97 to prepare the following compounds:

| Example | R | MS m/e |
|---|---|---|
| 17-2 | 2-methyl-3-pyridyl (3-methyl-2-pyridyl) | 599 |
| 17-3 | 3-fluoro-2-pyridyl (2-methyl-3-fluoropyridyl) | 603 |
| 17-4 | 3-cyanophenyl (methyl) | 609 |
| 17-5 | 4-methyl-5-methyloxazolyl | 589 |

Similarly, combine Prep. 4-6 with Prep. 96 to prepare Ex. 17-6, a white solid, MS: m/e=571 (M+1).

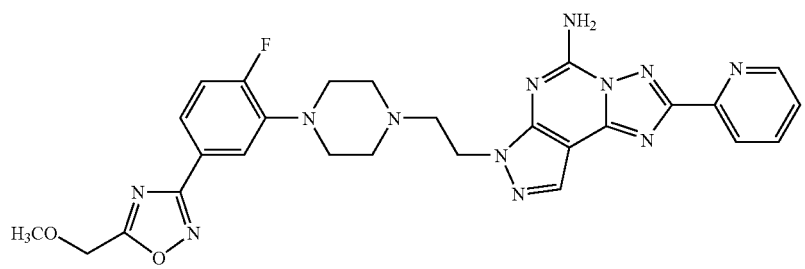

Employ the appropriate chloride from Prep. 4 with Prep. 96 to prepare the following compounds:
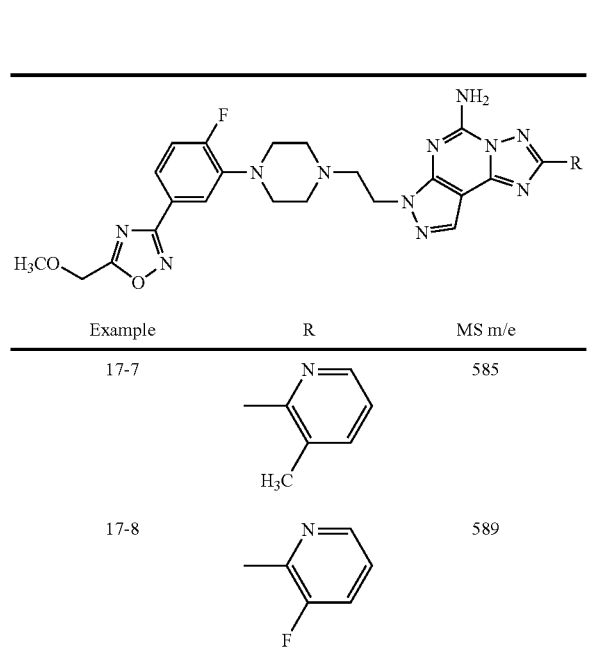
| Example | R | MS m/e |
|---|---|---|
| 17-7 | 2,3-dimethylpyridinyl | 585 |
| 17-8 | 3-fluoro-2-methylpyridinyl | 589 |
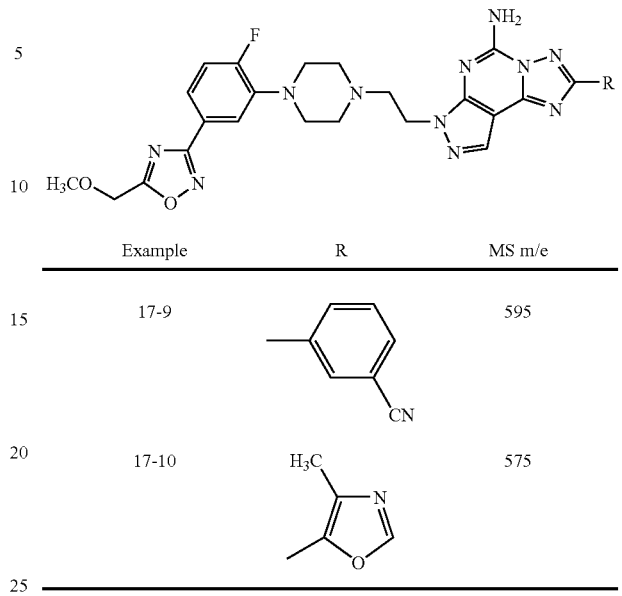
| Example | R | MS m/e |
|---|---|---|
| 17-9 | 3-cyano-5-methylphenyl | 595 |
| 17-10 | 4,5-dimethyloxazolyl | 575 |
Similarly, combine Prep. 4-8 with Prep. 88-2 to prepare Ex. 17-11, a white solid, MS: m/e=557 (M+1).
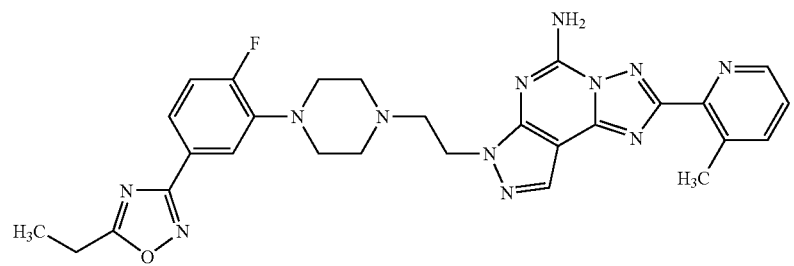
Similarly, combine Prep. 4-8 with Prep. 98 to prepare Ex. 17-12, a tan solid, MS: m/e=624 (M+1).
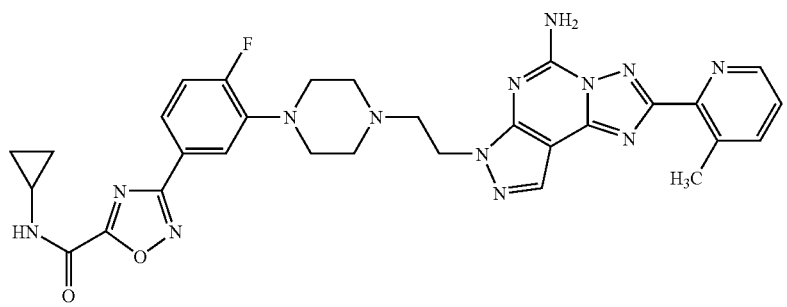

Example 18

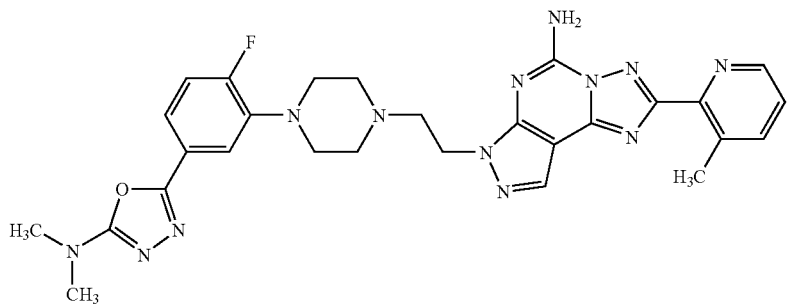

In similar fashion to Example 12, combine Preparation 4-8 with Preparation 95 to prepare the title compound, a tan solid, MS: m/e=584 (M+1).

Example 19

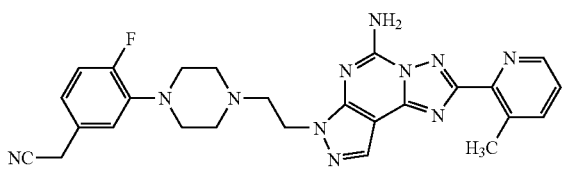

In similar fashion to Example 12, combine Preparation 4-8 with Preparation 36 to prepare the title compound, a yellow solid, MS: m/e=512 (M+1).

Because of their adenosine $A_{2a}$ receptor antagonist activity, compounds of the present invention are useful in the treatment of depression, cognitive function diseases and neurodegenerative diseases such as Parkinson's disease, senile dementia as in Alzheimer's disease, psychoses, attention deficit disorders, EPS, dystonia, RLS and PLMS. In particular, the compounds of the present invention can improve motor-impairment due to neurodegenerative diseases such as Parkinson's disease.

The other agents known to be useful in the treatment of Parkinson's disease that can be administered in combination with the compounds of formula I include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; and COMT inhibitors such as tolcapone and entacapone.

In this specification, the term "at least one compound of formula I" means that one to three different compounds of formula I may be used in a pharmaceutical composition or method of treatment. Preferably one compound of formula I is used. Similarly, "one or more agents useful in the treatment of Parkinson's disease" means that one to three different agents, preferably one agent, may be used in a pharmaceutical composition or method of treatment. Preferably, one agent is used in combination with one compound of formula I.

The pharmacological activity of the compounds of the invention was determined by the following in vitro and in vivo assays to measure $A_{2a}$ receptor activity.

Human Adenosine $A_{2a}$ and $A_1$ Receptor Competition Binding Assay Protocol

Membrane Sources:
$A_{2a}$: Human $A_{2a}$ Adenosine Receptor membranes, Catalog #RB-HA2a, Receptor Biology, Inc., Beltsville, Md. Dilute to 17 µg/100 µl in membrane dilution buffer (see below).

Assay Buffers:
Membrane dilution buffer: Dulbecco's Phosphate Buffered Saline (Gibco/BRL)+10 mM $MgCl_2$.
Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.

Ligands:
$A_{2a}$: [3H]-SCH 58261, custom synthesis, AmershamPharmacia Biotech, Piscataway, N.J. Stock is prepared at 1 nM in membrane dilution buffer. Final assay concentration is 0.5 nM.
$A_1$: [3H]-DPCPX, AmershamPharmacia Biotech, Piscataway, N.J. Stock is prepared at 2 nM in membrane dilution buffer. Final assay concentration is 1 nM.

Non-Specific Binding:
$A_{2a}$: To determine non-specific binding, add 100 nM CGS 15923 (RBI, Natick, Mass.). Working stock is prepared at 400 nM in compound dilution buffer.
$A_1$: To determine non-specific binding, add 100 µM NECA (RBI, Natick, Mass.). Working stock is prepared at 400 µM in compound dilution buffer.

Compound Dilution:
Prepare 1 mM stock solutions of compounds in 100% DMSO. Dilute in compound dilution buffer. Test at 10 concentrations ranging from 3 µM to 30 pM. Prepare working solutions at 4× final concentration in compound dilution buffer.

Assay Procedure:
Perform assays in deep well 96 well plates. Total assay volume is 200 µl. Add 50 µl compound dilution buffer (total ligand binding) or 50 µl CGS 15923 working solution ($A_{2a}$ non-specific binding) or 50 µl, NECA working solution ($A_1$ non-specific binding) or 50 µl of drug working solution. Add 50 µl ligand stock ([3H]-SCH 58261 for $A_{2a}$, [3H]-DPCPX for $A_1$). Add 100 µl of diluted membranes containing the appropriate receptor. Mix. Incubate at room temperature for 90 minutes. Harvest using a Brandel cell harvester onto Packard GF/B filter plates. Add 45 µl Microscint 20 (Packard), and count using the Packard TopCount Microscintillation Counter. Determine $IC_{50}$ values by fitting the displacement curves using an iterative curve fitting program (Excel). Determine Ki values using the Cheng-Prusoff equation.

Haloperidol-Induced Catalepsy in the Rat

Male Sprague-Dawley rats (Charles River, Calco, Italy) weighing 175-200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglass cage placed at an angle of about 70 degrees with the bench table. The rat is placed on the grid with all four legs abducted and extended ("frog posture"). The use of such an unnatural posture is essential for the specificity of this test for catalepsy. The time span from placement of the paws until the first complete removal of one paw (descent latency) is measured maximally for 120 sec.

The selective $A_{2A}$ adenosine antagonists under evaluation are administered orally at doses ranging between 0.03 and 3 mg/kg, 1 and 4 h before scoring the animals.

In separate experiments, the anticataleptic effects of the reference compound, L-DOPA (25, 50 and 100 mg/kg, ip), were determined.

6-OHDA Lesion of the Middle Forebrain Bundle in Rats

Adult male Sprague-Dowley rats (Charles River, Calco, Como, Italy), weighing 275-300 g, are used in all experiments. The rats are housed in groups of 4 per cage, with free access to food and water, under controlled temperature and 12 hour light/dark cycle. The day before the surgery the rats are fasted over night with water ad libitum.

Unilateral 6-hydroxydopamine (6-OHDA) lesion of the middle forebrain bundle is performed according to the method described by Ungerstedt et al. (*Brain Research*, 24 (1970), p. 485-493; *European Journal of Pharmacology*, 5 (1968), p. 107-110), with minor changes. Briefly, the animals are anaesthetized with chloral hydrate (400 mg/kg, ip) and treated with desipramine (10 mpk, ip) 30 min prior to 6-OHDA injection in order to block the uptake of the toxin by the noradrenergic terminals. Then, the animals are placed in a stereotaxic frame. The skin over the skull is reflected and the stereotaxic coordinates (−2.2 posterior from bregma (AP), +1.5 lateral from bregma (ML), 7.8 ventral from dura (DV) are taken, according to the atlas of Pellegrino et al (Pellegrino L. J., Pellegrino A. S. and Cushman A. J., *A Stereotaxic Atlas of the Rat Brain*, 1979, New York: Plenum Press). A burr hole is then placed in the skull over the lesion site and a needle, attached to a Hamilton syringe, is lowered into the left MFB. Then 8 µg 6-OHDA-HCl is dissolved in 4 µl of saline with 0.05% ascorbic acid as antioxidant, and infused at the constant flow rate of 1 µl/1 min using an infusion pump. The needle is withdrawn after additional 5 min and the surgical wound is closed and the animals left to recover for 2 weeks.

Two weeks after the lesion the rats are administered with L-DOPA (50 mg/kg, ip) plus Benserazide (25 mg/kg, ip) and selected on the basis of the number of full contralateral turns quantified in the 2 h testing period by automated rotameters (priming test). Any rat not showing at least 200 complete turns/2 h is not included in the study.

Selected rats receive the test drug 3 days after the priming test (maximal dopamine receptor supersensitivity). The new $A_{2A}$ receptor antagonists are administered orally at dose levels ranging between 0.1 and 3 mg/kg at different time points (i.e., 1, 6, 12 h) before the injection of a subthreshold dose of L-DOPA (4 mpk, ip) plus benserazide (4 mpk, ip) and the evaluation of turning behavior.

Using the above test procedures, the following results were obtained for preferred and/or representative compounds of the invention.

Results of the binding assay on compounds of the invention showed $A_{2a}$ Ki values of 0.4 to 10 nM, with preferred compounds showing Ki values between 0.3 and 5.0 nM. For example, the compound of Example 12-31 has a Ki of 0.3 nM.

Selectivity is determined by dividing Ki for A1 receptor by Ki for $A_{2a}$ receptor. Preferred compounds of the invention have a selectivity ranging from about 100 to about 2000.

Preferred compounds show a 40-75% decrease in descent latency when tested orally at 1 mg/kg for anti-cataleptic activity in rats.

In the 6-OHDA lesion test, rats dosed orally with 1 mg/kg of the preferred compounds performed 170-440 turns in the two-hour assay period.

In the haloperidol-induced catalepsy test, a combination of sub-threshold amount of a compound of formula I and a sub-threshold amount of L-DOPA showed a significant inhibition of the catalepsy, indicating a synergistic effect. In the 6-OHDA lesion test, test animals administered a combination of a compound of formula I and a sub-threshold amount of L-DOPA demonstrated significantly higher contralateral turning.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen for compounds of formula I is oral administration of from 10 mg to 2000 mg/day preferably 10 to 1000 mg/day, in two to four divided doses to provide relief from central nervous system diseases such as Parkinson's disease or the other disease or conditions listed above.

The doses and dosage regimen of the dopaminergic agents will be determined by the attending clinician in view of the approved doses and dosage regimen in the package insert, taking into consideration the age, sex and condition of the patient and the severity of the disease. It is expected that when the combination of a compound of formula I and a dopaminergic agent is administered, lower doses of the components will be effective compared to the doses of the components administered as monotherapy.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the structural formula

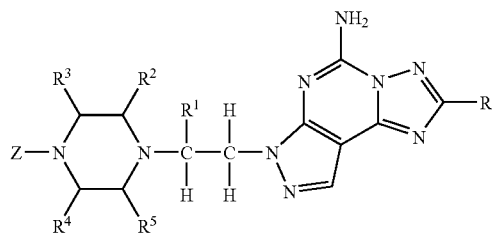

I or a pharmaceutically acceptable salt thereof, wherein
$R^6$ is $R^6$-phenyl, $R^6$-furanyl, $R^6$-thienyl, $R^6$-pyridyl, $R^6$-pyridyl N-oxide, $R^6$-oxazolyl, $R^6$-pyrrolyl or cycloalkenyl;
$R^1$, $R^2$, $R^3$, $R^4$ and $R^5$ are independently selected from the group consisting of H, alkyl and alkoxyalkyl;
$R^6$ is 1 to 3 substituents independently selected from the group consisting of H, alkyl, —$CF_3$, halogen, —$NO_2$, —CN, —$NR^7R^8$, alkoxy, alkylthio, alkylsulfinyl and alkylsulfonyl;
$R^7$ is H or alkyl;
$R^8$ is H, alkyl, alkylC(O)— or alkyl-$SO_2$—;
Z is $R^9,R^{10}$-aryl or $R^9,R^{10}$-heteroaryl;
$R^9$ is alkenyl, hydroxyalkyl, alkoxyalkyl, alkoxy-alkoxy-alkyl-, (di-alkoxy)-alkyl, (hydroxy)-alkoxyalkyl, $R^{15}$-cycloalkyl, $R^{15}$-cycloalkylalkyl, cycloalkyl-oxy, cycloalkyl-O-alkoxy, cyanoalkyl, $N(R^{11})(R^{12})$-alkyl-, —$C(O)N(R^{13})(R^{16})$, -alkylene-C(O)—$N(R^{11})_2$, —C(O)—($R^{15}$-heterocycloalkyl), $R^{15}$-heterocycloalkyl-alkyl, $R^{19}$-heteroaryl, $CF_3$-alkylene-O-alkyl, $CF_3$-hydroxyalkyl, ($CF_3$)(hydroxy)alkoxy, cyanoalkoxy, -alkylene-C(O)—O-alkyl, —$SO_2$—$N(alkyl)_2$, (cycloalkyl)hydroxyalkyl, (hydroxyalkyl)alkoxy, (dihydroxy)alkyl, (dihydroxy)alkoxy or —C(=$NOR^{17}$)—$CF_3$;
$R^{10}$ is 1 to 3 substituents independently selected from the group consisting of hydrogen, alkyl, alkenyl, hydroxy, alkoxy, hydroxyalkyl, hydroxy-alkoxy, alkoxyalkyl, alkoxyalkoxy, alkoxy-alkoxy-alkyl-, (di-alkoxy)-alkyl, (hydroxy)-alkoxyalkyl, $R^{15}$-cycloalkyl, $R^{15}$-cycloalkylalkyl, cycloalkyl-oxy, cycloalkyl-O-alkoxy, alkyl-$SO_2$—, alkyl-SO—, halo, —ON, cyanoalkyl, —$CHF_2$, —$CF_3$, —$OCHF_2$, —$OCF_3$, —$O(C)R^{13}$, —O-alkylene-$C(O)OR^{13}$, —C(O)O-alkyl, —$N(R^{11})(R^{12})$, $N(R^{11})(R^{12})$-alkyl, $N(R^{11})(R^{12})$-alkoxy, —$C(O)N(R^{13})(R^{16})$, $R^{19}$-heteroaryl, $R^{15}$-heterocycloalkyl, $R^{15}$-heterocycloalkyl-alkyl, $R^{15}$-heterocycloalkyl-alkoxy $R^{15}$-heterocycloalkyl-oxy, $CF_3$-alkylene-O-alkyl, $CF_3$-hydroxyalkyl, ($CF_3$)(hydroxy)alkoxy, cyano-alkoxy, -alkylene-C(O)—O-alkyl, —$SO_2$—$N(alkyl)_2$, (cycloalkyl)hydroxyalkyl, (hydroxyalkyl)alkoxy, (dihydroxy)alkyl, (dihydroxy)alkoxy, —O(=$NOR^{17}$)-alkyl and —$C(NOR^{17})$—$CF_3$;
or an $R^9$ group and an $R^{10}$ group on adjacent carbon ring atoms together form —$CH_2$—O—$(CH_2)_2$—O—, —O—$(CH_2)_2$—, —$(CH_2)_3$—O—, —O—$(CH_2)_3$—O—, —$(CH_2)_3$— or —$CH_2$—CH=OH—, wherein the ring formed by the $R^9$ and $R^{10}$ substituents and the ring carbon atoms to which they are attached is substituted by $R^{16}$;
or an $R^9$ group and an $R^{10}$ group on adjacent carbon ring atoms together form —$N(R^{11})$—C(O)—O—, $N(R^{11})$—C(O)—S— or —$N(R^{12})$—$(CH_2)_2$—;
or an $R^9$ and an $R^{10}$ group on adjacent carbon ring atoms together form —$(CH_2)_2CH(OR^{18})$—, —$CH_2CH(OR^{18})CH_2$—, —$(CH_2)_3CH(OR^{18})$—, —$(CH_2)_2CH(OR^{18})CH_2$—, —$(CH_2)_2C(O)$—, —$CH_2C(O)CH_2$—, —$(CH_2)_3$ C(O)—, —$(CH_2)_2C(O)CH_2$—, —$O(CH_2)_2$ $CH(OR^{18})$— or —$OCH_2CH(OR^{18})CH_2$—, wherein the ring formed by the $R^9$ and $R^{10}$ substituents and the ring carbon atoms to which they are attached is optionally substituted on a carbon atom by hydroxyalkyl or alkoxyalkyl;
each $R^{11}$ is independently selected from the group consisting of H and alkyl;
each $R^{12}$ is independently selected from the group consisting of H, alkyl, cycloalkyl, hydroxyalkyl, alkoxyalkyl, —C(O)-alkyl, —C(O)O-alkyl, (alkoxy)hydroxyalkyl, alkoxyalkyl-C(O)—, —$SO_2$alkyl, -alkylene-C(O)alkyl and -alkylene-C(O)O-alkyl;
$R^{13}$ is H, alkyl or —$CF_3$;
$R^{15}$ is 1 to 3 substituents independently selected from the group consisting of H, alkyl, —OH, alkoxy, alkoxyalkyl and hydroxyalkyl; or two $R^{15}$ substituents, taken together with the carbon to which they are both attached, form a —C(=O)— group;
$R^{16}$ is H, alkyl, alkoxyalkyl, OH or hydroxyalkyl;
$R^{17}$ is H or alkyl;
$R^{18}$ is H or alkyl; and
$R^{19}$ is 1 or 2 substituents independently selected from the group consisting of H, alkyl, hydroxyalkyl, alkoxyalkyl, —$C(O)N(R^{11})(R^{12})$ and —$N(R^{11})_2$.

2. A compound of claim 1 wherein R is $R^6$-phenyl, $R^6$-furanyl, $R^6$-thienyl, $R^6$-pyridyl or $R^6$-oxazolyl.

3. A compound of claim 2 wherein $R^6$ is $R^6$-furanyl or $R^6$-pyridyl.

4. A compound of claim 3 wherein $R^6$ is H, halogen or alkyl.

5. A compound of claim 1 wherein $R^2$, $R^3$, $R^4$ and $R^5$ are each H.

6. A compound of claim 1 wherein Z is $R^9$,$R^{10}$-phenyl.

7. A compound of claim 6 wherein $R^9$ is hydroxyalkyl, alkoxyalkyl, (hydroxy)-alkoxyalkyl, (hydroxyalkyl)alkoxy, $R^{15}$-cycloalkyl, cyanoalkyl, $R^{19}$-heteroaryl, or (cycloalkyl)hydroxyalkyl.

8. A compound of claim 6 wherein $R^{10}$ is 1 or 2 substituents independently selected from the group consisting of H, halo, —C(O)$R^{13}$, alkoxy, hydroxyalkyl, hydroxyalkoxy, alkoxyalkoxy, alkoxyalkyl, and cyanoalkyl.

9. A compound of claim 6 wherein $R^9$ is hydroxyalkyl, (hydroxyalkyl)alkoxy, $R^{15}$-cycloalkyl, cyanoalkyl, $R^{19}$-heteroaryl, or (cycloalkyl)hydroxyalkyl, and $R^{10}$ is 1 or 2 substituents independently selected from the group consisting of H, halo and alkoxy.

10. A compound of claim 1 wherein $R^6$ is $R^6$-furanyl or $R^2$-pyridyl, $R^2$, $R^3$, $R^4$ and $R^5$ are each H, and Z is $R^9 R^{10}$-phenyl.

11. A compound of claim 10 wherein $R^9$ is hydroxyalkyl, (hydroxyalkyl)alkoxy, $R^{15}$-cycloalkyl, cyanoalkyl, $R^{19}$-heteroaryl, or (cycloalkyl)hydroxyalkyl, and $R^{10}$ is o-fluoro.

12. A compound selected from the group consisting of

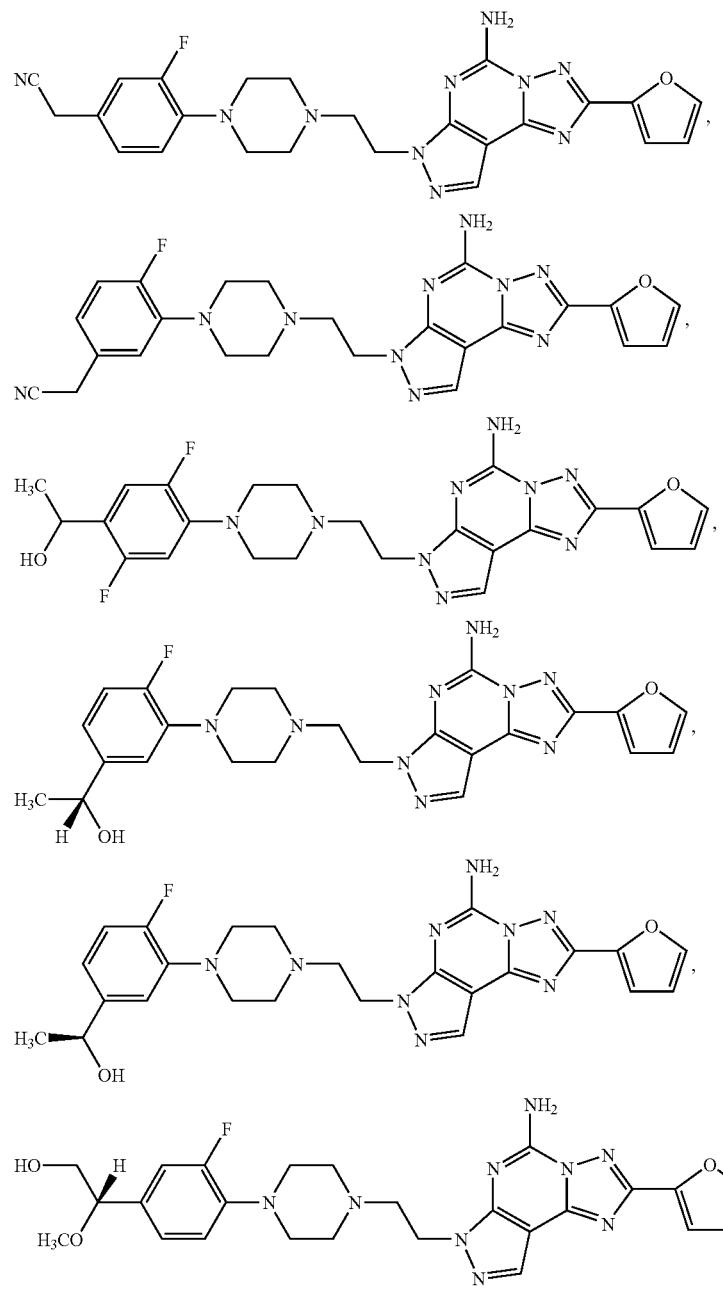

-continued
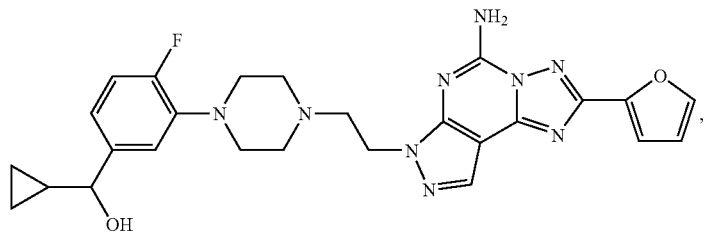
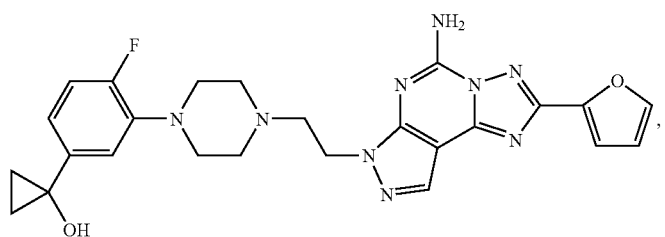
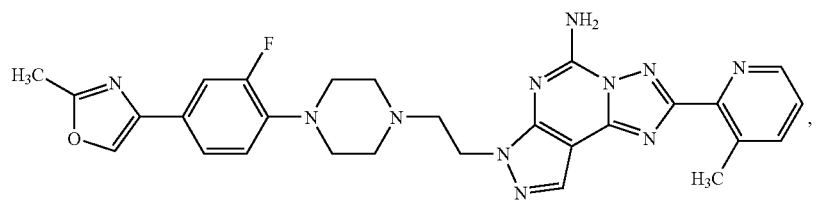
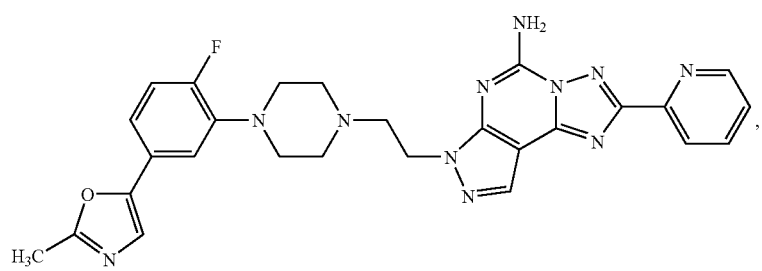
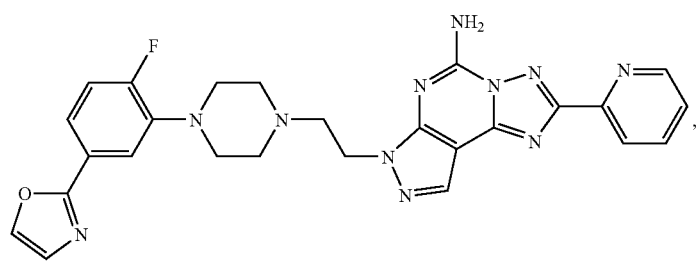
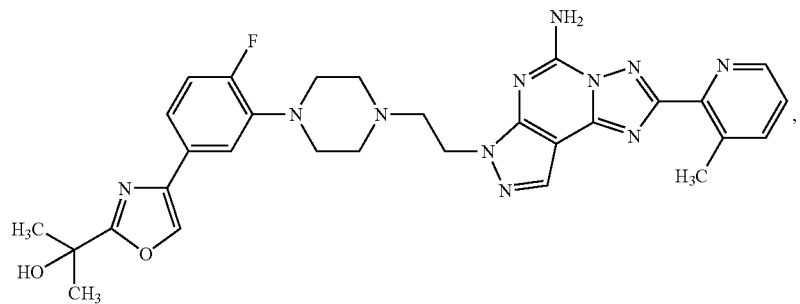

-continued

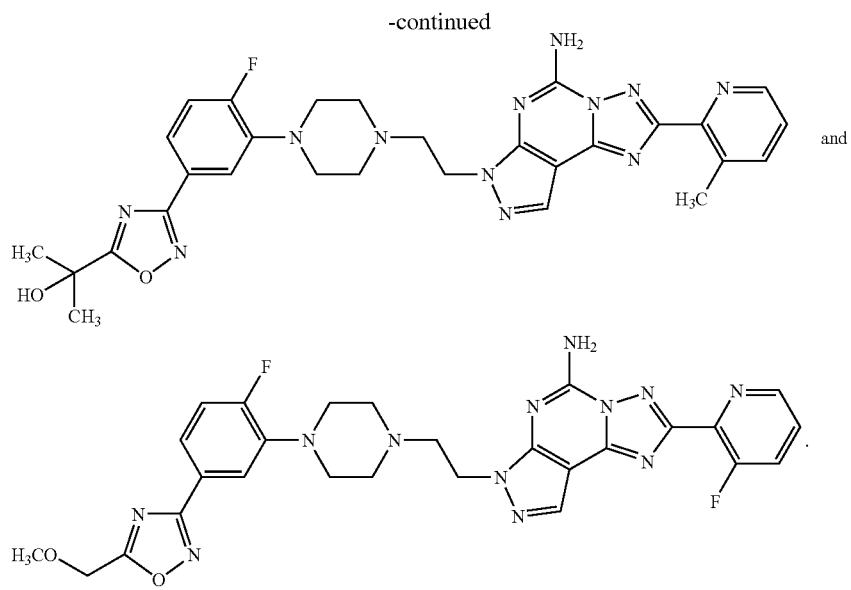

13. A pharmaceutical composition comprising a therapeutically effective amount of a compound of claim 1 in a pharmaceutically acceptable carrier.

14. A method of treating Parkinson's disease, attention deficit disorder, Extra Pyramidal Syndrome, restless leg syndrome or periodic limb movement in sleep, comprising administering an effective amount of a compound of formula I of claim 1 to a mammal in need of such treatment.

15. A pharmaceutical composition comprising a therapeutically effective amount of a combination of a compound of claim 1, and 1 to 3 other agents useful in treating Parkinson's disease in a pharmaceutically acceptable carrier, wherein said other agents are selected from the group consisting of L-DOPA, dopaminergic agonists, MAO-B inhibitors, DOPA decarboxylase inhibitors and COMT inhibitors.

16. A method of treating Parkinson's disease comprising administering to a mammal in need of such treatment an effective amount of a combination of a compound of claim 1, and 1 to 3 other agents useful in treating Parkinson's disease, wherein said other agents are selected from the group consisting of L-DOPA, dopaminergic agonists, MAO-B inhibitors, DOPA decarboxylase inhibitors and COMT inhibitors.

17. A pharmaceutical composition comprising a therapeutically effective amount of a compound of claim 12 in a pharmaceutically acceptable carrier.

18. A method of treating Parkinson's disease, attention deficit disorder, Extra Pyramidal Syndrome, restless leg syndrome or periodic limb movement in sleep, comprising administering an effective amount of a compound of claim 12 to a mammal in need of such treatment.

19. A pharmaceutical composition comprising a therapeutically effective amount of a combination of a compound of claim 12, and 1 to 3 other agents useful in treating Parkinson's disease in a pharmaceutically acceptable carrier, wherein said other agents are selected from the group consisting of L-DOPA, dopaminergic agonists, MAO-B inhibitors, DOPA decarboxylase inhibitors and COMT inhibitors.

20. A method of treating Parkinson's disease comprising administering to a mammal in need of such treatment an effective amount of a combination of a compound of claim 12, and 1 to 3 other agents useful in treating Parkinson's disease, wherein said other agents are selected from the group consisting of L-DOPA, dopaminergic agonists, MAO-B inhibitors, DOPA decarboxylase inhibitors and COMT inhibitors.

\* \* \* \* \*